US008158590B2

(12) United States Patent
Beusker et al.

(10) Patent No.: US 8,158,590 B2
(45) Date of Patent: Apr. 17, 2012

(54) TRIAZOLE-CONTAINING RELEASABLE LINKERS, CONJUGATES THEREOF, AND METHODS OF PREPARATION

(75) Inventors: Patrick Henry Beusker, Nijmegen (NL); Franciscus Marinus Hendrikus De Groot, Nijmegen (NL)

(73) Assignee: Syntarga B.V., Nijmegen (NL)

( * ) Notice: Subject to any disclaimer, the term of this patent is extended or adjusted under 35 U.S.C. 154(b) by 806 days.

(21) Appl. No.: 11/997,981

(22) PCT Filed: Aug. 3, 2006

(86) PCT No.: PCT/NL2006/050192
§ 371 (c)(1),
(2), (4) Date: Aug. 6, 2008

(87) PCT Pub. No.: WO2007/018431
PCT Pub. Date: Feb. 15, 2007

(65) Prior Publication Data
US 2008/0311136 A1 Dec. 18, 2008

(30) Foreign Application Priority Data
Aug. 5, 2005 (WO) ................ PCT/NL2005/000576

(51) Int. Cl.
*A61K 38/07* (2006.01)
*A61P 31/00* (2006.01)
(52) U.S. Cl. ...................................... 514/21.9; 514/19.3
(58) Field of Classification Search ........................ None
See application file for complete search history.

(56) References Cited

U.S. PATENT DOCUMENTS
7,056,942 B2 * 6/2006 Hildesheim et al. .......... 514/411

FOREIGN PATENT DOCUMENTS
| EP | 1 243 276 | | 9/2002 |
|---|---|---|---|
| EP | 1 733 742 A1 | | 12/2006 |
| WO | WO 02/083180 | * | 10/2002 |
| WO | 03/101972 A1 | | 12/2003 |
| WO | WO2004/043493 | | 5/2004 |
| WO | WO2005/025512 | | 3/2005 |
| WO | 2006/116736 A2 | | 11/2006 |
| WO | 2007/011696 A2 | | 1/2007 |

OTHER PUBLICATIONS

Vippagunta et al ('Crystalline solids' Adv. Drug Delivery Rev. v48 2001 pp. 3-26).*
de Groot et al ('Elongated multiple electronic cascade and cyclization spacer systems in activatible anticancer prodrugs for enhanced drug release' J Org Chem v66 2001 pp. 8815-8830).*
The International Search Report and the Written Opinion dated May 17, 2006 for International Application No. PCT/NL2005/000576.
Wang et al., "Bioconjugation by copper(1)-catalyzed . . .", Journal of the American Chemical Society, Mar. 19, 2003, vol. 125, No. 11, pp. 3192-3193.
Speers et al., "Profiling enzyme activities in vivo using click chemistry methods", Chemistry & Biology, Apr. 2004, vol. 11, No. 4, pp. 535-546.
Kolb et al., "The growing impact of click chemistry on drug discovery", Drug Discovery Today, Dec. 15, 2003, vol. 8, No. 24, pp. 1128-1137.
Damen et al., "Synthesis of novel paclitaxel prodrugs . . . ", Bioorganic & Medicinal Chemistry, Jan. 2002, vol. 10, No. 1 pp. 71-77.
De Groot et al., ""Cascade-release dendrimers" liberate all end groups . . . ", Angewandte Chemie, Sep. 29, 2003, vol. 42, No. 37, pp. 4490-4494.
De Groot et al., "Anticancer prodrugs for application in monotherapy . . . ", Current Medicinal Chemistry, Jul. 2001, vol. 8, No. 9, pp. 1093-1122.
Appukkuttan et al., "A Microwave-Assisted Click Chemistry Synthesis of 1,4-Disubstituted 1,2,3-Triazoles via a Copper(1)-Catalyzed Three-Component Reaction," *Organic Letters*, 6(23):4223-4225 (2004).
Chittaboina et al., "One-pot synthesis of triazole-linked glycoconjugates," *Tetrahedron Letters*, 46:2331-2336 (2005).
Khanetskyy et al., "Combining Biginelli Multicomponent and Click Chemistry: Generation of 6-(1,2,3-Triazol-1-yl)-Dihydropyrimidone Libraries," *J. Comb. Chem.*, 6:884-892 (2004).
Link et al., "Cell Surface Labeling of *Escherichia coli* via Copper(1)-Catalyzed [3+2] Cycloaddition," *J. Am. Chem. Soc.*, 125(37):11164-11165 (2003).
Tornøe et al., "Peptidotriazoles on Solid Phase: [1,2,3]-Triazoles by Regiospecific Copper(I)-Catalyzed 1,3-Dipolar Cycloadditions of Terminal Alkynes to Azides," *J. Org. Chem.*, 67(9):3057-3064 (2002).
Wu et al., "Efficiency and Fidelity in a Click-Chemistry Route to Triazole Dendrimers by the Copper(I)Catalyzed Ligation of Azides and Alkynes," *Angew. Chem. Int. Ed.*, 43:3928-3932 (2004).

* cited by examiner

*Primary Examiner* — Cecilia J Tsang
*Assistant Examiner* — Ronald Niebauer
(74) *Attorney, Agent, or Firm* — K&L Gates LLP

(57) ABSTRACT

This invention relates to compounds comprising one or more therapeutic and/or diagnostic moieties and one or more functional moieties linked together via one or more triazole-containing linkers and to their intermediates and methods of their preparation. The triazole-containing linker may optionally contain one or more conditionally-cleavable or conditionally-transformable moieties and one or more spacer systems in between said moiety/moieties and the one or more therapeutic and/or diagnostic moieties.

22 Claims, 6 Drawing Sheets

1,4-adduct

TRIAZOLE-CONTAINING RELEASABLE LINKERS, CONJUGATES THEREOF, AND METHODS OF PREPARATION

REFERENCE TO SEQUENCE LISTING

This application includes a Sequence Listing electronically submitted via EFS-Web as a single text file named "NED-004_ST25.txt". The Sequence Listing text file was created on May 11, 2011 and is 1 kb in size. The contents of the Sequence Listing are hereby incorporated by reference.

FIELD OF THE INVENTION

This invention relates to conjugates comprising one or more therapeutic and/or diagnostic moieties and one or more functional moieties linked together via one or more triazole-containing linkers and to methods of preparing said conjugates. Furthermore this invention concerns intermediates for the preparation of said conjugates and methods of preparing said intermediates. The triazole-containing linker may optionally contain one or more conditionally-cleavable or conditionally-transformable moieties and one or more self-elimination spacer systems in between said moiety/moieties and the one or more therapeutic and/or diagnostic moieties. In one aspect, the conjugates are designed to release their (multiple) payload after one or more activation steps and/or at a rate and time span controlled by the conjugate in order to selectively deliver and/or controllably release one or more therapeutic or diagnostic moieties. The conjugates of this invention and their intermediates can for example be used for diagnostic assays, for controlled in vivo release of therapeutics or diagnostics, or for in vivo targeting of therapeutic or diagnostic moieties to a target site, e.g., target cells. For the latter, target cells are preferably tumor cells.

BACKGROUND OF THE INVENTION

Lack of selectivity of chemotherapeutic agents is a major problem in cancer treatment. Because highly toxic compounds are used in cancer chemotherapy, it is typically associated with severe side effects. Drug concentrations that would completely eradicate the tumor cannot be reached because of dose-limiting side effects such as gastrointestinal tract and bone marrow toxicity. In addition, tumors can develop resistance against anticancer agents after prolonged treatment. In modern drug development, targeting of cytotoxic drugs to the tumor site can be considered one of the primary goals.

One promising approach to obtain selectivity for tumor cells or tumor tissue is to exploit the existence of tumor-associated antigens, receptors, and other receptive moieties, which can serve as a target. Such a target may be upregulated or to some degree be specifically present in tumor tissue or in closely associated tissue, such as neovascular tissue, with respect to other tissues in order to achieve efficient targeting. Many targets have been identified and validated and several methods to identify and validate targets have been developed.[1]

By coupling a ligand, e.g. an antibody or antibody fragment or a derivative thereof, for such a tumor-associated antigen, receptor, or other receptive moiety to a therapeutic or diagnostic agent, this agent can be selectively targeted to tumor tissue. In case the therapeutic or diagnostic moiety needs to be released at the tumor site, some kind of triggering mechanism may be present in the conjugate that is triggered when the conjugate has reached its target in order to release the payload. Such a triggering mechanism can for example be an enzymatic cleavage or a pH-dependent hydrolysis.[2] Alternatively, release may occur non-specifically.

Another promising approach to obtain selectivity for tumor cells or tumor tissue is to exploit the existence of tumor-associated enzymes. A relatively high level of tumor-specific enzyme can convert a pharmacologically inactive prodrug, which consists of an enzymatic substrate directly or indirectly linked to the toxic drug, to the corresponding drug in the vicinity of or inside the tumor. Via this concept a high concentration of toxic anticancer agent can be selectively generated at the tumor site. All tumor cells may be killed if the dose is sufficiently high, which may decrease development of drug-resistant tumor cells.

There are several enzymes that are present at elevated levels in certain tumor tissues. One example is the enzyme β-glucuronidase, which is liberated from certain necrotic tumor areas. Furthermore, several proteolytic enzymes have been shown to be associated with tumor invasion and metastasis. Several proteases, like for example the cathepsins and proteases from the urokinase-type plasminogen activator (u-PA) system are all involved in tumor metastasis. The serine protease plasmin plays a key role in tumor invasion and metastasis. The proteolytically active form of plasmin is formed from its inactive pro-enzyme form plasminogen by u-PA. The tumor-associated presence of plasmin has been exploited for targeting of plasmin-cleavable conjugates or prodrugs.[3]

Enzymes have also been transported to the vicinity of or inside target cells or target tissue via for example antibody-directed enzyme prodrug therapy (ADEPT)[4], polymer-directed enzyme prodrug therapy (PDEPT) or macromolecular-directed enzyme prodrug therapy (MDEPT)[5], virus-directed enzyme prodrug therapy (VDEPT)[6], or gene-directed enzyme prodrug therapy (GDEPT)[7].

Yet another promising approach to obtain selectivity for tumor cells or tumor tissue is to exploit the enhanced permeability and retention (EPR) effect. Through this EPR effect, macromolecules passively accumulate in solid tumors as a consequence of the disorganized pathology of angiogenic tumor vasculature with its discontinuous endothelium, leading to hyperpermeability to large macromolecules, and the lack of effective tumor lymphatic drainage.[8]

By coupling therapeutic or diagnostic agents directly or indirectly to a macromolecule, e.g., a polymer such as for example poly[N-(2-hydroxypropyl)methacrylamide] (HPMA), poly-L-glutamic acid (PG), or polyethylene glycol (PEG), agents have been selectively targeted to tumor tissue. In case the therapeutic or diagnostic moiety needs to be released at the tumor site, some kind of triggering mechanism may be present in the conjugate that is triggered when the conjugate has reached its target in order to release the payload. Such a triggering mechanism can for example be an enzymatic cleavage or a pH-dependent hydrolysis.[9] Alternatively, release may occur non-specifically.

Obviously, two or more targeting approaches such as the above-mentioned approaches to achieve tumor-selective delivery of the therapeutic or diagnostic agents can be combined into a single conjugate.

WO 02/083180 and WO 2004/043493 are relevant disclosures that describe targetable conjugates in which the use of a targeting moiety and the use of a specifier—a unit that can be conditionally cleaved or transformed—are combined to provide for optimal targeting of the one or more therapeutic or diagnostic moieties connected to the cleavable substrate via a self-eliminating spacer or spacer system.

The synthetic routes towards such conjugates comprise some disadvantages. The syntheses of these conjugates are composed of many synthetic steps. Furthermore, routes towards these conjugates regularly require the use of two or more orthogonal protecting groups that all need to be removed under mild conditions, as functional groups in the specifier, linker, and/or the therapeutic/diagnostic moiety or moieties require temporary protection and deprotection must be very mild to save structural integrity. Due to lack of suitable protecting groups, one may even not be able to synthesize some desired conjugates. In addition, new synthetic routes may need to be developed when new coupling strategies are required and the pool of protecting groups that can be chosen from is sometimes limited because of the functionalities and the reactive groups present in the compounds.

It can be understood that the synthetic routes towards conjugates that are structurally similar and that are used for purposes including, but not limited to, in vitro diagnostic assays, in vivo imaging, treatment or prevention of diseases, including cancer, improving the pharmacokinetic properties of agents, or in vivo/ex vivo controlled delivery of agents, may face the same or similar problems.

Thus there is a clear need in the art for improved conjugates that can be prepared with more ease (if they can be prepared at all according to other routes), in less synthetic steps, and according to more generally applicable routes in order to increase the yields and the scope of the conjugates and to reduce the amount of time required to prepare these conjugates.

The recitation of any reference in this section is not an admission that the reference is prior art to this application.

SUMMARY OF THE INVENTION

The present invention fulfills the above-mentioned need with a method to convert an azide-containing or acetylene-containing group in a first compound, wherein said azide-containing or acetylene-containing group serves as a protecting group, into a group containing a reactive moiety and a triazole, said method comprising reacting said azide-containing or acetylene-containing group-containing first compound with respectively an acetylene group or azide group in an acetylene-containing or azide-containing second compound also containing a reactive moiety in a single step under formation of a third compound containing a triazole and a reactive moiety. Optionally said method further comprises reaction of said third compound containing a triazole and a reactive moiety with one or more adjuvant moieties to form a modified third compound containing a triazole and a reactive moiety.

In a second aspect said method further comprises the reaction of said reactive moiety in said third compound or said modified third compound with a functional moiety to form a fourth compound. Optionally said method further comprises reaction of said fourth compound with one or more adjuvant moieties to form a modified fourth compound.

When in this specification and the appended claims reference is made to said third or fourth compound, it should be understood that the same applies to said modified third or fourth compound, respectively, unless the content dictates otherwise.

The present invention also relates to methods wherein said fourth compound is in the form of one of the two complementary formulae

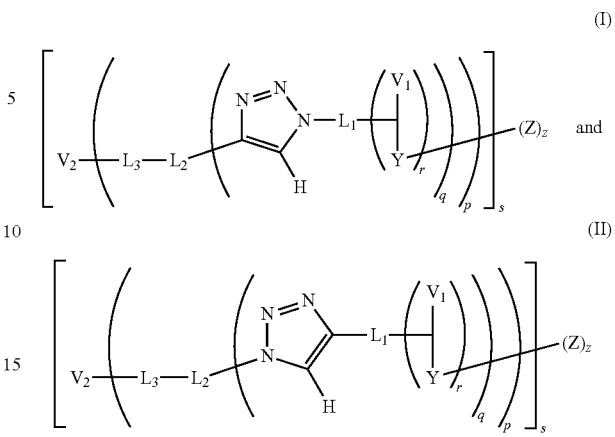

or a pharmaceutically acceptable salt or solvate thereof, wherein

Each $V_2$ is independently a functional moiety;

Each $L_3$ is independently either a bond or a linking group linking $V_2$ to $L_2$;

Each $L_2$ is independently either a bond or a linking group linking $L_3$ to one or more triazole groups;

Each $L_1$ is independently either a bond or a linking group linking the triazole group to one or more $V_1$ and/or Y;

Each $V_1$ is independently a non-cleavable moiety or a conditionally-cleavable moiety, optionally following prior conditional transformation, which can be cleaved or transformed by a chemical, photochemical, physical, biological, or enzymatic process, cleavage of $V_1$ ultimately leading to release of one or more Z moieties;

Each Y is independently absent or a self-eliminating spacer system which is comprised of 1 or more self-elimination spacers;

Each Z is independently H, OH, a leaving group, or a therapeutic or diagnostic moiety, provided that at least one Z is a therapeutic or diagnostic moiety, and each Z is directly coupled to either Y or $V_1$ when Y is absent;

p, q, r, and s are numbers representing degree of branching and are each independently a positive integer;

z is an integer equal to or smaller than the total number of attachment sites for Z in the one or more $V_1$—Y moieties.

It is noted that in this instance, "complementary formulae" refers to the fact that these formulae represent constitutional isomers that may be formed via two similar albeit distinct cycloaddition reactions, the difference being that the two reacting functional groups on the two reaction partners in each of the two cycloaddition reactions are on the opposite reaction partners.

If two adjacent moieties are both a bond, it should be understood that they together represent a bond.

It is further noted that z does not represent a degree of polymerization; hence z does not indicate that a number of moieties Z are connected to one another.

The present invention further relates to methods wherein said first compound is [azide-$L_1$(—$V_1$—Y—)$_r$]$_s$(Z)$_z$ (compound V) or [alkyne-$L_1$(—$V_1$—Y—)$_r$]$_s$(Z)$_z$ (compound VI) and to methods wherein said third compound is [RM-$L_2$(-triazole-$L_1$(—$V_1$—Y—)$_r$)$_q$]$_s$(Z)$_z$ (complementary compounds III and IV, see structures below) in which RM is a reactive moiety.

This invention further relates to compounds of formulae (I), (II), (III), (IV), (V), and (VI).

After extensive protecting group manipulation in order to solve the protecting group problems associated with the synthesis of the type of prior art conjugates described above, the inventors surprisingly found that these problems can be circumvented using a completely different and unique approach. Compounds of formula (I) and (II) can be prepared with more ease than similar compounds in the prior art by way of a mild and selective cycloaddition reaction in which a triazole ring is formed. This reaction is used to transform a protecting group (azide-$L_1$ or alkyne-$L_1$) on $V_1$ or on Y into a reactive moiety (RM-$L_2$-triazole-$L_1$)[10] in a single step. Hereinbelow "on $V_1$ or on Y" is denoted as "on $V_1$/Y". The moiety azide-$L_1$ or alkyne-$L_1$ protects a functional group on each $V_1$/Y throughout (a large part of) the synthesis of a compound of formula (V) or (VI). It can then be efficiently transformed into the moiety RM-$L_2$-triazole-$L_1$ under very mild conditions. This unique approach has the advantages that:

(a) there is no need to carry out a deprotection step on $V_1$/Y first before the reactive moiety RM can be introduced. This saves one synthetic step at a late-stage moment in the synthetic route compared with routes described in the prior art;

(b) as one less deprotectable protecting group is required on $V_1$/Y, optional other protecting groups that are necessary to protect functional groups in the one or more moieties $V_1$, Y, and Z during the preparation of a compound of formula (V) or (VI) can be chosen from a substantially larger pool of suitable protecting groups compared to the situation in the prior art when deprotection of a protecting group on $V_1$/Y had to occur. This is because they do not longer need to be resistant to the conditions required to deprotect said protecting group on $V_1$/Y.

(c) compared to a synthetic route in which the reactive moiety RM to react with $V_2$ is introduced in the beginning of the route (if possible at all), the strategy in this invention is preferred as only a single synthetic route needs to be designed to easily synthesize any compound of formula (III) or (IV) for a given $V_1$, Y, Z, and z, whereas a new route may have to be developed following the former methodology for each different reactive moiety RM.

(d) the one or more $V_1$, Y, and Z moieties may be completely deprotected (except for the azide-$L_1$ or alkyne-$L_1$ protecting group) before the reactive moiety RM and the $V_2$ moiety are introduced, which may (further) enlarge the pool of suitable protecting groups that can be used.

It should be noted that the method of this invention is distinct and preferred over a method wherein $V_2$ is first reacted with a second compound as described above before coupling to a first compound as described above because the method of this invention requires less synthetic steps when multiple conjugates with different $V_2$ moieties are required. Furthermore, when $V_2$ is a complex, large, and/or relatively difficult-to-handle moiety, e.g., a biomolecule such as a protein or an antibody, only a single reaction step has to be carried out in which $V_2$ is involved according to the present invention. In addition, when $V_2$ carries multiple groups to which coupling should occur, less diverse mixtures are likely to be formed using the method of the present invention compared to a method in which two consecutive steps with $V_2$ are used to form a compound of formula (I) or (II) due to incomplete conversion, which may readily occur in such reactions.

Thus, when $V_1$, Y, and/or Z contain for example additional functional groups (that need to be protected during the synthetic route), the method of this invention is beneficial over methods known in the art. The presence of additional functional groups, for example (unprotected) polar groups, e.g., an amino group (from for example a lysine residue), a hydroxyl group, or a carboxylate group, may be advantageous. By way of illustration, incorporation in $V_1$ of amino acids with functional groups in the side chains may for example improve the (pharmacokinetic) properties of the compound, improve its water solubility, and/or advantageously affect its aggregation behavior.

Compounds (I) and (II) of this invention are improved over compounds of the prior art due to the presence of the 1,2,3-triazole moiety. Due to its polarity, this moiety may contribute to increased water solubility, decreased aggregation, and improved pharmacokinetic properties of the conjugate, and at the same time the 1,4-substituted ring makes the linker more rigid and may keep it in a more extended form, thus keeping $V_2$ further away from the optional site of transformation or cleavage, which may favorably affect the release of Z, and keeping the one or more Z moieties further away from $V_2$, which may reduce shielding of $V_2$ and/or reduce blocking of $V_2$'s functionality.

DESCRIPTION OF THE INVENTION

Figure 1:
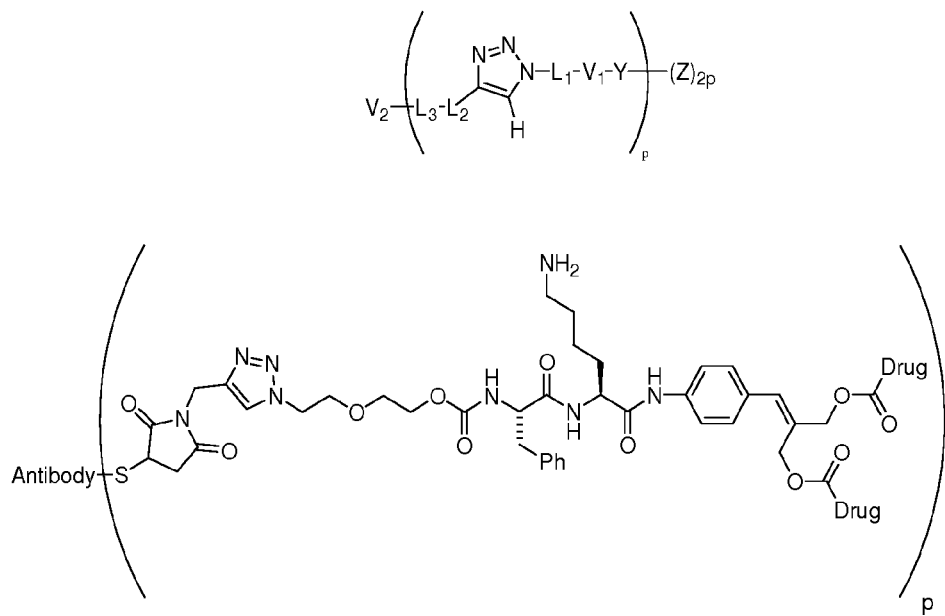
FIG. 1 depicts an exemplary structural drawing of a compound of the invention.
Figure 2:
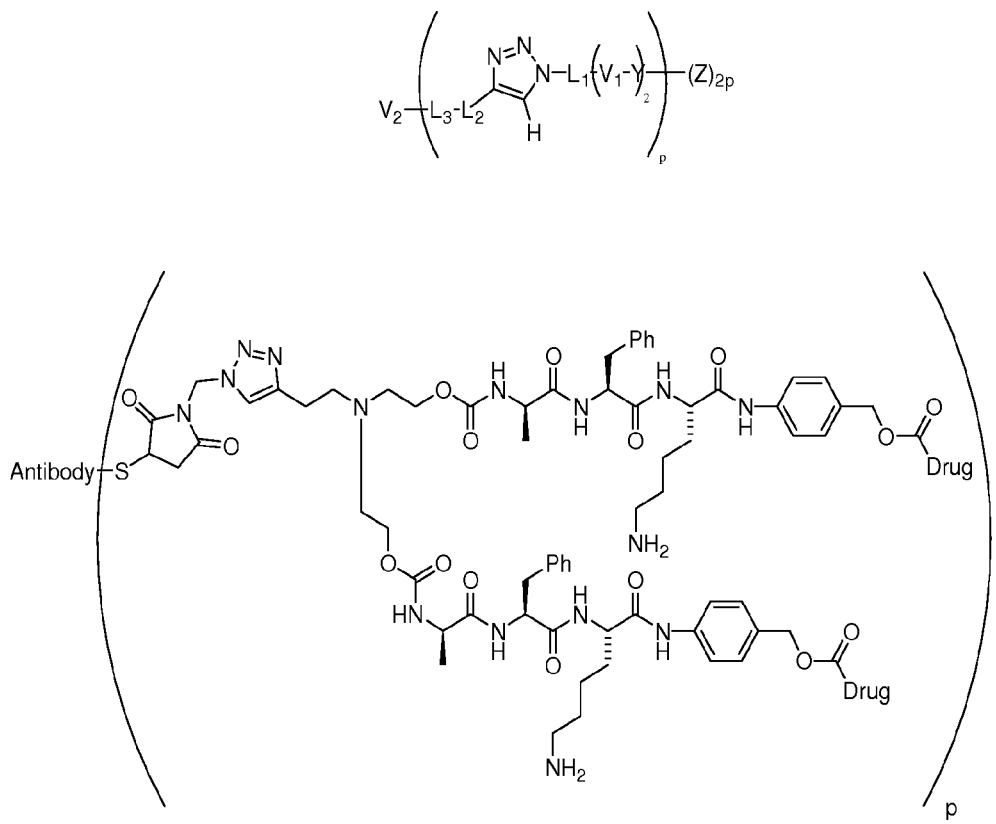
FIG. 2 depicts another exemplary structural drawing of a compound of the invention.
Figure 3:
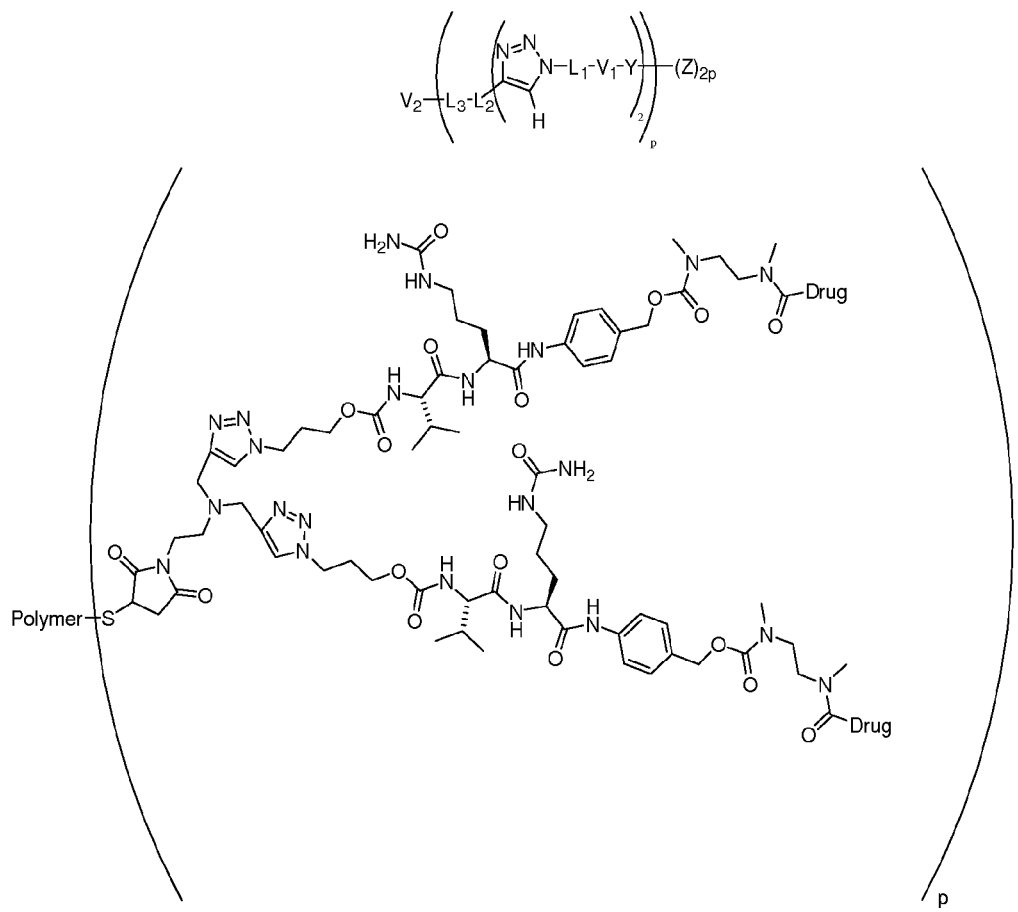
FIG. 3 depicts another exemplary structural drawing of a compound of the invention.
Figure 4:
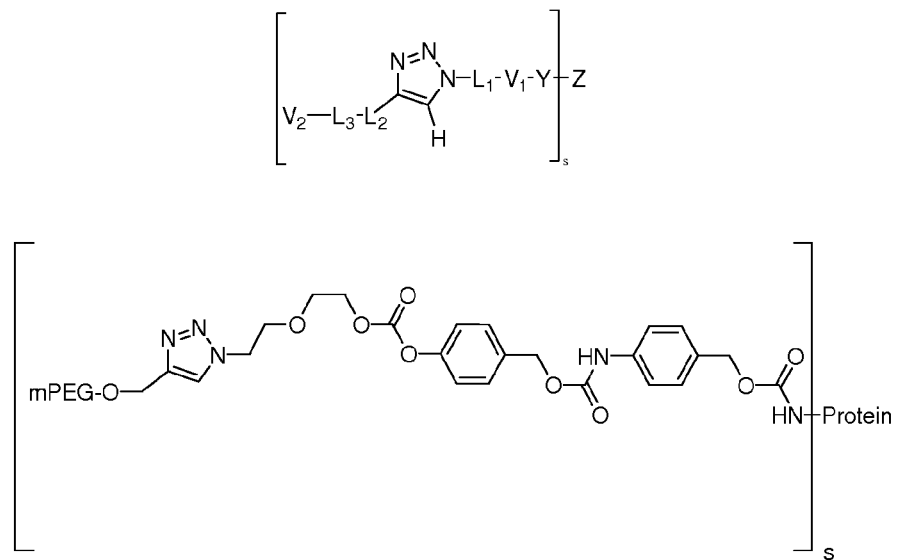
FIG. 4 depicts another exemplary structural drawing of a compound of the invention.
Figure 5:
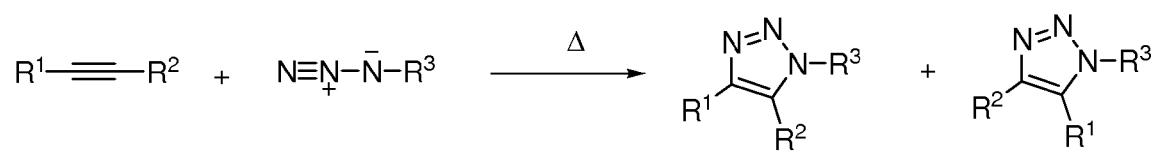
FIG. 5 depicts a schematic representation of the Huisgen cycloaddition between an alkyne and an azide.
Figure 6:
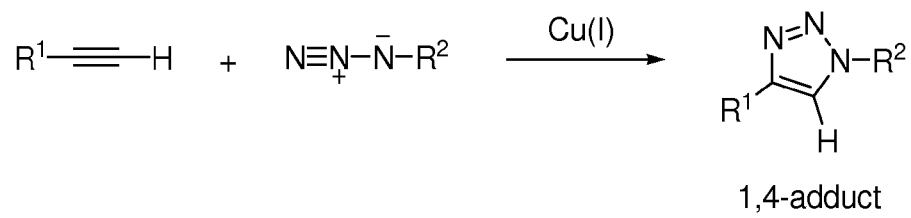
FIG. 6 depicts a schematic representation of the Cu(I)-catalyzed cycloaddition of a terminal alkyne with an azide.

The following detailed description is provided so that the invention may be more fully understood.

Definitions

The term "antibody", as used herein, refers to a full length immunoglobulin molecule, an immunologically active portion of a full-length immunoglobulin molecule, or a derivative of a full length immunoglobulin molecule or an active portion thereof, i.e., a molecule that contains an antigen-binding site that immunospecifically binds an antigen of a target of interest or part thereof, such targets including, but not limited to, cancer cells. The immunoglobulin disclosed herein can be of any type (e.g., IgG, IgE, IgM, IgD, IgA, and IgY), class (e.g., IgG1, IgG2, IgG3, IgG4, IgA1, and IgA2), or subclass of immunoglobulin molecule. The immunoglobulin can be derived from any species, but preferably, it is of human, murine, or rabbit origin. Antibodies useful in the invention include, but are not limited to, monoclonal, polyclonal, bispecific, human, humanized, or chimeric antibodies, single chain antibodies, Fv fragments, Fab fragments, F(ab') fragments, F(ab')$_2$ fragments, fragments produced by a Fab expression library, anti-idiotypic antibodies, CDRs, and epitope-binding fragments of any of the above which immunospecifically bind to an antigen-of-interest.

The term "leaving group" refers to a group that can be substituted by another group. Such leaving groups are well-known in the art, and examples include, but are not limited to, a halide (fluoride, chloride, bromide, iodide), a sulfonate (e.g., methanesulfonate, p-toluenesulfonate, and trifluoromethanesulfonate), succinimide-N-oxide, p-nitrophenoxide, pentafluorophenoxide, tetrafluorophenoxide, a carboxylate, and an alkoxycarboxylate.

The term "protecting group" refers to a group that temporarily protects or blocks, i.e., intendedly prevents from reacting, a functional group, e.g., an amino group, a hydroxyl group, or a carboxyl group, during the transformation of a first molecule to a second molecule. This transformation occurs in three or more steps, the first step being protection of said functional group with said protecting group in said first molecule, the last step being removal of said protecting group from said functional group to give said second molecule, and the one or more other steps occurring between first and last steps at a distant site or distant sites in the molecule(s).

The term "water-soluble group" refers to a functional group that is well solvated in aqueous environments and that imparts improved water solubility to a compound to which it is attached. Examples of water-soluble groups include, but are not limited to, alcohols and polyalcohols, straight chain or cyclic saccharides, primary, secondary, tertiary, or quaternary amines and polyamines, sulfate groups, carboxylate groups, phosphate groups, phosphonate groups, ascorbate groups, glycols, including polyethylene glycols, and polyethers.

The term "substituted", when used as adjective to "alkyl", "heteroalkyl", "cycloalkyl", "heterocycloalkyl", "aryl", "heteroaryl", and the like, indicates that said "alkyl", "heteroalkyl", "cycloalkyl", "heterocycloalkyl", "aryl", or "heteroaryl" group contains one or more substituents, which include, but are not limited to, OH, =O, =$NR^h$, =N—$OR^h$, SH, $NH_2$, $NO_2$, $N_3$, $CF_3$, CN, OCN, SCN, NCO, NCS, C(O)$NH_2$, C(O)H, C(O)OH, halogen, $R^h$, $SR^h$, $S(O)R^h$, $S(O)OR^h$, $S(O)_2R^h$, $S(O)_2OR^h$, $OP(O)(OR^h)(OR^i)$, $P(O)(OR^h)(OR^i)$, $OR^h$, $NHR^i$, $N(R^h)R^i$, $^+N(R^h)(R^i)R^j$, $Si(R^h)(R^i)(R^j)$, $C(O)R^h$, $C(O)OR^h$, $C(O)N(R^i)R^h$, $OC(O)R^h$, $OC(O)OR^h$, $OC(O)N(R^h)R^i$, $N(R^i)C(O)R^h$, $N(R^i)C(O)OR^h$, $N(R^i)C(O)N(R^j)R^h$, wherein $R^h$, $R^i$, and $R^j$ are independently selected from H and optionally substituted $C_{1-15}$ alkyl, $C_{1-15}$ heteroalkyl, $C_{3-15}$ cycloalkyl, $C_{3-15}$ heterocycloalkyl, and $C_{4-15}$ aryl and $C_{4-15}$ heteroaryl or a combination thereof, two or more of $R^h$, $R^i$, and $R^j$ optionally being joined to form one or more carbocycles or heterocycles.

The term "aryl" as used herein refers to a carbocyclic aromatic substituent, which may consist of 1 or more rings fused together. Examples of aryl groups include, but are not limited to, phenyl, naphthyl, and anthracenyl.

The term "heteroaryl" as used herein refers to a carbocyclic aromatic substituent, which may consist of 1 or more rings fused together and wherein at least one carbon in one of the rings is replaced by a heteroatom. Examples of heteroaryl groups include, but are not limited to, pyridinyl, furanyl, pyrrolyl, triazolyl, imidazolyl, thiophenyl, indolyl, benzofuranyl, and quinolinyl.

The term "alkyl" as used herein refers to a straight chain or branched, saturated or unsaturated hydrocarbon substituent. Examples of alkyl groups include, but are not limited to, methyl, ethyl, propyl, butyl, pentyl, hexyl, octyl, decyl, isopropyl, sec-butyl, isobutyl, tert-butyl, isopentyl, 2-methylbutyl, vinyl, allyl, 1-butenyl, 2-butenyl, isobutylenyl, 1-pentenyl, and 2-pentenyl.

The term "heteroalkyl" as used herein refers to a straight chain or branched, saturated or unsaturated hydrocarbon substituent in which at least one carbon is replaced by a heteroatom. Examples include, but are not limited to, methyloxymethyl, ethyloxymethyl, methyloxyethyl, ethyloxyethyl, methylaminomethyl, dimethylaminomethyl, methylaminoethyl, dimethylaminoethyl, methylthiomethyl, ethylthiomethyl, ethylthioethyl, and methylthioethyl.

The term "cycloalkyl" as used herein refers to a saturated or unsaturated non-aromatic carbocycle substituent, which may consist of 1 or more rings fused together. Examples include, but are not limited to, cyclopropyl, cyclobutyl, cyclopentyl, cyclopentenyl, cyclopentadienyl, cyclohexyl, cyclohexenyl, 1,3-cyclohexadienyl, and 1,4-cyclohexadienyl.

The term "heterocycloalkyl" as used herein refers to a non-aromatic cyclic hydrocarbon substituent which may consist of 1 or more rings fused together and wherein at least one carbon in one of the rings is replaced by a heteroatom. Examples include, but are not limited to, tetrahydrofuranyl, pyrrolidinyl, piperidinyl, 1,4-dioxanyl, piperazinyl, and morpholinyl.

The extension "-ylene" as opposed to "-yl" in for example "alkylene" as opposed to "alkyl" indicates that said for example "alkylene" is a multivalent moiety connected to one or more other moieties via two or more covalent single bonds or one or more double bonds or one or more triple bonds as opposed to being a monovalent group connected to one moiety via one covalent single bond in said for example "alkyl". The term "alkylene" therefore refers to a straight chain or branched, saturated or unsaturated hydrocarbon moiety; the term "heteroalkylene" as used herein refers to a straight chain or branched, saturated or unsaturated hydrocarbon moiety in which at least one carbon is replaced by a heteroatom; the term "arylene" as used herein refers to a carbocyclic aromatic moiety, which may consist of 1 or more rings fused together; the term "heteroarylene" as used herein refers to a carbocyclic aromatic moiety, which may consist of 1 or more rings fused together and wherein at least one carbon in one of the rings is replaced by a heteroatom; the term "cycloalkylene" as used herein refers to a saturated or unsaturated non-aromatic carbocycle moiety, which may consist of 1 or more rings fused together; the term "heterocycloalkylene" as used herein refers to a non-aromatic cyclic hydrocarbon moiety which may consist of 1 or more rings fused together and wherein at least one carbon in one of the rings is replaced by a heteroatom. Exemplary multivalent moieties include those examples given for the monovalent groups hereinabove in which one or more hydrogen atoms are removed.

The prefix "poly" in "polyalkylene", "polyheteroalkylene", "polyarylene", "polyheteroarylene", polycycloalkylene", "polyheterocycloalkylene", and the like, indicates that two or more of such "-ylene" moieties, e.g., alkylene moieties, are joined together to form a branched or unbranched multivalent moiety containing two or more attachment sites for adjacent moieties.

Certain compounds of the invention possess chiral centers or double bonds; the enantiomeric, diastereomeric, and geometric mixtures of two or more isomers, in any composition, as well as the individual isomers are encompassed within the scope of the present invention.

The compounds of the invention may also contain unnatural proportions of atomic isotopes at one or more atoms that constitute such compounds. All isotopic variations of the compounds of this invention, whether radioactive or not, are intended to be encompassed within the scope of this invention.

The phrase "pharmaceutically active salt" as used herein, refers to pharmaceutically acceptable organic or inorganic salts of compounds of the invention. For compounds containing one or more basic groups, e.g., an amine group, acid addition salts can be formed. For compounds containing one or more acidic groups, e.g., a carboxylic acid group, base addition salts can be formed. For compounds containing both acidic and basic groups, zwitterions may be obtained as salts. Instances where multiple charged atoms are part of the pharmaceutically acceptable salt can have multiple counterions.

The phrase "pharmaceutically acceptable solvate" refers to an association of one or more solvent molecules and a compound of the invention. Examples of solvents that form pharmaceutically acceptable solvates include, but are not limited to, water, isopropyl alcohol, ethanol, methanol, DMSO, ethyl acetate, and acetic acid.

The term "conjugate" hereinbelow refers to a compound of formula (I) or (II).

The term "linker-agent conjugate" herein refers to a compound of any of formulae (III) to (VI).

The terms "adjuvant moiety" and "functional moiety" herein refer to moieties that, being part of a compound of this invention, add additional functionality to and/or improve one or more properties of said compound.

The term "reactive moiety" herein refers to a moiety that can be coupled with another moiety without prior activation or transformation.

The term "targeting moiety" refers to any molecule that specifically binds or reactively associates or complexes with a moiety specifically or in relative excess present at or near the target site, on, in, or near the target cell, or in (the proximity of) the target tissue or organ, e.g., a receptor, substrate, antigenic determinant, or other receptive moiety, or that can target the conjugate to the target site via other mechanisms by virtue of its nature, e.g., through the EPR effect. Examples of a targeting moiety include, but are not limited to, an antibody or antibody fragment, a polymer, a dendrimer, a biologic response modifier, an enzyme, a vitamin, a growth factor, a steroid, a carrier protein, and a hormone, or any combination thereof.

The phrase "moiety that improves the pharmacokinetic properties of the compound" refers to a moiety that changes the pharmacokinetic properties of the one or more moieties Z in such a way that a better therapeutic or diagnostic effect can be obtained. The moiety can for example increase the water solubility, increase the circulation time, or reduce immunogenicity.

The phrase "linking group" refers to a structural element of a compound that links one structural element of said compound to one or more other structural elements of said same compound.

The phrase "a number representing degree of branching" is used to denote that the subscript number next to a closing bracket represents how many units of the moiety within the brackets are attached to the moiety directly to the left of the corresponding opening bracket. For example, A-(B)$_b$ with b being a number representing a degree of branching means that b units B are all directly attached to A. This means that when b is 2, the formula reduces to B-A-B.

The phrase "a number representing degree of polymerization" is used to denote that the subscript number next to a closing bracket represents how many units of the moiety within the brackets are connected to each other. For example, A-(B)$_b$ with b being a number representing a degree of polymerization means that when b is 2, the formula reduces to A-B-B.

In the generic structures throughout this description and in the claims letters are used to define structural elements. Some of these letters can be mistaken to represent an atom, such as C, N, O, P, K, B, F, S, U, V, W, I, and Y. To avoid confusion whenever these letters do not represent an atom they are given in bold typeface.

Throughout this description and in the claims molecular structures or parts thereof are drawn. As usual in such drawings bonds between atoms are represented by lines, in some cases, to indicate stereochemistry, by bold or broken or wedged lines. Usually a line ending in space (a "loose" end), i.e., at one end not having another line or specific atom connected to it, represents a CH$_3$ group. This is correct for the drawings representing the preferred compounds according to the invention hereinbelow. For those structures representing a structural element of the compounds according to the invention a line ending in space indicates the position of attachment of another structural element of the compound or conjugate. This has been indicated with a wavy line perpendicular to and crossing the "loose" line in most drawings.

Furthermore, the structures or parts thereof have been drawn, under the assumption that the structures are read from left to right, meaning that $V_2$ is always located on the left side (when present) and Z is always located on the right side of such structures.

According to the invention, self-elimination spacers that are able to release only a single moiety are called 'single release spacers'. Self-elimination spacers that are able to release two or more moieties are called 'multiple release spacers'.

Spacers, either branched or unbranched, which self-eliminate through a 1, 2+2n-elimination ($n \geq 1$) are further called 'electronic cascade' spacers.

Spacers that eliminate through a cyclization process under formation of a cyclic ureum derivative are called 'ω-amino aminocarbonyl cyclization spacers'.

When a self-elimination spacer is connected to one or more other self-elimination spacers via a direct bond, this combination of spacers is referred to as 'spacer system'. Herein, a single self-elimination spacer may also be referred to as a spacer system. A spacer system may be branched or unbranched and contain one or more attachment sites for Z as well as $V_1$.

In this document and in its claims, the verb "to comprise" and its conjugations is used in its non-limiting sense to mean that items following the word are included, but items non-specifically mentioned are not excluded.

As used in this specification and the appended claims, the singular forms "a", "an", and "the" include plural referents unless the content clearly dictates otherwise.

The following abbreviations are used herein and have the indicated definitions: AEC=2-azidoethoxycarbonyl; Ala=alanine; Aloc=allyloxycarbonyl; Boc=tert-butyloxycarbonyl; Cit: citrulline; DCC=N,N'-dicyclohexylcarbodiimide; DMF=N,N-dimethylformamide; Dox=doxorubicin; Fmoc=9-fluorenylmethyloxycarbonyl; HOBt=1-hydroxybenzotriazole; HOSu=N-hydroxysuccinimide; Lys=lysine; PABA=p-aminobenzyl alcohol; PABC=p-aminobenzyloxycarbonyl; Phe=phenylalanine; PNP=p-nitrophenoxide; THF: tetrahydrofuran; Val: valine.

Linker-Agent Conjugates and Conjugates

The present invention provides novel conjugates that are comprised of one or more functional moieties, one or more triazole-containing linkers, and one or more therapeutic or diagnostic moieties. Furthermore, the invention relates to corresponding linker-agent conjugates.

The conjugates of the present invention are in one aspect deemed to be applicable to target agents, i.e., therapeutic or diagnostic moieties, that need to be delivered at a specific target site where the conjugate can be converted into one or more agents or be induced to be converted into one or more of said agents. This invention can furthermore find application in (non-specific) controlled release of therapeutic or diagnostic moieties Z, with the aim of enhancing pharmacokinetic properties of said moieties.

A compound of the invention can be applied to target anticancer agents, but also antibiotics can be incorporated as Z moieties with the compound of the invention for example being activated by bacterial enzymes. As a further example, anti-viral, antimicrobial, anti-autoimmune disease, or anti-inflammatory agents may be incorporated.

In another aspect, this invention can find application in an in vivo or ex vivo diagnostic assay process. For example, an enzyme can be detected by a compound of this invention, which is selectively activated by said enzyme to release one or more diagnostic moieties.

Through sophisticated synthesis, compounds of the invention may be prepared that contain two or more different Z moieties. This may be interesting when it is considered that combination therapy emerges as a clinically important mode of treatment for diseases such as cancer, microbial diseases, and HIV.

In one aspect, the invention provides a compound of the formula

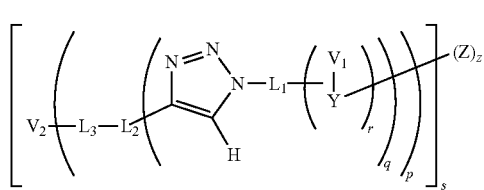

or a pharmaceutically acceptable salt or solvate thereof, wherein

Each $V_2$ is independently a functional moiety;

Each $L_3$ is independently either a bond or a linking group linking $V_2$ to $L_2$;

Each $L_2$ is independently either a bond or a linking group linking $L_3$ to one or more triazole groups;

Each $L_1$ is independently either a bond or a linking group linking the triazole group to one or more V, and/or Y;

Each $V_1$ is independently a non-cleavable moiety or a conditionally-cleavable moiety, optionally following prior conditional transformation, which can be cleaved or transformed by a chemical, photochemical, physical, biological, or enzymatic process, cleavage of $V_1$ ultimately leading to release of one or more Z moieties;

Each Y is independently absent or a self-eliminating spacer system which is comprised of 1 or more self-elimination spacers;

Each Z is independently H, OH, a leaving group, or a therapeutic or diagnostic moiety, provided that at least one Z is a therapeutic or diagnostic moiety, and each Z is directly coupled to either Y or $V_1$ when Y is absent;

p, q, r, and s are numbers representing degree of branching and are each independently a positive integer;

z is an integer equal to or smaller than the total number of attachment sites for Z in the one or more $V_1$—Y moieties.

In another aspect, the invention provides a compound of the formula

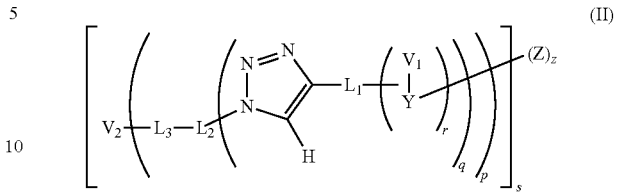

or a pharmaceutically acceptable salt or solvate thereof, wherein $V_2$, $L_3$, $L_1$, $L_2$, $V_1$, Y, Z, z, p, q, r, and s are as defined above for compound (I).

In order to clarify the above-mentioned formulae, some simplified examples of formula (I) are described in some further detail hereinbelow.

When in the formula of compound (I), r, q, and s all equal 1 and $L_1$ is connected to $V_1$, the formula reduces to

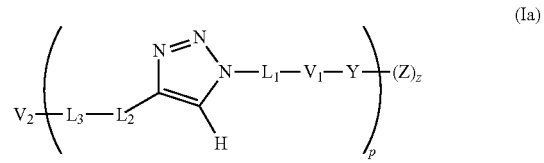

and represents a conjugate wherein p moieties $L_3$-$L_2$-triazole-$L_1$-$V_1$—Y-$(Z)_{z/p}$ are connected to $V_2$ via multiple functional groups on $V_2$. A number of z moieties Z are connected to the one or more $V_1$—Y moieties. An example of such a conjugate is a compound wherein an antibody or a polymer is used as a $V_2$ moiety to which p moieties $L_3$-$L_2$-triazole-$L_1$-$V_1$—Y are connected and z moieties Z are connected to the one or more $V_1$—Y moieties. If each $V_1$—Y contains only one attachment site for Z and each Z is only coupled via one functional group, then z equals p.

When in the formula of compound (I), p, q, z, and r equal 1 and $L_1$ is connected to $V_1$, the formula reduces to

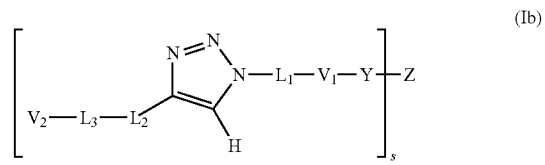

and represents a conjugate wherein s moieties $V_2$-$L_3$-$L_2$-triazole-$L_1$-$V_1$—Y are connected to a single Z. An example of such a conjugate is a compound wherein a therapeutic protein (Z) is functionalized with s PEG molecules ($V_2$ moieties) linked to said protein via $L_3$-$L_2$-triazole-$L_1$-$V_1$—Y. When one or more $V_1$—Y moieties contain multiple attachment sites for Z, this means that the corresponding $V_2$-$L_3$-$L_2$-triazole-$L_1$-$V_1$—Y moiety/moieties may be connected to the protein via more than one functional group on the protein. If all $V_1$—Y moieties contain a single attachment site for Z, s represents the number of functional groups on Z that are coupled to the $V_1$—Y moieties.

The formulae (I) and (II) are further clarified by the exemplary compounds drawn in FIGS. 1, 2, 3, and 4.

In another aspect, the invention provides a compound of the formula

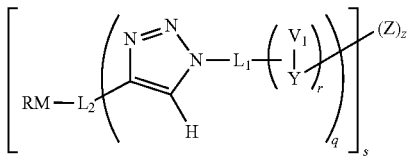
(III)

or a pharmaceutically acceptable salt or solvate thereof, wherein
Each RM is independently a reactive moiety;
$L_1, L_2, V_1, Y, Z, z, q, s$, and $r$ are as defined for compound (I) with the exception that $L_2$ is now linking RM to one or more triazole groups.

In yet another aspect, the invention provides a compound of the formula

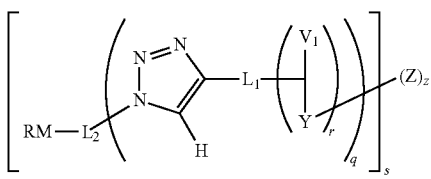
(IV)

or a pharmaceutically acceptable salt or solvate thereof, wherein
Each RM is independently a reactive moiety;
$L_1, L_2, V_1, Y, Z, z, q, s$, and $r$ are as defined for compound (I) with the exception that $L_2$ is now linking RM to one or more triazole groups.

In yet another aspect, the invention provides a compound of the formula

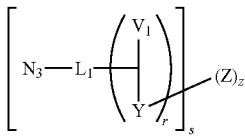
(V)

or a pharmaceutically acceptable salt or solvate thereof, wherein
$N_3$ is an azido group;
$L_1, V_1, Y, Z, r, s$, and $z$ are as defined for compound (I) with the exception that $L_1$ is now linking the azido group to one or more $V_1$ and/or Y moieties.

In yet another aspect, the invention provides a compound of the formula

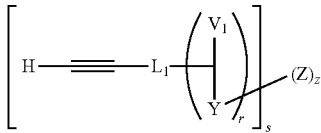
(VI)

or a pharmaceutically acceptable salt or solvate thereof, wherein
$L_1, V_1, Y, Z, r, s$, and $z$ are as defined for compound (I) with the exception that $L_1$ is now linking the acetylene group to one or more $V_1$ and/or Y moieties.

In each compound, each $L_1$ may be connected to $V_1$ and/or Y. Synthesis may be more straightforward when $L_1$ is connected to $V_1$ and the compound may be less prone to premature degradation. Connection of $L_1$ to Y may have the advantage that $V_1$ can be transformed and/or cleaved with more ease. Other advantages may for example be that (part of) Y remains bound to $L_1$ or that the compound displays improved (pharmacokinetic) properties, solubility, or aggregation behavior.

In one embodiment in the compounds of the invention p is an integer from 1 (included) to 1000 (included), q is an integer from 1 (included) to 128 (included), r is an integer from 1 (included) to 128 (included), and s is an integer from 1 (included) to 50 (included). In other embodiments in the compounds of the invention p is an integer from 1 (included) to 500 (included) or 400 (included) or 300 (included) or 200 (included) or 100 (included) or 16 (included) or 8 (included) or 6 (included) or 4 (included) or 2 (included), q is an integer from 1 (included) to 64 (included) or 32 (included) or 16 (included) or 8 (included) or 4 (included) or 2 (included), r is an integer from 1 (included) to 64 (included) or 32 (included) or 16 (included) or 8 (included) or 4 (included) or 2 (included), and s is an integer from 1 (included) to 40 (included) or 30 (included) or 20 (included) or less than 20 and any combination of the values given for p, q, r and s.

Compounds (III)-(VI) are preferably used as intermediates for the preparation of conjugates (I) and (II). Alternatively, compounds (III)-(IV) may be used directly with no further conversion to compounds (I) or (II). In the latter case, these compounds are to react in situ to form the final compound, not necessarily being a compound of formula (I) or (II). For example, a compound of formula (III) or (IV) may be used in a diagnostic assay in which it first has to be attached to a solid support via the reactive moiety. Alternatively, a compound of formula (III) or (IV) can be administered to a mammal and react in vivo with a reaction partner, for example albumin, to a compound of formula (I) or (II).

The $V_1$ Moiety

In the compounds of the invention, the $V_1$ moiety is a group that is either non-cleavable or conditionally cleavable, optionally after prior conditional transformation. In the latter case, it is designed to be transformed and/or cleaved from Y, or Z when Y is absent, by a chemical, photochemical, physical, biological, or enzymatic process upon being brought in or under a certain condition. This condition may for example be bringing a compound of the invention in an aqueous environment, which leads to hydrolysis of $V_1$, or bringing a compound of the invention in an environment that contains an enzyme that recognizes and cleaves $V_1$, or bringing a compound of the invention under reducing conditions, which leads to reduction of $V_1$, or bringing a compound of the invention in contact with radiation, e.g., UV light, which leads to transformation and/or cleavage, or bringing a compound of the invention in contact with heat, which leads to transformation and/or cleavage, or bringing a compound of the invention under reduced pressure, which leads to transformation, e.g., a retrocycloaddition, and/or cleavage, or bringing a compound of the invention under elevated or high pressure, which leads to transformation and/or cleavage. This condition may further be met after administrating a compound of this invention to an animal, e.g., a mammal: the condition may be met when the compound localizes to for example a specific organ, tissue, cell, subcellular target, or microbial target, for example by the presence of internal factors (e.g., target-specific enzymes or hypoxia) or application of external factors (e.g., radiation, magnetic fields) or the condition may already be met directly upon administration (e.g., ubiquitous enzymes).

In general, transformation of $V_1$ will directly or indirectly lead to cleavage of $V_1$ from Y, or Z when Y is absent. It may occur that two or more separate transformations and/or cleavages, requiring the same or different conditions, are required in order to cleave $V_1$ completely from Y or Z. In this way, increased selectivity may be obtained.

A compound of this invention may contain more than one $V_1$ moiety. These $V_1$ moieties may or may not be the same and may or may not require the same conditions for transformation and/or cleavage.

In one aspect of this invention, a compound of the invention is used to target one or more therapeutic and/or diagnostic moieties Z to target cells. In this instance, $V_1$ may for example contain a substrate molecule that is cleaved by an enzyme present in the vicinity of the target cells or inside the target cells, for example tumor cells. $V_1$ can for example contain a substrate that is cleaved by an enzyme present at elevated levels in the vicinity of or inside the target cells as compared to other parts of the body, or by an enzyme that is present only in the vicinity of or inside the target cells. It is important to recognize that if target cell specificity is achieved solely based upon the selective transformation and/or cleavage of $V_1$ at the target site, the condition (eventually) causing the cleavage should preferably, at least to a certain degree, be target cell-specific, whereas the presence of another target-specific moiety in the compound of the invention, for instance in $V_2$, reduces or takes away this requirement. For example, when $V_2$ causes specific internalization into a target cell, an enzyme also present in other cells may transform and/or cleave $V_1$. In one embodiment, transformation and/or cleavage of $V_1$ occurs intracellularly. In another embodiment, transformation and/or cleavage of $V_1$ occurs extracellularly.

In one embodiment, the $V_1$ moiety is a conditionally cleavable moiety.

In one embodiment, $V_1$ contains a di-, tri-, tetra-, or oligopeptide which consists of an amino acid sequence recognized by a protease, for example plasmin, a cathepsin, cathepsin B, prostate-specific antigen (PSA), urokinase-type plasminogen activator (u-PA), or a member of the family of matrix metalloproteinases, present in the vicinity of or inside the target cells, for example tumor cells.

In one embodiment the invention relates to a conjugate wherein $V_1$ is a dipeptide, tripeptide, tetrapeptide, or oligopeptide moiety comprised of natural L amino acids, unnatural D amino acids, or synthetic amino acids, or a peptidomimetic, or any combination thereof.

In one embodiment, $V_1$ is a peptide. In another embodiment, $V_1$ is a dipeptide. In another embodiment, $V_1$ is a tripeptide. In another embodiment, $V_1$ is a tetrapeptide. In yet another embodiment, $V_1$ is a peptidomimetic.

In one embodiment, $V_1$ contains a substrate for an enzyme.

In another embodiment, $V_1$ contains a β-glucuronide that is recognized by β-glucuronidase present in the vicinity of or inside tumor cells.

In one embodiment, $V_1$ contains a substrate for an extracellular enzyme.

In another embodiment, $V_1$ contains a substrate for an intracellular enzyme.

In yet another embodiment, $V_1$ contains a substrate for a lysosomal enzyme.

In yet another embodiment, $V_1$ contains a substrate for the serine protease plasmin.

In yet another embodiment, $V_1$ contains a substrate for one or more of the cathepsins, for example cathepsin B.

When $V_1$ is cleaved extracellularly, the one or more Z moieties may be released extracellularly. This may provide the advantage that these Z moieties are not only able to affect or detect the cell(s) directly surrounding the site of activation, but also cells somewhat further away from the site of activation due to diffusion (bystander effect).

An enzyme can also be transported to the vicinity of or inside target cells or target tissue via for example antibody-directed enzyme prodrug therapy (ADEPT), polymer-directed enzyme prodrug therapy (PDEPT) or macromolecular-directed enzyme prodrug therapy (MDEPT), virus-directed enzyme prodrug therapy (VDEPT), or gene-directed enzyme prodrug therapy (GDEPT).

In again another embodiment $V_1$ contains a nitro(hetero)aromatic moiety that can be transformed and/or cleaved by reduction under hypoxic conditions or by reduction by a nitroreductase. After reduction of the nitro group and cleavage of the resulting moiety, elimination of the spacer system Y, if present, leads to release of the one or more moieties Z.

In one embodiment the invention relates to a compound wherein $V_1$ comprises a tripeptide. The tripeptide may be linked via its C-terminus to Y. In one embodiment, the C-terminal amino acid residue of the tripeptide is selected from arginine, citrulline, and lysine, the middle amino acid residue of the tripeptide is selected from alanine, valine, leucine, isoleucine, methionine, phenylalanine, cyclohexylglycine, tryptophan and proline, and the N-terminal amino acid residue of the tripeptide is selected from any natural or unnatural amino acid.

In another embodiment the invention relates to a compound wherein $V_1$ comprises a dipeptide. The dipeptide may be linked via its C-terminus to Y. In one embodiment, the C-terminal amino acid residue of the dipeptide is selected from alanine, arginine, citrulline, and lysine, and the N-terminal amino acid residue of the dipeptide is selected from any natural or unnatural amino acid.

In a further embodiment $V_1$ is selected from D-alanylphenylalanyllysine, D-valylleucyllysine, D-alanylleucyllysine, D-valylphenylalanyllysine, D-valyltryptophanyllysine, D-alanyltryptophanyllysine, alanylphenylalanyllysine, valylleucyllysine, alanylleucyllysine, valylphenylalanyllysine, valyltryptophanyllysine, alanyltryptophanyllysine, D-alanylphenylalanylcitrulline, D-valylleucylcitrulline, D-alanylleucylcitrulline, D-valylphenylalanylcitrulline, D-valyltryptophanylcitrulline, D-alanyltryptophanylcitrulline, alanylphenylalanylcitrulline, valylleucylcitrulline, alanylleucylcitrulline, valylphenylalanylcitrulline, valyltryptophanylcitrulline, and alanyltryptophanylcitrulline.

In yet another embodiment, $V_1$ is selected from phenylalanyllysine, valyllysine, D-phenylalanylphenylalanyllysine, phenylalanylphenylalanyllysine, glycylphenylalanyllysine, alanyllysine, valylcitrulline, phenylalanylcitrulline, isoleucylcitrulline, tryptophanyllysine, tryptophanylcitrulline, phenylalanylarginine, phenylalanylalanine, glycylphenylalanylleucylglycine (SEQ ID NO:1), alanylleucylalanylleucyl (SEQ ID NO:2), alanylarginylarginine, phenylalanyl-$N^9$-tosylarginine, phenylalanyl-$N^9$-nitroarginine, leucyllysine, leucylcitrulline, and phenylalanyl-O-benzoylthreonine.

In a further embodiment, $V_1$ is selected from phenylalanyllysine and valylcitrulline.

In another aspect of this invention, a compound of this invention is used to improve the pharmacokinetic properties of Z. $V_1$ may in this case for example be or contain a group that is cleaved by ubiquitous enzymes, e.g., esterases that are present in the circulation, by pH-controlled intramolecular cyclization, or by acid-catalyzed, base-catalyzed, or non-catalyzed hydrolysis, or $V_1$ may for example be or contain a disulfide. $V_1$ may therefore, optionally together with the connecting atom of $L_1$ and/or Y (or Z if Y is absent), for example form a carbonate, carbamate, ureum, ester, amide, imine, hydrazone, oxime, disulfide, acetal, or ketal group. This means that $V_1$ can for example also represent or contain —OC(O)—, —C(O)O—, —OC(O)O—, —OC(O)N($R^d$)—, —N($R^d$)C(O)—, —C(O)N($R^d$)—, —N($R^d$)C(O)O—, —N($R^d$)C(O)N($R^e$)—, —C(O)—, —OC($R^d$)($R^e$)—, —C($R^d$)($R^e$)O—, —OC($R^d$)($R^e$)O—, —C($R^d$)($R^e$)—, —S—, —S—S—, —C≡, ≡C—, —N≡, ≡N—, —C=N—, —N=C—, —O—N=, =N—O—, —C=N—O—, —O—N=C—, —N($R^f$)—N=, =N—N($R^f$)—, —N($R^f$)—N=C—, or —C=N—N($R^f$)—, wherein $R^c$, $R^e$, and $R^f$ independently represent H, or optionally substituted $C_{1-10}$ alkyl or aryl and wherein two or more of $R^d$, $R^e$, and $R^f$ may be joined to form one or more optionally substituted aliphatic or aromatic carbocycles or heterocycles.

It is understood that $V_1$ can also be or contain such a moiety and/or be transformed and/or cleaved in the same or a similar way when a compound of this invention is used for other purposes than solely improving the pharmacokinetic properties of Z.

When the compounds of the invention are used for other purposes, e.g., an ex vivo diagnostic assay, $V_1$ may be or contain any of the moieties mentioned above and transformation and/or cleavage of $V_1$ may occur by any one of the processes mentioned above or by any other functional transformation or cleavage process known to a person skilled in the art. For example, in a diagnostic assay, $V_1$ may be cleaved or transformed by an enzyme, by reduction, or below, above, or at a certain pH.

When $V_1$ is conditionally cleavable, the compounds of this invention are designed to eventually release at least one Z after cleavage and optional prior transformation of $V_1$. Release of Z from a compound of this invention via another mechanism is however not excluded from this invention.

It should be noted that if Y is absent, $V_1$ is always connected to both $L_1$ and Z. It should further be noted that $V_1$, if $L_1$ is connected to Y, may contain a blocking group at the end not connected to Y. This blocking group serves to prevent premature transformation and/or cleavage of $V_1$ from Y before the condition is met under which $V_1$ is designed to be transformed and/or cleaved. For example, when the α-amino group of the N-terminal amino acid of $V_1$ is not coupled to $L_1$, this amino acid may be functionalized with a suitable blocking group coupled to the α-amino group or may be an unnatural amino acid, e.g., a D amino acid, such that undesired premature (step-by-step) degradation of $V_1$ by for example ubiquitous enzymes or exopeptidases is prevented.

When $V_1$ is not connected to $L_1$, $V_1$ may for example be selected from $R^o$—[O($R''$O)P(O)]$_{pp}$—, $R^o$—C(O)—, $R^o$—OC(O)—, and $R^o$—N($R''$)C(O)— wherein pp is selected from 1 to 3, each $R^o$ and $R''$ are independently selected from H and optionally substituted $C_{1-15}$ alkyl, $C_{1-15}$ heteroalkyl, $C_{1-15}$ cycloalkyl, $C_{1-15}$ heterocycloalkyl, $C_{4-15}$ aryl, and $C_{4-15}$ heteroaryl and wherein $R^o$ and $R''$ may optionally be joined to form an optionally substituted carbocycle or heterocycle.

In one embodiment, $V_1$ is selected from phosphono, phenylaminocarbonyl, 4-(piperidino)piperidinocarbonyl, piperazinocarbonyl, and 4-methylpiperazinocarbonyl.

In another aspect of this invention, $V_1$ is a moiety that is non-cleavable. This means that $V_1$ cannot be cleaved from Y, or Z when Y is absent, under the conditions the compound containing such a $V_1$ moiety is designed to be applied, meaning that Z cannot be released in this way. Release of Z from a compound of this invention via another mechanism is however not excluded from this invention. When $V_1$ is a non-cleavable moiety, Y is preferably absent. A non-cleavable $V_1$ moiety may be any moiety that cannot be cleaved, or that can be cleaved only very slowly, under the conditions the compound containing such a $V_1$ moiety is designed to be applied, e.g. in vivo or in vitro. For example, when applied in vivo, $V_1$ will not or only very slowly be cleaved by enzymes present in the in vivo model used or by hydrolysis or as a consequence of other biological processes that may occur in said model. Such $V_1$ may therefore, optionally together with the connecting atom of $L_1$ and/or Z, for example, be a carbonyl group, an amide group, an ureum group, an ester group, a carbonate group, a carbamate group, or an optionally substituted methyleneoxy or methyleneamino group. $V_1$ may be preferred to be non-cleavable when it is not required that the one or more moieties Z are released. This may for example be the case when Z does not require to become released before it can exert its therapeutic or diagnostic properties.

In one embodiment, $V_1$ is connected to $L_1$ via one functional group.

In one embodiment $V_1$ is connected to $L_1$ via a functional group in the side chain of one of the natural or unnatural amino acids.

In another embodiment, the N-terminal amino acid of $V_1$ is connected via its amino group to $L_1$.

The Spacer System Y

The spacer system Y, when present, links $V_1$ and optionally $L_1$ to one or more moieties Z. In one embodiment, Y is absent. In another embodiment, Y is a self-elimination spacer system.

A spacer system Y may be incorporated in a compound of this invention to for example improve the properties of Z or the compound in general, to provide suitable coupling chemistries, or to create space between $V_1$ and Z.

A compound of this invention may contain more than one spacer system Y. These moieties Y may or may not be the same.

The spacer system Y is self-eliminating. This means that after cleavage or transformation of $V_1$, the left-hand side of Y becomes unblocked, which results in eventual release of one or more moieties Z. The self-elimination spacer systems may for example be those described in WO 02/083180 and WO 2004/043493, which are incorporated herein by reference in their entirety, as well as other self-elimination spacers known to a person skilled in the art.

In one aspect the invention is related to compounds wherein the spacer system Y is (W—)$_w$(X—)$_x$(A-)$_a$ (W—)$_w$(X—)$_n$C((A)$_a$-)$_c$ or

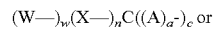

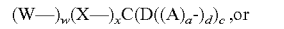

wherein
W and X are each a single release 1, 2+2n electronic cascade spacer (n≧1), being the same or different;
A is an ω-amino aminocarbonyl cyclization spacer;
C, D, E, and F are each a self-eliminating multiple release spacer or spacer system that upon activation can maximally release c, d, e, and f groups, respectively;
a is 0 or 1;
c, d, e, and f are numbers representing degree of branching;
w and x are numbers representing degree of polymerization;

c, d, e, and f are independently an integer from 2 (included) to 24 (included);

w and x are independently an integer from 0 (included) to 5 (included).

In a further aspect of the invention, the self-elimination multiple release spacers or spacer systems C, D, E, and F are independently selected from a compound having the formula

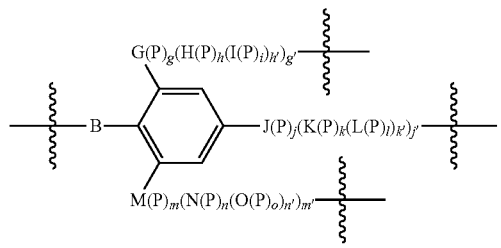

wherein

B is selected from $NR^1$, O, and S;

P is $C(R^2)(R^3)Q-(W-)_w(X-)_x$; wherein

Q has no meaning or is —O—CO—;

W and X are each a single release 1, 2+2n electronic cascade spacer ($n \geq 1$), being the same or different;

G, H, I, J, K, L, M, N, and O are independently selected from compounds having the formula:

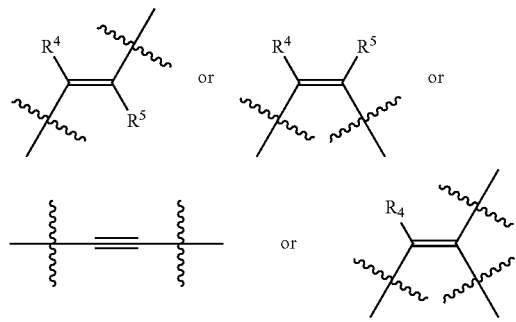

wherein $R^1$, $R^2$, $R^3$, $R^4$, and $R^5$ independently represent H, $C_{1-6}$ alkyl, $C_{3-20}$ heterocyclyl, $C_{5-20}$ aryl, $C_{1-6}$ alkoxy, hydroxy (OH), amino ($NH_2$), mono-substituted amino ($NR_xH$), di-substituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy ($S(=O)_2OH$), sulphonate ($S(=O)_2OR_x$), sulphonyl ($S(=O)_2R_x$), sulphixy ($S(=O)OH$), sulphinate ($S(=O)OR_x$), sulphinyl ($S(=O)R_x$), phosphonooxy ($OP(=O)(OH)_2$), and phosphate ($OP(=O)(OR_x)_2$), where $R_x$, $R_x^1$ and $R_x^2$ are independently selected from a $C_{1-6}$ alkyl group, a $C_{3-20}$ heterocyclyl group or a $C_{5-20}$ aryl group, two or more of the substituents $R^1$, $R^2$, $R^3$, $R^4$, and $R^5$ optionally being connected to one another to form one or more aliphatic or aromatic cyclic structures, or G, J, and M may also be selected from the group of P and hydrogen with the proviso that if two of G, J, and M are hydrogen, the remaining group must be

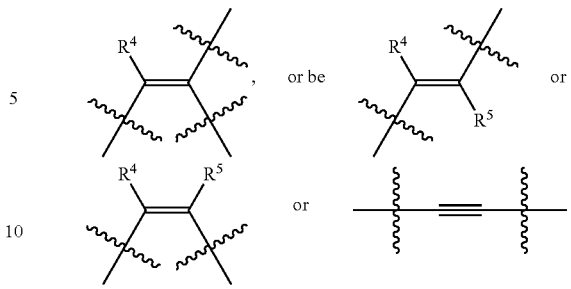

and at the same time be conjugated to

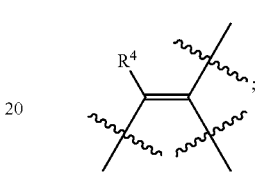

g, h, i, j, k, l, m, n, o, h', g', k', j', n', m' are numbers representing degree of branching and are independently 0, 1, or 2 with the provisos that if G=hydrogen or P, g, h, i, h', and g' all equal 0;
if J=hydrogen or P, j, k, l, k', and j' all equal 0;
if M=hydrogen or P, m, n, o, n', and m' all equal 0;
if G, H, I, J, K, L, M, N, or O is

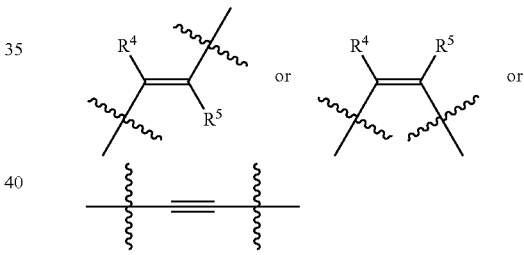

then g+g'=1, h+h'=1, i=1, j+j'=1, k+k'=1, l=1, m+m'=1, n+n'=1, or o=1, respectively;

if G, H, I, J, K, L, M, N, or O is

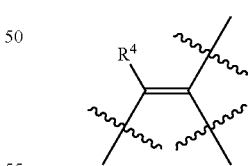

then g+g'=2, h+h'=2, i=2, j+j'=2, k+k'=2, l=2, m+m'=2, n+n'=2, or o=1, respectively;

if g'=0 and G is not hydrogen or P, then h, h', and i equal 0 and g>0;
if g=0 and G is not hydrogen or P, then g'>0;
if g'>0 and h'=0, then i=0 and h>0;
if g'>0 and h=0, then h'>0 and i>0;
if j'=0 and J is not hydrogen or P, then k, k', and l equal 0 and j>0;
if j=0 and J is not hydrogen or P, then j'>0;
if j'>0 and k'=0, then l=0 and k>0;

if j'>0 and k=0, then k'>0 and l>0;
if m'=0 and M is not hydrogen or P, then n, n', and o equal 0 and m>0;
if m=0 and M is not hydrogen or P, then m'>0;
if m'>0 and n'=0, then o=0 and n>0;
if m'>0 and n=0, then n'>0 and o>0;
w and x are numbers of polymerization and are independently an integer from 0 (included) to 5 (included).

According to a further embodiment of the invention, the 1, 2+2n electronic cascade spacers W and X are independently selected from a compound having the formula

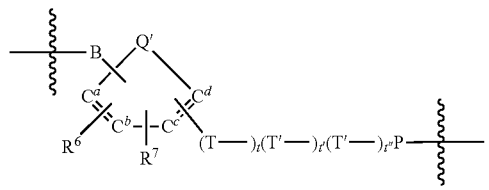

wherein
Q' is $R^{10}$—C=$CR^{11}$, S, O, $NR^{11}$, $R^{11}$C=N, or N=$CR^{11}$;
B is $NR^{12}$, O, or S;
P=C($R^5$)($R^9$)Q;
$R^6$, $R^7$, B, and (T-)$_t$(T'-)$_{t'}$(T"-)$_{t''}$P are connected to $C^a$, $C^b$, $C^c$, and $C^d$ in such a way that B and (T-)$_t$(T'-)$_{t'}$(T"-)$_{t''}$P are connected to two adjacent carbon atoms or to $C^a$ and $C^d$;
Q has no meaning or is —O—CO—;
t, t', and t" are numbers representing degree of polymerization and are independently an integer of 0 to 5;
T, T', and T" are independently selected from compounds having the formula:

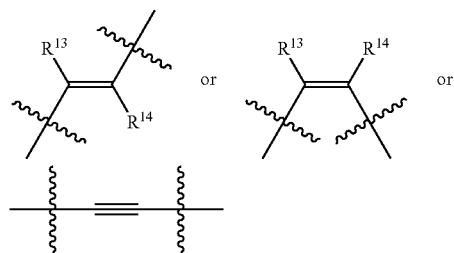

wherein $R^6$, $R^7$, $R^8$, $R^9$, $R^{10}$, $R^{11}$, $R^{12}$, $R^{13}$, and $R^{14}$ independently represent H, $C_{1-6}$ alkyl, $C_{3-20}$ heterocyclyl, $C_{5-20}$ aryl, $C_{1-6}$ alkoxy, hydroxy (OH), amino ($NH_2$), mono-substituted amino ($NR_xH$), di-substituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy (S(=O)$_2$OH), sulphonate (S(=O)$_2$$OR_x$), sulphonyl (S(=O)$_2$$R_x$), sulphixy (S(=O)OH), sulphinate (S(=O)$OR_x$), sulphinyl (S(=O)$R_x$), phosphonooxy (OP(=O)(OH)$_2$), and phosphate (OP(=O)($OR_x$)$_2$), where $R_x$, $R_x^1$ and $R_x^2$ are independently selected from a $C_{1-6}$ alkyl group, a $C_{3-20}$ heterocyclyl group or a $C_{5-20}$ aryl group, two or more of the substituents $R^6$, $R^7$, $R^8$, $R^9$, $R^{10}$, $R^{11}$, $R^{12}$, $R^{13}$, or $R^{14}$ optionally being connected to one another to form one or more aliphatic or aromatic cyclic structures.

In the formulae above, Q may be O—CO, but it may also have no meaning. For example, a compound with an aryl ether linkage between self-elimination spacer and the group that leaves, where the oxycarbonyl function is lacking (Q has no meaning), has been reported to undergo self-elimination[11].

According to a further embodiment of the invention, the ω-amino aminocarbonyl cyclization elimination spacer A is a compound having the formula:

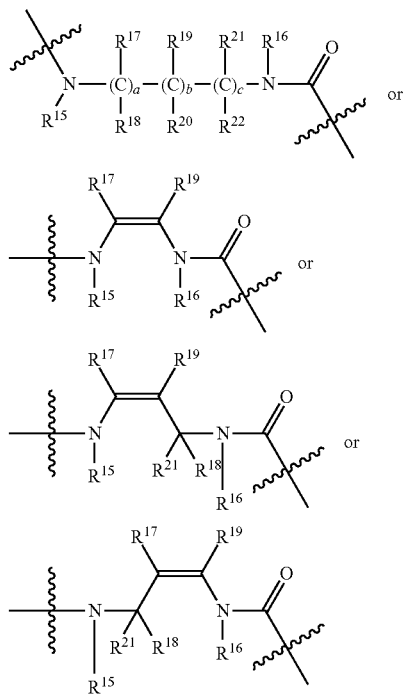

wherein
a is an integer of 0 or 1; and
b is an integer of 0 or 1; and
c is an integer of 0 or 1; provided that
a+b+c=2 or 3;

and wherein $R^{15}$ and $R^{16}$ independently represent H, $C_{1-6}$ alkyl, said alkyl being optionally substituted with one or more of the following groups: hydroxy (OH), ether ($OR_x$), amino ($NH_2$), mono-substituted amino ($NR_xH$), di-substituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy (S(=O)$_2$OH), sulphonate (S(=O)$_2$$OR_x$), sulphonyl (S(=O)$_2$$R_x$), sulphixy (S(=O)OH), sulphinate (S(=O)$OR_x$), sulphinyl (S(=O)$R_x$), phosphonooxy (OP(=O)(OH)$_2$), and phosphate (OP(=O)($OR_x$)$_2$), where $R_x$, $R_x^1$ and $R_x^2$ are independently selected from a $C_{1-6}$ alkyl group, a $C_{3-20}$ heterocyclyl group or a $C_{5-20}$ aryl group; and $R^{17}$, $R^{18}$, $R^{19}$, $R^{20}$, $R^{21}$, and $R^{22}$ independently represent H, $C_{1-6}$ alkyl, $C_{3-20}$ heterocyclyl, $C_{5-20}$ aryl, $C_{1-6}$ alkoxy, hydroxy (OH), amino ($NH_2$), mono-substituted amino ($NR_xH$), di-substituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate (COOR$_x$), sulphoxy (S(=O)$_2$OH), sulphonate (S(=O)$_2$OR$_x$), sulphonyl (S(=O)$_2$R$_x$), sulphixy (S(=O)OH), sulphinate (S(=O)OR$_x$), sulphinyl (S(=O)R$_x$), phosphonooxy (OP(=O)(OH)$_2$), and phosphate (OP(=O)(OR$_x$)$_2$), where R$_x$, R$_x^1$ and R$_x^2$ are selected from a C$_{1-6}$ alkyl group, a C$_{3-20}$ heterocyclyl group or a C$_{5-20}$ aryl group; and wherein R$^{15}$, R$^{16}$, R$^{17}$, R$^{18}$, R$^{19}$, R$^{20}$, R$^{21}$, and R$^{22}$ can be a part of one or more aliphatic or aromatic cyclic structures, two or more of the substituents R$^{15}$, R$^{16}$, R$^{17}$, R$^{18}$, R$^{19}$, R$^{20}$, R$^{21}$, or R$^{22}$ optionally being connected to one another to form one or more aliphatic or aromatic cyclic structures.

In one embodiment, the spacer system Y is selected from

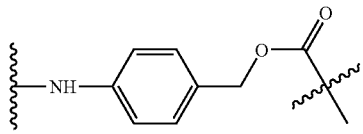

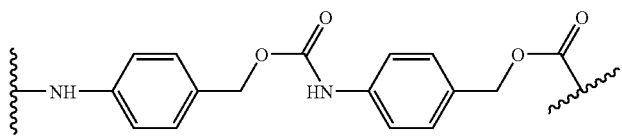

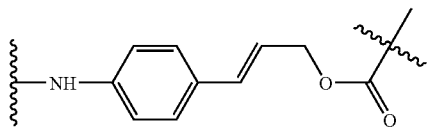

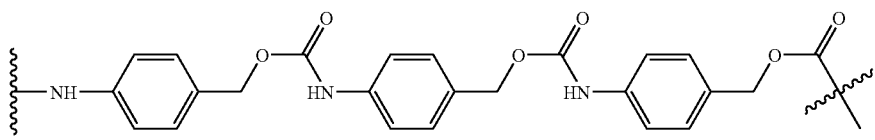

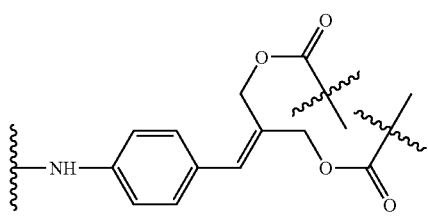

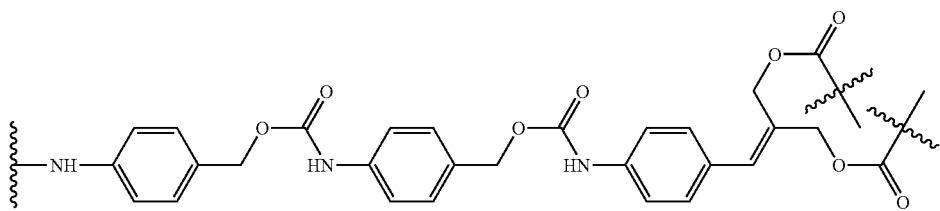

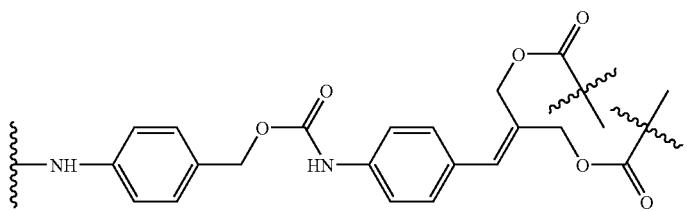

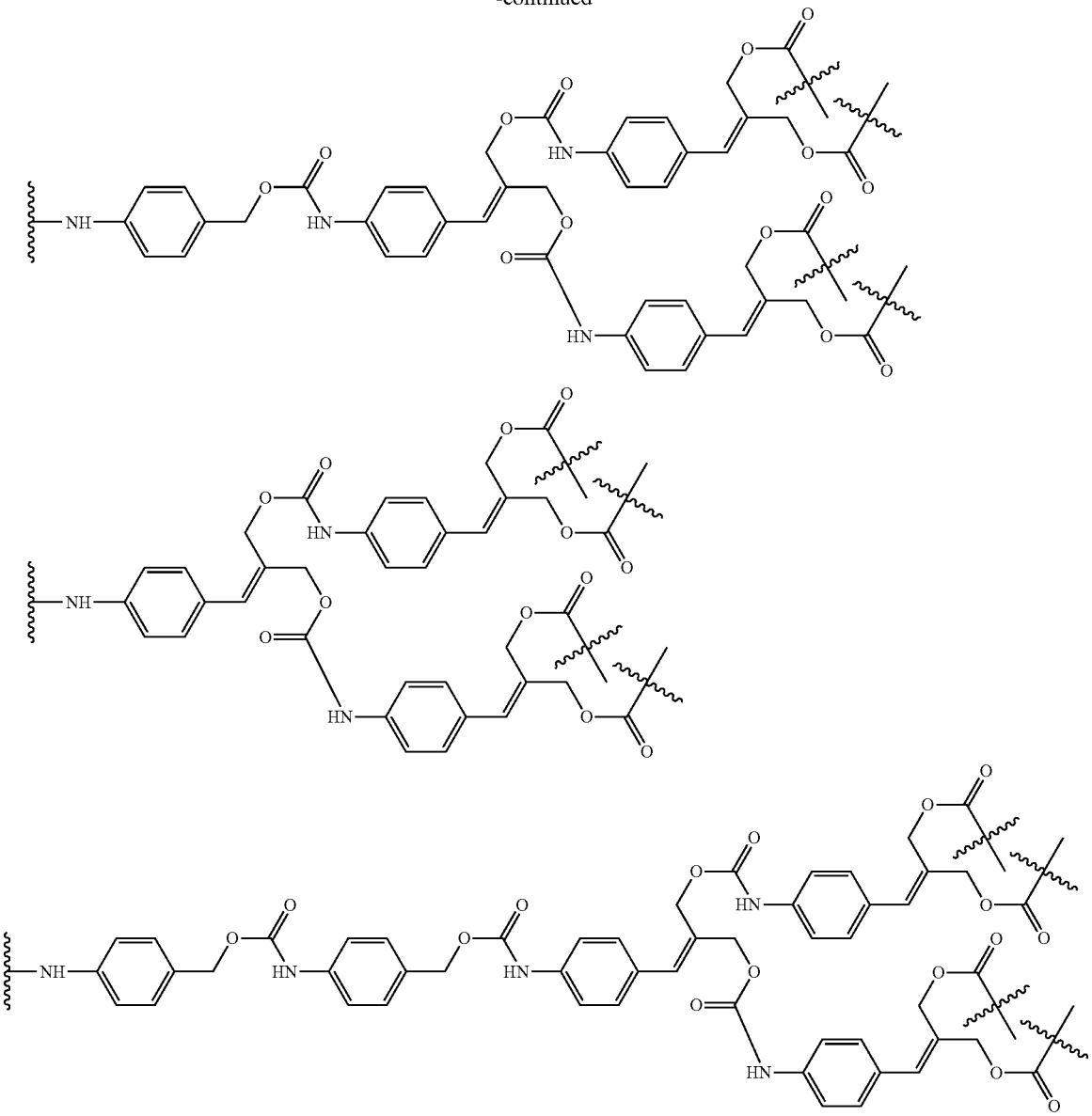

and from the formulae depicted above that further comprise one or more ω-amino aminocarbonyl cyclization spacers connected to the right-hand side of the formulae.

Other examples of self-eliminating spacer systems include, but are not limited to, spacers that can undergo cyclization such as optionally substituted 4-aminobutyric acid amides, appropriately substituted bicyclo[2.2.1] and bicyclo[2.2.2] ring systems, and 2-aminophenylpropionic acid amides and "trimethyl-lock" cyclization spacers[12]. A glycine spacer where an amine-containing drug is connected at the α-position is another useful spacer for the compounds of the invention.[13]

In a compound of this invention, a spacer system Y may be connected to more than one $V_1$ moiety. In this case, transformation and/or cleavage of one of these $V_1$ moieties may trigger the release of one or more Z moieties. When $V_1$ moieties that are transformed or cleaved under different conditions are connected to the same Y, release of one or more Z moieties may occur when a compound of this invention is brought under one of several different conditions.

The Moiety Z

The compounds of the invention comprise one or more moieties Z. Each moiety Z may be independently selected from H, OH, a leaving group, a therapeutic moiety, or a diagnostic moiety, provided that each compound of this invention comprises at least one therapeutic or diagnostic moiety. When more than one Z is a leaving group, a therapeutic moiety, or a diagnostic moiety, said moieties Z do not necessarily need to be the same. In this way, a compound of the invention may contain two or more different leaving groups, therapeutic moieties, and/or diagnostic moieties.

In general, compounds of this invention contain only or almost exclusively therapeutic and/or diagnostic Z moieties. A H or OH group or a leaving group may be accidentally introduced in a compound of this invention during its synthesis in case coupling of therapeutic and/or diagnostic moieties to the one or more spacer systems and/or $V_1$ moieties does not lead to full chemical conversion. H or OH groups will generally not act as leaving groups, but will generally not inhibit release of the other moieties Z. The leaving groups Z that remain in the conjugate will also be liberated upon breakdown of the spacer system, but will generally not be of any value nor will do harm.

The therapeutic or diagnostic moieties Z are connected to the spacer system Y or, when Y is absent, to $V_1$. It should be understood that Z cannot be attached to a $V_1$ moiety when a Y moiety is connected to said same $V_1$ moiety. When more than one Z moiety is connected to a self-elimination spacer system Y, at least one Z should be released upon self-elimination of Y.

The therapeutic or diagnostic moiety Z initially released may be a moiety that is not a fully active moiety itself. In other words, Z may be a moiety that has limited diagnostic or therapeutic abilities. Such a Z moiety may require further processing or metabolism, e.g., hydrolysis, enzymatic cleavage, or enzymatic modification (for example phosphorylation, reduction, or oxidation) in order to become fully active. In one embodiment, such further processing is intentionally designed for Z to for example allow Z to reach its final target or cross a biological barrier, e.g., a cell membrane or a nuclear membrane, before it is fully activated. Z may for example contain a hydrophobic moiety that enables Z to cross a cell membrane. This hydrophobic moiety may then be hydrolyzed or removed in any other way intracellularly.

The therapeutic or diagnostic moieties Z can be connected to Y or, when absent, to $V_1$ with any suitable atom. In one embodiment, Z is coupled via oxygen (from for example a hydroxyl group or carboxyl group), carbon (from for example a carbonyl group), nitrogen (from for example a primary or secondary amino group), or sulfur (from for example a sulfhydryl group).

In one embodiment, Z is coupled in the compounds of this invention via a group such that its therapeutic abilities or diagnostic characteristics are, at least partly, blocked or masked.

In case a compound of the invention is to be used for treating or preventing disease in an animal, e.g., a mammal, the Z moieties are generally therapeutic moieties. In case a compound of the invention is used to make a diagnosis or used in an ex vivo or in vivo diagnostic assay, the Z moieties are generally diagnostic moieties, for example chromogenic, fluorogenic, phosphorogenic, chemiluminescent, or bioluminescent compounds.

In one aspect of this invention, one or more moieties Z are each selected from a therapeutic or diagnostic agent.

In another embodiment of this invention, one or more moieties Z are each a therapeutic agent.

In another embodiment of this invention, all moieties Z are each a therapeutic agent.

In yet another embodiment, the moieties Z each are the same therapeutic moiety.

In yet another embodiment, the moieties Z comprise at least two different therapeutic moieties.

In yet another embodiment, the one or more moieties Z are each independently chosen from an antibiotic, an anti-bacterial agent, an antimicrobial agent, an anti-inflammatory agent, an anti-infectious disease agent, an anti-autoimmune disease agent, an anti-viral agent, or an anticancer agent.

In another embodiment, the one or more moieties Z are each an anticancer agent.

In a further embodiment, the one or more moieties Z are each a hydroxyl-containing anticancer agent which is connected to the spacer system Y with its hydroxyl group via an ω-amino aminocarbonyl cyclization spacer (being part of Y).

In a further embodiment, the one or more moieties Z are each independently selected from the group of taxanes, anthracyclines, camptothecins, epothilones, mytomycins, combretastatins, vinca alkaloids, nitrogen mustards, maytansinoids, calicheamycins, duocarmycins, tubulysines, dolastatins and auristatins, enediynes, radioisotopes, therapeutic proteins and peptides, and toxins or fragments thereof.

In a further embodiment, the one or more moieties Z are each independently selected from cyclophosphamide, ifosfamide, chlorambucil, 4-(bis(2-chloroethyl)amino)phenol, 4-(bis(2-fluoroethyl)amino)phenol, N,N-bis(2-chloroethyl)-p-phenylenediamine, N,N-bis(2-fluoroethyl)-p-phenylenediamine, carmustine, lomustine, treosulfan, dacarbazine, cisplatin, carboplatin, vincristine, vinblastine, vindesine, vinorelbine, paclitaxel, docetaxel, etoposide, teniposide, topotecan, irinotecan, 9-aminocamptothecin, 9-nitrocamptothecin, SN-38, 10-hydroxycamptothecin, GG211, lurtotecan, camptothecin, crisnatol, mitomycin C, mitomycin A, methotrexate, trimeterxate, mycophenolic acid, tiazofurin, ribavirin, hydroxyurea, deferoxamine, 5-fluorouracil, floxuridine, doxifluridine, raltitrexed, cytarabine, cytosine arabinoside, fludarabine, 6-mercaptopurine, thioguanine, raloxifen, megestrol, goserelin, leuprolide acetate, flutamide, bicalutamide, EB 1089, CB 1093, KH 1060, vertoporfin, phthalocyanine, photosensitizer Pc4, demethoxy-hypocrellin A, interferon-α, interferon-γ, tumor necrosis factor, lovastatin, staurosporine, actinomycin D, bleomycin A2, bleomycin B2, peplomycin, daunorubicin, doxorubicin, N-(5,5-diacetoxypentyl)doxorubicin, morpholinodoxorubicin, idarubicin, epirubicin, pirarubicin, zorubicin, mitoxantrone, thapsigargin, $N^8$-acetylspermidine, tallysomycin, esperamycin, butyric acid, retinoic acid, 1,8-dihydroxybicyclo[7.3.1]trideca-4-ene-2,6-diyne-13-one, anguidine, podophyllotoxin, combretastatin A-4, pancratistatin, caminomycin, streptonigrin, elliptinium acetate, maytansine, maytansinol, calicheamycin, mertansine (DM1), N-acetyl-$\gamma_1^1$-calicheamycin, calicheamycin-$\gamma_1^1$, calicheamycin-$\alpha_2^1$, calicheamycin-$\alpha_3^1$, duocarmycin SA, duocarmycin A, CC-1065, CBI-TMI, duocarmycin C2, duocarmycin B2, dolastatin, auristatin E, monomethylauristatin E, monomethylauristatin F, and derivatives thereof.

Other useful therapeutics are set forth in the Physician's Desk Reference and in the Orange Book maintained by the US Food and Drug Administration (FDA). New drugs are continually being discovered and developed, and the present invention provides that these new drugs may also be incorporated into a compound of this invention.

In one embodiment, the compounds of the invention comprise a therapeutic or diagnostic moiety Z that is conjugated to one or more $V_1$—Y moieties via multiple functional groups on Z. For example, one Z may be a therapeutic protein or peptide that is connected via multiple functional groups to one or more $V_1$—Y moieties. Said functional groups can for example be primary or secondary amine groups, sulfhydryl groups, or hydroxyl groups and do not need to be all the same. For example, a conjugate of formula (I) or (II) may contain a moiety Z that is a therapeutic protein or peptide and s may range from 1 to about 20, meaning that up to 20 moieties $V_2$ are present in the conjugate. These $V_2$ moieties may for example be a polymer or a water-soluble group or a combination of both, e.g., an oligoethylene glycol or a polyethylene glycol or a derivative thereof. When one Z moiety is a therapeutic protein or peptide and said $V_2$ moiety or moieties is/are for example polyethylene glycol, the conjugate of formula (I) or (II) can be considered a reversibly pegylated protein or peptide. Such a conjugate may be desirable, for example, to improve the pharmacokinetic properties of the protein or peptide, to reduce its immunogenic properties, to improve circulation time, and/or to improve aqueous solubility.

In one embodiment, a Z moiety is attached to one or more $V_1$—Y moieties via multiple functional groups on Z.

In another embodiment, a Z moiety is attached to more than one $V_1$—Y moiety via multiple functional groups on the said Z moiety.

In another embodiment, z equals 1 and the single Z moiety is connected to more than one $V_1$—Y moiety via multiple functional groups on the said Z moiety.

In another embodiment, z equals 1, the single Z moiety is connected to more than one $V_1$—Y moiety via multiple functional groups on the said Z moiety, and s ranges from about 1 to about 20.

In another embodiment, z equals 1, each $V_1$—Y moiety contains a single attachment site for a functional group of Z, and s ranges from 1 to about 20.

In another embodiment, a Z moiety is attached to more than one $V_1$—Y moiety via multiple functional groups on the said Z moiety and the one or more $V_2$ moieties are each a polymer.

In another embodiment, a Z moiety is attached to more than one $V_1$—Y moiety via multiple functional groups on the said Z moiety and the one or more $V_2$ moieties are each an oligoethylene glycol or a polyethylene glycol or a derivative thereof A compound of formula (I), and likewise a compound of formula (II), may exist as a mixture, wherein each component of the mixture has a different s value. For example, the compound may exist as a mixture of two separate compounds, one compound wherein s is 2 and another compound wherein s is 3. When analyzing the compound it is understood that s may be the (rounded) average number of $V_2$-$L_3$-$L_2$(-triazole-$L_1$(—$V_1$—Y—)$_r$)$_q$ units per compound. Furthermore, for a given s, the compound may exist as a mixture of isomers as the s $V_2$-$L_3$-$L_2$(-triazole-$L_1$(—$V_1$—Y—)$_r$)$_q$ moieties may be connected to distinct sets of functional groups on Z.

The Linking Group $L_1$

The linking group $L_1$ links one or more $V_1$ and/or Y moieties to either the alkyne, azide, or triazole moiety. $L_1$ may be a bond connecting $V_1$/Y directly to the alkyne, azide, or triazole moiety. In another aspect, however, $L_1$ is a linking group that functionally links or spaces the one or more moieties $V_1$ and/or Y and the alkyne, azide, or triazole moiety. In the case of compounds (V) and (VI), spacing may make the azide/alkyne moiety more accessible to a reaction partner in the triazole-forming reaction. In compounds (III) and (IV), spacing may make the reactive moiety RM more accessible to the reaction partner, for example when the functional moiety is coupled. In compounds (I) and (II), spacing may provide for a better accessibility of $V_1$, because $V_2$ is further removed, which, especially in the case of enzymatic cleavage or transformation of $V_1$, may improve the rate at which $V_1$ is transformed and/or cleaved.

A compound of this invention may contain more than one $L_1$ moiety. The $L_1$ moieties may or may not be the same.

The linking group $L_1$ may be a water-soluble moiety or contain one or more water-soluble moieties, such that $L_1$ contributes to the water solubility of a compound of formula (I)-(VI). $L_1$ may also be a moiety or contain one or more moieties that reduce(s) aggregation, which may or may not be a moiety/moieties that also increase(s) the water solubility. The linking group $L_1$ must contain suitable functional groups at its ends to provide for selective coupling of the one or more $V^1$ and/or Y moieties and the alkyne, azide, or triazole moiety.

In one aspect, the $L_1$ moiety is branched, e.g., a dendritic structure, so that it can be connected to more than one $V_1$ and/or Y moiety. A single $L_1$ moiety may thus be connected to one or more $V_1$ moieties and at the same time be connected to one or more Y moieties. Each $V_1$—Y moiety is however only attached once to a $L_1$ moiety. Branching can occur at one or more branching atoms that may for example be carbon, nitrogen, silicon, or phosphorus. The number of branches in $L_1$ that are connected to $V_1$ and/or Y does not necessarily equal the total number of branches as in the coupling reaction with $V_1$/Y not all branches may be coupled to $V_1$ and/or Y moieties due to incomplete chemical conversion. This means that $L_1$ may contain branches that are not coupled to $V_1$ or Y, but instead end in for example a functional group, H, OH, or a leaving group.

Therefore, when $L_1$ is branched, compounds of this invention may exist as a mixture, wherein each component of the mixture has a different r value. For example, the compound may exist as a mixture of two separate compounds, one compound wherein r is 2 and another compound wherein r is 3. Furthermore, for a given r, the compound may exist as a mixture of isomers as $V_1$/Y may be connected to distinct sets of branches on $L_1$.

In one embodiment, $L_1$ is connected to $V_1$.

In another embodiment, $L_1$ is connected to Y.

In one embodiment, $L_1$ is a bond.

In another embodiment, $L_1$ is a linear linker.

In another embodiment, $L_1$ is a branched linker.

In another embodiment, $L_1$ is a dendritic linker. The dendritic structure may for example be built up through cycloaddition reactions between molecules containing an azide group and ones containing an alkyne group.

In one embodiment, r is 1.

In other embodiments, r is about 2 or about 3 or about 4 or about 6 or about 8 or about 9.

In another embodiment, $L_1$ is represented by the formula

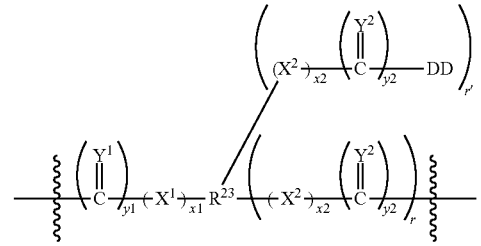

wherein $X^1$, $Y^1$ are each independently O, $NR^{24}$, or S;

Each $X^2$, $Y^2$ are each independently O, $NR^{25}$, or S;

Each y1, y2, x1, and x2 are independently 0 or 1;

r is an integer selected from 1 (included) to 128 (included);

r' is an integer selected from 0 (included) to 127 (included);

r+r'≦128;

Each DD is independently H, OH, or a leaving group;

$R^{23}$ is absent or is either a dendritic, branched or unbranched moiety and selected from optionally substituted alkylene or polyalkylene, optionally substituted heteroalkylene or polyheteroalkylene, optionally substituted arylene or polyarylene, optionally substituted heteroarylene or polyheteroarylene, optionally substituted cycloalkylene or polycycloalkylene, optionally substituted heterocycloalkylene or polyheterocycloalkylene, —(CH$_2$CH$_2$O)$_v$—, -alkylene-(CH$_2$CH$_2$O)$_v$—, —(CH$_2$CH$_2$O)$_v$-alkylene-, -alkylene-(CH$_2$CH$_2$O)$_v$-alkylene-, -heteroalkylene-(CH$_2$CH$_2$O)$_v$—, —(CH$_2$CH$_2$O)$_v$-heteroalkylene-, -heteroalkylene-(CH$_2$CH$_2$O)$_v$-alkylene-, -heteroalkylene-(CH$_2$CH$_2$O)$_v$-heteroalkylene-, -alkylene-(CH$_2$CH$_2$O)$_v$-heteroalkylene-, a dendritic structure, or an oligopeptide, or any combination of two or more of the above;

$R^{24}$ and $R^{25}$ are independently selected from H and alkyl;
v is selected from 1 (included) to 500 (included).

In one embodiment, $L_1$ may be selected from optionally substituted $C_{1-10}$ alkylene, optionally substituted $C_{1-12}$ alkyleneoxycarbonyl, optionally substituted $C_{1-12}$ carbonylalkylene, optionally substituted $C_{1-12}$ carbonylalkyleneoxycarbonyl, or $(CH_2CH_2O)_v$-carbonyl.

In another embodiment, $L_1$ may be selected from

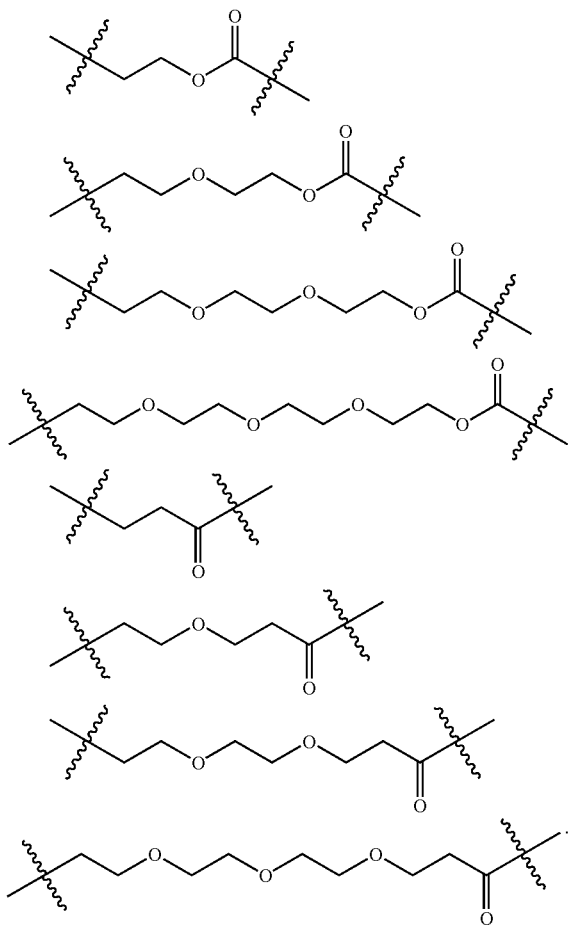

The Linking Group $L_2$

The linking group $L_2$ links the reactive moiety RM or $L_3$ to one or more triazole moieties. $L_2$ may be a bond connecting RM or $L_3$ directly to a triazole moiety. In another aspect, however, $L_2$ is a linking group that functionally links or spaces RM or $L_3$ and the one or more triazole moieties. In the case of compounds (III) and (IV), spacing may make the reactive moiety more accessible to the reaction partner, for example when the functional moiety is coupled. In compounds (I) and (II), spacing may provide for a better accessibility of $V_1$, because $V_2$ is further removed, which, especially in the case of enzymatic cleavage or transformation of $V_1$, may improve the rate at which $V_1$ is transformed and/or cleaved.

A compound of this invention may contain more than one $L_2$ moiety. The $L_2$ moieties may or may not be the same.

The linking group $L_2$ may be a water-soluble moiety or contain one or more water-soluble moieties, such that $L_2$ contributes to the water solubility of a compound of formula (I)-(IV). $L_2$ may also be a moiety or contain one or more moieties that reduce(s) aggregation, which may or may not be a moiety/moieties that also increase(s) the water solubility. The linking group $L_2$ must contain suitable functional groups at its ends to provide for selective coupling of the $L_3$/RM moiety and the one or more triazole moieties.

In one aspect, the $L_2$ moiety is branched, e.g., a dendritic structure, so that it can be connected to more than one triazole moiety. Branching can occur at one or more branching atoms that may for example be carbon, nitrogen, silicon, or phosphorus. The number of branches in $L_2$ that are connected to a triazole does not necessarily equal the total number of branches. Some branches may for example still contain an end group, being an azide or acetylene group, that has not reacted in the preparation of a compound of formula (III) or (IV) from a compound of formula (V) or (VI), respectively, due to incomplete chemical conversion.

Alternatively, the number of equivalents of a compound of formula (V) or (VI), or the aggregate number of equivalents of several distinct compounds of formula (V) or (VI), added to the acetylene-containing or azide-containing compound to form a compound of formula (III) or (IV) may be intentionally chosen to be less than the number of acetylene or azide groups present in the reactive moiety-containing compound such that one or more acetylene or azide groups remain. These can subsequently, in a next reaction step, either before or after introduction of a $V_2$ moiety, be reacted with an adjuvant moiety containing a complementary group, i.e., an azide or acetylene group, to form a compound of formula (III) or (IV) that is functionalized in $L_2$ with a covalently bound adjuvant moiety. Such an adjuvant moiety may be chosen from the same pool as $V_2$, but is preferably different from $V_2$. Said adjuvant moiety may for example assist in improving the pharmacokinetic properties of a compound of this invention or may provide (additional) targeting of a compound of this invention to a target site. For example, in one embodiment the one or more adjuvant moieties may be a water-soluble group or a group that reduces aggregation, e.g., a water-soluble polymer, e.g., a polyethylene glycol or an oligoethylene glycol or a derivative thereof, while in other embodiments, the adjuvant moiety may be a targeting moiety e.g., an antibody or antibody fragment, or an internalizing peptide such as a Tat peptide or a similar peptide.

Alternatively again, the reactive moiety-containing compound to be reacted with a compound of formula (V) or (VI) to form a compound of formula (III) or (IV) may be first reacted with one or more adjuvant moieties before the reaction with a compound of formula (V) or (VI) or reactions with a set of distinct compounds of formula (V) or (VI) is/are carried out.

Therefore, when $L_2$ is branched, compounds of this invention may exist as a mixture, wherein each component of the mixture has a different q value. For example, the compound may exist as a mixture of two separate compounds, one compound wherein q is 2 and another compound wherein q is 3. Furthermore, for a given q, the compound may exist as a mixture of isomers as the distinct triazole moieties may be connected to distinct sets of branches on $L_2$.

In one embodiment, $L_2$ is a bond.
In another embodiment, $L_2$ is a linear linker.
In another embodiment, $L_2$ is a branched linker.
In another embodiment, $L_2$ is a dendritic linker. The dendritic structure may for example be built up through cycloaddition reactions between molecules containing an azide group and ones containing an alkyne group.

In one embodiment, q is 1.
In other embodiments, q is about 2 or about 3 or about 4 or about 6 or about 8 or about 9.

In another embodiment, $L_2$ is represented by the formula

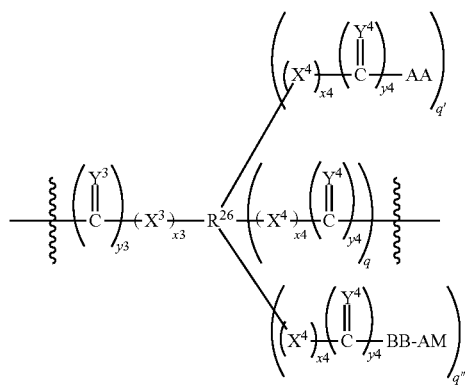

wherein
$X^3$, $Y^3$ are each independently O, $NR^{27}$, or S;
Each $X^4$, $Y^4$ are each independently O, $NR^{28}$, or S;
AA is either an azide or an acetylene group;
BB is a 1,4-substituted 1,2,3-triazole;
Each AM is independently an adjuvant moiety;
Each y3, y4, x3, and x4 are independently 0 or 1;
q is an integer selected from 1 (included) to 128 (included) and q' and q" are integers independently selected from 0 (included) to 127 (included) with q+q'+q"≦128;
$R^{26}$ is absent or is either a dendritic, branched or unbranched moiety and selected from optionally substituted alkylene or polyalkylene, optionally substituted heteroalkylene or polyheteroalkylene, optionally substituted arylene or polyarylene, optionally substituted heteroarylene or polyheteroarylene, optionally substituted cycloalkylene or polycycloalkylene, optionally substituted heterocycloalkylene or polyheterocycloalkylene, —$(CH_2CH_2O)_v$—, -alkylene-$(CH_2CH_2O)_v$—, —$(CH_2CH_2O)_v$-alkylene-, -alkylene-$(CH_2CH_2O)_v$-alkylene-, -heteroalkylene-$(CH_2CH_2O)_v$—, —$(CH_2CH_2O)_v$-heteroalkylene-, -heteroalkylene-$(CH_2CH_2O)_v$-alkylene-, -heteroalkylene-$(CH_2CH_2O)_v$-heteroalkylene-, -alkylene-$(CH_2CH_2O)_v$-heteroalkylene-, a dendritic structure, or an oligopeptide, or any combination of two or more of the above;
$R^{27}$ and $R^{28}$ are independently selected from H and alkyl;
v is selected from 1 (included) to 500 (included).

For example, $L_2$ may be selected from optionally substituted $C_{1-10}$ alkylene, optionally substituted $C_{1-10}$ heteroalkylene, optionally substituted $C_{1-12}$ alkylenecarbonyl, optionally substituted $C_{1-12}$ heteroalkylenecarbonyl, optionally substituted $(CH_2CH_2O)_v$—$C_{1-5}$ alkylene, optionally substituted $(CH_2CH_2O)_v$—$C_{1-5}$ heteroalkylene, optionally substituted $C_{1-5}$ alkylene-$(CH_2CH_2O)_v$—$C_{1-5}$ alkylene, and optionally substituted $C_{1-5}$ alkylene-$(CH_2CH_2O)_v$—$C_{1-5}$ heteroalkylene.

In another embodiment, $L_2$ may be selected from

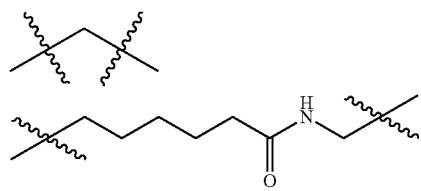

-continued

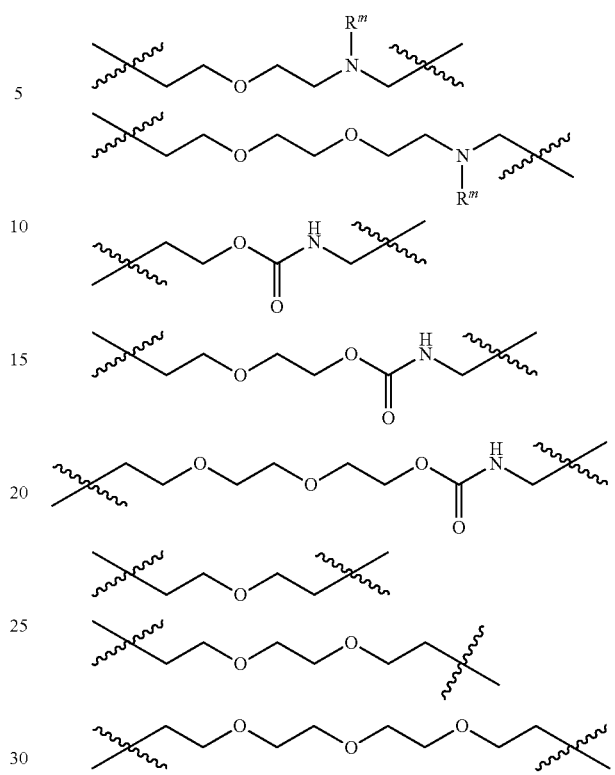

wherein $R^m$ is selected from H and $C_{1-3}$ alkyl.

In yet another embodiment, $L_2$ may be selected from

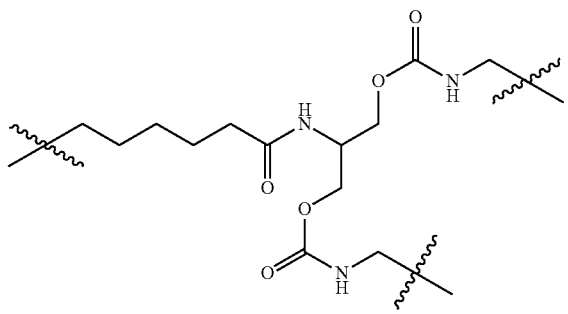

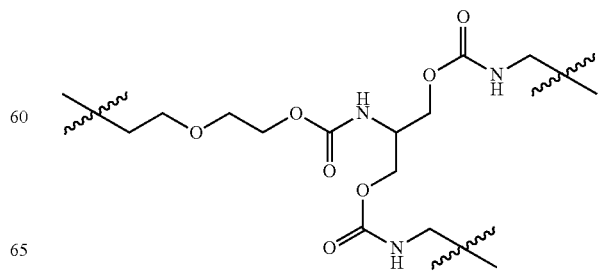

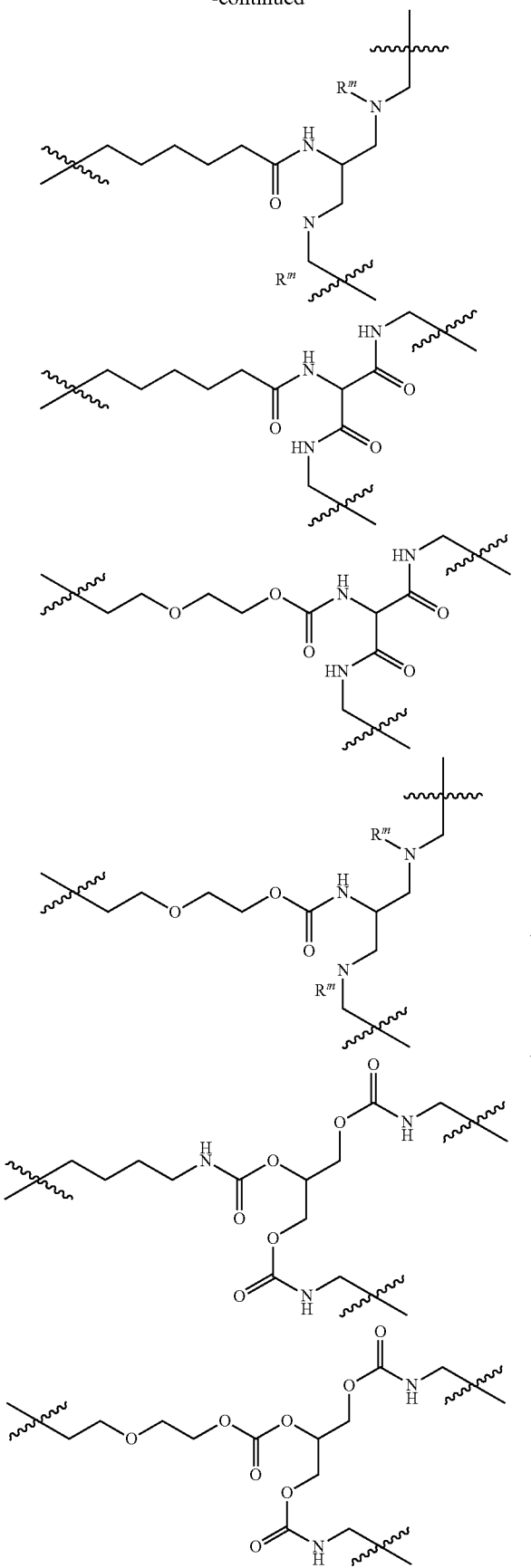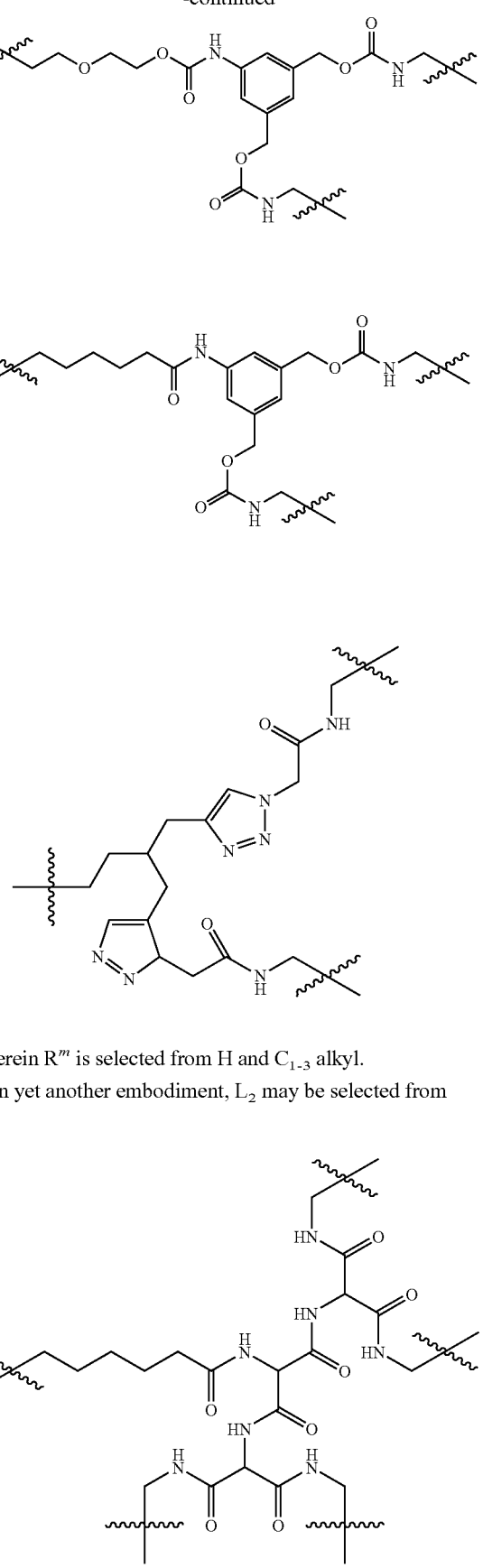
wherein $R^m$ is selected from H and $C_{1-3}$ alkyl.
In yet another embodiment, $L_2$ may be selected from
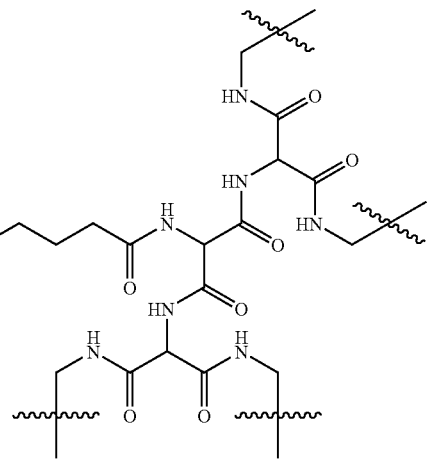

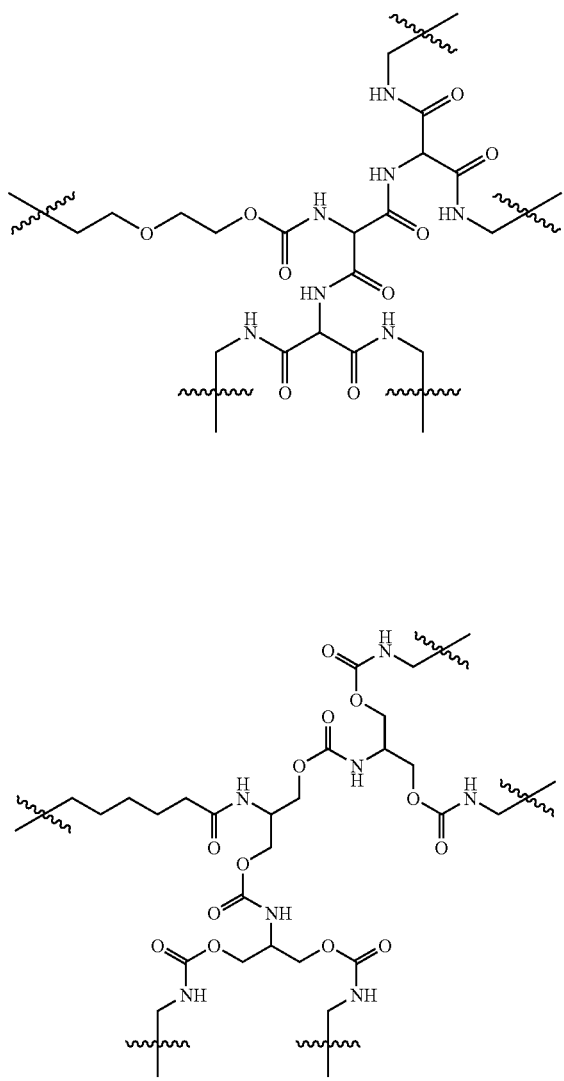

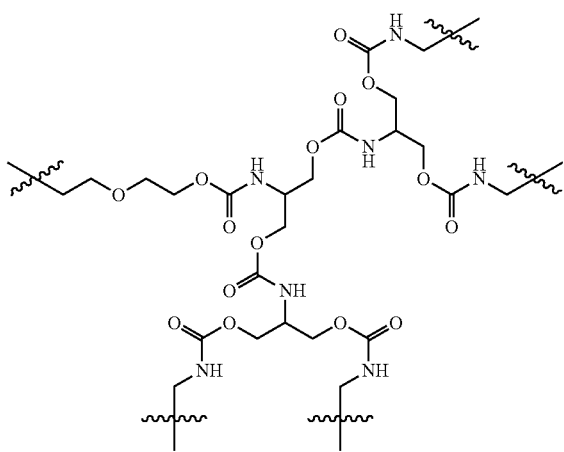

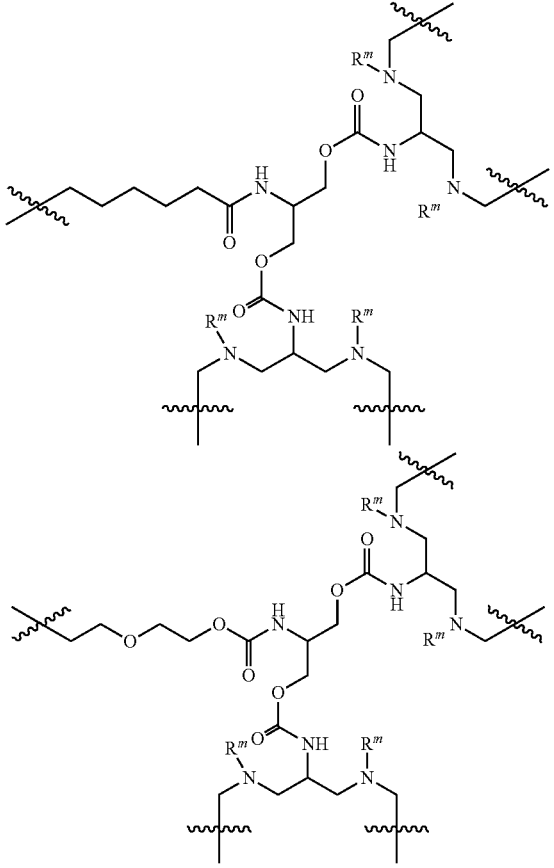

wherein $R^m$ is selected from H and $C_{1-3}$ alkyl.

In other embodiments q' and q" are integers selected from 0 (included) to 63 (included) or 31 (included) or 15 (included) or less than 15, and q+q'+q" is smaller than or equal to 64 or 32 or 16. In other embodiments, r' is an integer selected from 0 (included) to 63 (included) or 31 (included) or 15 (included) or less than 15, and r+r' is smaller than or equal to 64 or 32 or 16.

The Reactive Moiety RM and the Linking Group $L_3$

The reactive moiety RM is connected to the linking group $L_2$ and is able to react with a suitable functional group on a reaction partner.

In one embodiment of this invention, the reactive moiety RM is designed to react with a functional group on $V_2$, which results in formation of a compound of formula (I) or (II). In this reaction, the moiety RM is transformed into the moiety $L_3$. In another embodiment, the reactive moiety RM is designed to react with a complementary moiety in situ to give a compound that may or may not be a compound of formula (I) or (II).

A compound of this invention may contain more than one reactive moiety RM. The RM moieties may or may not be the same.

In one aspect of the invention, the reactive moiety RM contains an electrophilic group that reacts with a nucleophilic group on the reaction partner, for example $V_2$, e.g., a thiol group, an amino group, or a hydroxyl group.

In another aspect of the invention, the reactive moiety RM contains a nucleophilic group that reacts with an electrophilic group on the reaction partner, for example $V_2$, e.g., an aldehyde group.

In another aspect of the invention, the reactive moiety RM contains a cycloaddition partner moiety, e.g., an alkene, a diene, a 1,3-dipole, or a 1,3-dipolarophile, that reacts with a suitable complementary cycloaddition partner moiety on the reaction partner, for example $V_2$, e.g., a diene, an alkene, a 1,3-dipolarophile, or a 1,3-dipole.

In another aspect of the invention, the reactive moiety RM contains a group that can be coupled with a suitable complementary group on the reaction partner, for example $V_2$, under metal-catalyzed conditions, e.g., palladium-catalyzed conditions.

In one aspect of the invention, the reactive moiety RM is, without limitation,

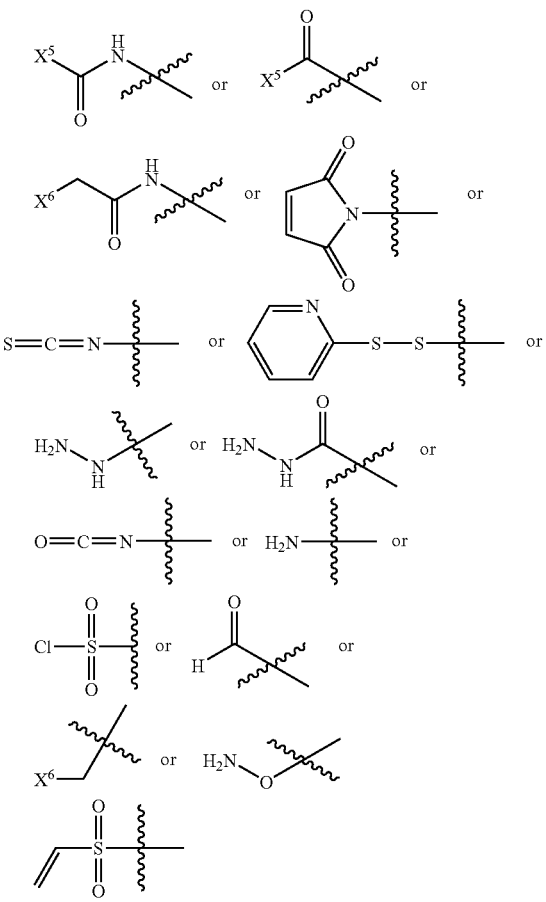

wherein
$X^5$ is selected from —Cl, —Br, —I, —F, —OH, —O—N-succinimide, —O-(4-nitrophenyl), —O-pentafluorophenyl, —O-tetrafluorophenyl, —O—C(O)—$R^{29}$, and —O—C(O)—$OR^{29}$;
$X^6$ is selected from —Cl, —Br, —I, —O-mesyl, —O-triflyl, and —O-tosyl;
$R^{29}$ is branched or unbranched $C_1$-$C_{10}$ alkyl or aryl.

In one embodiment, the moiety RM is chosen from

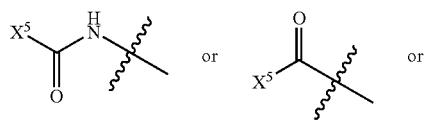

-continued

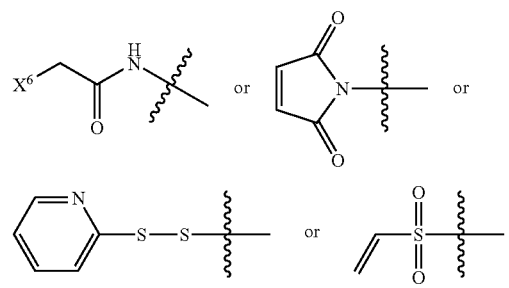

which makes it able to react with a thiol group on the reaction partner, for example moiety $V_2$.

In one embodiment, the moiety RM is chosen from

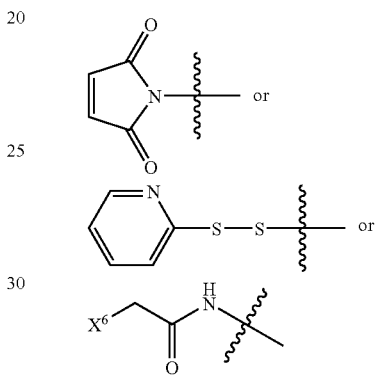

which makes it able to react with a thiol group on the reaction partner, for example moiety $V_2$.

In another embodiment, the moiety RM is

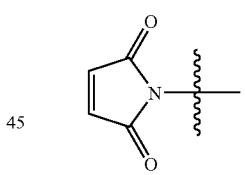

which makes it able to react with a thiol group on the reaction partner, for example moiety $V_2$.

In another embodiment, the moiety RM is chosen from

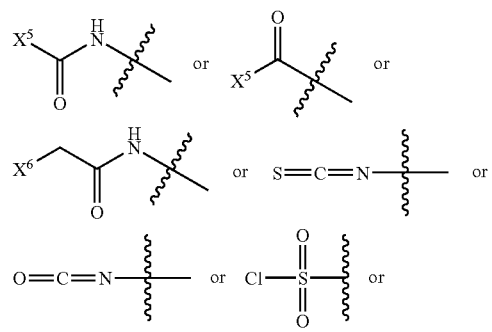

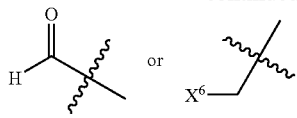 or which makes it able to react with an amino group, e.g., a primary or secondary amino group, on the reaction partner, for example moiety $V_2$.

In another embodiment, the moiety RM is chosen from

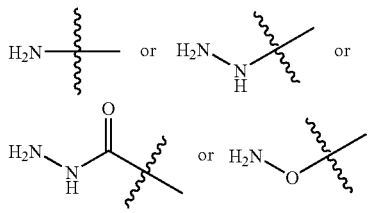

which makes it able to react with an aldehyde group on the reaction partner, for example moiety $V_2$.

The linking group $L_3$ in compounds of formula (I) and (II) represents the remainder of RM when the reactive moiety RM has reacted with $V_2$. This group then links the moiety $V_2$ with $L_2$. The group that remains may be a bond. Typically, however, $L_3$ is a linking group. When a compound of formula (I) or (II) is formed other than via a compound of formula (III) or (IV), $L_3$ does not represent the remainder of RM, but may represent a similar or the same moiety and in addition be selected from for example branched or unbranched and optionally substituted alkylene, heteroalkylene, cycloalkylene, heterocycloalkylene, arylene, or heteroarylene.

In one embodiment, the moiety $L_3$ is a bond.

In another embodiment, the moiety $L_3$ is selected from

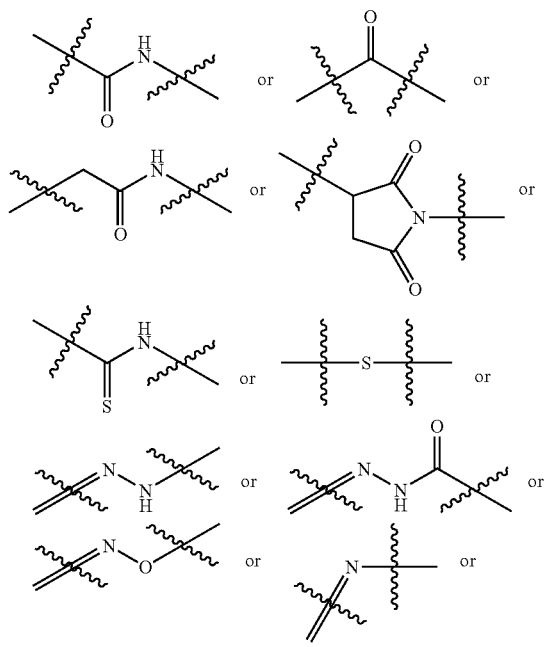

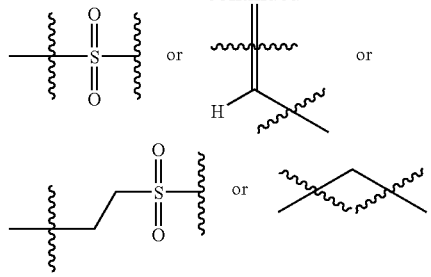

In one embodiment, $L_3$ is selected from

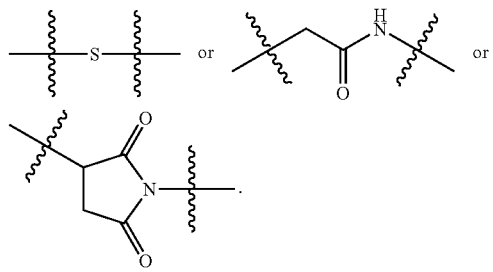

In another embodiment, $L_3$ is

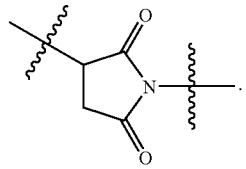

The Moiety $V_2$

The moiety $V_2$ is a functional moiety, which means that it adds additional functionality to a compound of the invention.

In one embodiment, $V_2$ is a targeting moiety. In another embodiment, the $V_2$ moiety is a moiety that improves the pharmacokinetic properties of a compound of the invention. In yet another embodiment, the $V_2$ moiety is a moiety that causes accumulation of compounds of the invention at a target site. In yet another embodiment, the $V_2$ moiety is a moiety that improves the aqueous solubility of a compound of the invention. In yet another embodiment, the $V_2$ moiety is a moiety that increases the hydrophobicity of a compound of the invention. In yet another embodiment, the $V_2$ moiety is a moiety that reduces extravasation of a compound of the invention. In yet another embodiment, the $V_2$ moiety is a moiety that reduces excretion of a compound of the invention. In yet another embodiment, the $V_2$ moiety is a moiety that reduces the immunogenicity of a compound of the invention. In yet another embodiment, the $V_2$ moiety is a moiety that enhances the circulation time of a compound of the invention. In yet another embodiment, the $V_2$ moiety is a moiety that enhances the ability of a compound of the invention to cross a biological barrier, e.g., a membrane, cell wall, or the blood-brain barrier. In yet another embodiment, the $V_2$ moiety is a moiety that enhances the ability of a compound of the invention to internalize. In yet another embodiment, the $V_2$ moiety is a moiety that causes the compounds of the invention to aggregate. In yet another embodiment, the $V_2$ moiety is a moiety that reduces the compounds to aggregate. In yet another embodiment, the $V_2$ moiety is a moiety that causes the compounds of the invention to form micelles or liposomes. In yet another embodiment, the $V_2$ moiety is a moiety that causes complexation of a compound of the invention to another molecule, e.g., a biomolecule. In yet another embodiment, the $V_2$ moiety is a polynucleotide moiety that complexes with a complementary nucleotide sequence, for example RNA or DNA. In yet another embodiment, the $V_2$ moiety is a moiety that causes a compound of the invention to bind, associate, interact, or complex to another moiety, for example a (functionalized) surface or solid support.

In another embodiment, $V_2$ exhibits two or more different functions.

A compound of this invention may contain more than one $V_2$ moiety. The $V_2$ moieties may or may not be the same.

In one aspect of the invention, the moiety $V_2$ includes within its scope any unit that binds or reactively associates or complexes with a receptor, antigen, or other receptive moiety associated with a given target cell population. $V_2$ can be any molecule that binds to, complexes with, or reacts with a moiety of a cell population sought to be therapeutically or otherwise biologically modified. The $V_2$ moiety acts to deliver the one or more moieties Z to the particular target cell population with which $V_2$ reacts or to which $V_2$ binds. Such $V_2$ moieties include, but are not limited to, aptamers, large molecular weight proteins such as, for example, full-length antibodies and antibody fragments, and smaller molecular weight proteins, polypeptides or peptides, and lectins. Upon binding, reactively associating, or complexing, the compounds of the invention may or may not be internalized. If internalization occurs, transformation and/or cleavage of $V_1$ preferably occur inside the target cell.

Useful non-immunoreactive protein, polypeptide, or peptide $V_2$ moieties include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-a and TGF-P, tumor growth factors, vaccinia growth factor ("VGF"), insulin and insulin-like growth factors I and II, lectins, and apoprotein from low density lipoprotein.

Useful polyclonal antibody $V_2$ moieties are heterogeneous populations of antibody molecules. Various procedures well-known in the art may be used for the production of polyclonal antibodies to an antigen-of-interest.

Useful monoclonal antibody $V_2$ moieties are homogeneous populations of antibodies to a particular antigen (e.g., a cancer cell antigen). A monoclonal antibody (mAb) to an antigen-of-interest can be prepared by using any technique known in the art which provides for the production of monoclonal antibody molecules.

Useful monoclonal antibody $V_2$ moieties include, but are not limited to, human monoclonal antibodies, humanized monoclonal antibodies, or chimeric human-mouse (or other species) monoclonal antibodies. Human monoclonal antibodies may be made by any of numerous techniques known in the art.

The $V_2$ moiety can also be a bispecific antibody. Methods for making bispecific antibodies are known in the art.

The $V_2$ moiety can be a functionally active fragment, derivative, or analog of an antibody that immunospecifically binds to antigens on the target cells, e.g., cancer cell antigens. In this regard, "functionally active" means that the fragment, derivative, or analog is able to elicit anti-anti-idiotype antibodies that recognize the same antigen that the antibody from which the fragment, derivative, or analog is derived recognizes.

Other useful $V_2$ moieties include fragments of antibodies such as, but not limited to, F(ab')$_2$ fragments, which contain the variable region, the light chain constant region and the CH1 domain of the heavy chain, which can be produced by pepsin digestion of the antibody molecule, and Fab fragments, which can be generated by reducing the disulfide bridges of the F(ab')$_2$ fragments. Other useful $V_2$ moieties are heavy chain and light chain dimers of antibodies, or any minimal fragment thereof such as Fvs or single chain antibodies (SCAs), domain antibodies, anticalins, affibodies, nanobodies, or any other molecule with the same, similar, or comparable specificity as the antibody. Additionally, recombinant antibodies, such as chimeric and humanized monoclonal antibodies, comprising both human and non-human portions, which can be made using standard recombinant DNA techniques, are useful $V_2$ moieties. A chimeric antibody is a molecule in which different portions are derived from different animal species, such as those having a variable region derived from a murine monoclonal and a human immunoglobulin constant region. Humanized antibodies are antibody molecules from non-human species having one or more complementarity determining regions (CDRs) from the non-human species and a framework region from a human immunoglobulin molecule.

Completely human antibodies are particularly desirable as $V_2$ moieties. Such antibodies can for example be produced using transgenic mice that are incapable of expressing endogenous immunoglobulin heavy and light chains genes, but which can express human heavy and light chain genes. In other embodiments, the $V_2$ moiety is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least a 10, 20, or 50 amino acid portion of the protein) that is not the antibody. Preferably, the antibody or fragment thereof is covalently linked to the other protein at the N-terminus of the constant domain.

The $V_2$ moiety antibodies include analogs and derivatives that are modified, i.e., by the covalent attachment of any type of molecule as long as such covalent attachment permits the antibody to retain its antigen binding immunospecificity. For example, but not by way of limitation, the derivatives and analogs of the antibodies include those that have been further modified, e.g., by glycosylation, acetylation, pegylation, phosphylation, amidation, derivatization by known protecting or blocking groups, proteolytic cleavage, linkage to another protein, etc. Additionally, the analog or derivative can contain one or more unnatural amino acids.

The $V_2$ moiety antibodies include antibodies having modifications (e.g., substitutions, deletions, or additions) in amino acid residues that interact with Fe receptors. In particular, they include antibodies having modifications in amino acid residues identified as involved in the interaction between the Fe domain and the FcRn receptor.

In a specific embodiment, an antibody immunospecific for a cancer or tumor antigen is used as a $V_2$ moiety in accordance with the compounds, compositions, and methods of the invention.

Antibodies immunospecific for a cancer cell antigen can be obtained commercially or produced by any method known to one of skill in the art such as, e.g., chemical synthesis or recombinant expression techniques. The nucleotide sequences encoding antibodies immunospecific for a cancer cell antigen can be obtained, e.g., from the GenBank database or a database like it, literature publications, or by routine cloning and sequencing.

Examples of antibodies available for the treatment of cancer include, but are not limited to, HERCEPTIN (Trastuzumab; Genentech, CA) which is a humanized anti-HER2 monoclonal antibody for the treatment of patients with metastatic breast cancer; RITUXAN (rituximab; Genentech), which is a chimeric anti-CD20 monoclonal antibody for the treatment of patients with non-Hodgkin's lymphoma; OvaRex (oregovomab; AltaRex Corporation, MA) which is a murine antibody for the treatment of ovarian cancer; Panorex (edrecolomab; Glaxo Wellcome, NC) which is a murine $IgG_{2a}$ antibody for the treatment of colorectal cancer; IMC-BEC2 (mitumomab; ImClone Systems Inc., NY) which is a murine IgG antibody for the treatment of lung cancer; IMC-C225 (erbitux; Imclone Systems Inc., NY) which is a chimeric IgG antibody for the treatment of head and neck cancer; Vitaxin (MedImmune, Inc., MD) which is a humanized antibody for the treatment of sarcoma; Campath I/H (Leukosite, MA) which is a humanized $IgG_1$ antibody for the treatment of chronic lymphocytic leukemia (CLL); SGN-70 (Seattle Genetics, WA) which is a humanized anti-CD70 antibody for the treatment of hematologic malignancies; Smart MI95 (Protein Design Labs, Inc., CA) which is a humanized IgG antibody for the treatment of acute myeloid leukemia (AML); LymphoCide (epratuzumab; Immunomedics, Inc., NJ) which is a humanized IgG antibody for the treatment of non-Hodgkin's lymphoma; SGN-33 (Seattle Genetics, WA) which is a humanized anti-CD33 antibody for the treatment of acute myeloid leukemia; Smart ID 10 (Protein Design Labs, Inc., CA) which is a humanized antibody for the treatment of non-Hodgkin's lymphoma; Oncolym (Techniclone, Inc., CA) which is a murine antibody for the treatment of non-Hodgkin's lymphoma; Allomune (BioTransplant, CA) which is a humanized anti-CD2 mAb for the treatment of Hodgkin's disease or non-Hodgkin's lymphoma; anti-VEGF (Genentech, Inc., CA) which is a humanized antibody for the treatment of lung and colorectal cancers; SGN-40 (Seattle Genetics, WA) which is a humanized anti-CD40 antibody for the treatment of multiple myeloma; SGN-30 (Seattle Genetics, WA) which is a chimeric anti-CD30 antibody for the treatment of Hodgkin's disease; CEAcide (Immunomedics, NJ) which is a humanized anti-CEA antibody for the treatment of colorectal cancer; IMC-1C11 (ImClone Systems, NJ) which is an anti-KDR chimeric antibody for the treatment of colorectal cancer, lung cancers, and melanoma; and Cetuximab (ImClone, NJ) which is an anti-EGFR chimeric antibody for the treatment of epidermal growth factor positive cancers. Some other useful antibodies include, but are not limited to, BR96 and BR64, mAbs against the CD40 antigen, such as S2C6 mAb, and mAbs against CD30, such as AC10.

Other antibodies useful in the treatment of cancer include, but are not limited to, antibodies against the following antigens: CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific antigen (prostate), prostatic acid phosphatase (prostate), epidermal growth factor (carcinomas), HER2 (breast cancer), MAGE-1 (carcinomas), MAGE-2 (carcinomas), MAGE-3 (carcinomas), MAGE-4 (carcinomas), anti-transferrin receptor (carcinomas), p97 (melanoma), MUC1-KLH (breast cancer), MUC18 (melanoma), PSMA (prostate), CTLA4 (T-cell lymphoma), CEA (colorectal), gp100 (melanoma), MART1 (melanoma), IL-2 receptor (T-cell leukemia and lymphomas), CD20 (lymphomas), CD4 (lymphomas), CD30 (lymphomas), CD52 (leukemia), CD56, CD74 (lymphomas), CD33 (leukemia), CD22 (lymphomas), human chorionic gonadotropin (carcinoma), CD38 (multiple myeloma), CD40 (lymphomas), mucin (carcinomas), P21 (carcinomas), MPG (melanoma), and Neu oncogene product (carcinomas). Many other internalizing or non-internalizing antibodies that bind to tumor-associated antigens can be used in this invention, some of which have been reviewed[14]. New antibodies are continually being discovered and developed, and the present invention provides that these new antibodies may also be incorporated into a compound of this invention.

In another specific embodiment, an antibody immunospecific for an antigen associated with an autoimmune disease is used as a $V_2$ moiety in accordance with the compounds, compositions, and methods of the invention.

In another specific embodiment, an antibody immunospecific for a viral or microbial antigen is used as a $V_2$ moiety in accordance with the compounds, compositions, and methods of the invention.

$V_2$ can react with the reactive moiety RM via for example a heteroatom on $V_2$. Heteroatoms that may be present on $V_2$ include, without limitation, sulfur (in one embodiment, from a sulfhydryl group), oxygen (in one embodiment, from a carboxyl or hydroxyl group), and nitrogen (in one embodiment, from a primary or secondary amino group). $V_2$ may also react via for example a carbon atom (in one embodiment, from a carbonyl group). These atoms can be present on $V_2$ in $V_2$'s natural state, for example a naturally occurring antibody, or can be introduced into $V_2$ via chemical modification.

Free sulfhydryl groups can be generated in an antibody or antibody fragment by reduction of the antibody with a reducing agent such as dithiothreitol (DTT) or tris(2-carboxyethyl) phosphine (TCEP). In this way, modified antibodies can be obtained that can have from 1 to about 20 sulfhydryl groups, but typically between about 1 to about 9 sulfhydryl groups.

Alternatively, $V_2$ can have one or more carbohydrate groups that can be chemically modified to have one or more sulfhydryl groups. As another alternative, sulfhydryl groups can be generated by reaction of an amino group, for example from a lysine moiety, of $V_2$ using 2-iminothiolane (Traut's reagent) or another sulfhydryl-generating reagent.

In one embodiment, the $V_2$ moiety is a receptor-binding moiety.

In another embodiment, the $V_2$ moiety is an antibody or an antibody fragment.

In another embodiment, the $V_2$ moiety is a monoclonal antibody or a fragment thereof.

In one embodiment, $V_2$ has one or more sulfhydryl groups and $V_2$ reacts with one or more RM moieties via one or more of these sulfhydryl groups' sulfur atoms.

In yet another embodiment, $V_2$ contains disulfide bonds that can be selectively chemically reduced to sulfhydryl groups (two for each disulfide bond), which can then be reacted with one or more reactive moieties RM.

In another embodiment, $V_2$ contains about 1 to about 3 sulfhydryl groups, which can be reacted with one or more reactive moieties RM.

In another embodiment, $V_2$ contains about 3 to about 5 sulfhydryl groups, which can be reacted with one or more reactive moieties RM.

In another embodiment, $V_2$ contains about 7 to about 9 sulfhydryl groups, which can be reacted with one or more reactive moieties RM.

In another embodiment, $V_2$ can have one or more carbohydrate groups that can be chemically modified to have one or more sulfhydryl groups. $V_2$ reacts with RM via the one or more sulfhydryl groups' sulfur atoms.

In another embodiment, $V_2$ can have one or more lysine groups that can be chemically modified to have one or more sulfhydryl groups, which can be reacted with one or more reactive moieties RM.

In yet another embodiment, $V_2$ can have one or more carbohydrate groups that can be oxidized to provide one or more aldehyde groups. The corresponding aldehyde(s) can then react with one or more reactive moieties RM. Reactive moieties that can react with a carbonyl group on $V_2$ include, but are not limited to, hydrazine, hydrazide, amine, and hydroxylamine.

In yet another embodiment, $V_2$ can have one or more amino groups, e.g., from lysine residues, which can be reacted with one or more reactive moieties RM. Reactive moieties that can react with an amino group on $V_2$ include, but are not limited to, acyl halides, α-halo acetamides, isocyanates, and isothiocyanates.

The compound of formula (I), and likewise the compound of formula (II), may exist as a mixture, wherein each component of the mixture has a different p value. For example, the compound may exist as a mixture of two separate compounds, one compound wherein p is 7 and another compound wherein p is 8. When analyzing the compound it is understood that p may be the (rounded) average number of $L_3$-$L_2$(-triazole-$L_1$(—$V_1$—Y—)$_r$)$_q$(Z)$_{z/p}$ units per $V_2$ moiety. Furthermore, for a given p, the compound may exist as a mixture of isomers as the p $L_3$-$L_2$(-triazole-$L_1$(—$V_1$—Y—)$_r$)$_q$(Z)$_{z/p}$ units may be connected to distinct sets of functional groups on $V_2$. It should be noted that the number of Z moieties in each unit only equals z/p when all units are the same and/or contain the same number of Z moieties.

In one embodiment, the $V_2$ moiety is connected to $L_3$ via a sulfur atom.

In another embodiment, the $V_2$ moiety is connected to $L_3$ via a sulfur atom and p ranges from about 1 to about 20.

In another embodiment, the $V_2$ moiety is connected to $L_3$ via a sulfur atom and p ranges from about 1 to about 9.

In another embodiment, the $V_2$ moiety is connected to $L_3$ via a sulfur atom and p ranges from about 1 to about 3.

In another embodiment, the $V_2$ moiety is connected to $L_3$ via a sulfur atom and p is about 2.

In another embodiment, the $V_2$ moiety is connected to $L_3$ via a sulfur atom and p ranges from about 3 to about 5.

In another embodiment, the $V_2$ moiety is connected to $L_3$ via a sulfur atom and p is about 4.

In another embodiment, the $V_2$ moiety is connected to $L_3$ via a sulfur atom and p ranges from about 7 to about 9.

In another embodiment, the $V_2$ moiety is connected to $L_3$ via a sulfur atom and p is about 8.

In one embodiment, a compound of formula (I) or (II) exists as a mixture of separate compounds.

In one embodiment, a compound of formula (I) or (II) exists as a mixture of separate compounds wherein p for three compounds is 1, 2, and 3, respectively.

In one embodiment, a compound of formula (I) or (II) exists as a mixture of separate compounds wherein p for three compounds is 3, 4, and 5, respectively.

In one embodiment, a compound of formula (I) or (II) exists as a mixture of separate compounds wherein p for three compounds is 5, 6, and 7, respectively.

In one embodiment, a compound of formula (I) or (II) exists as a mixture of separate compounds wherein p for three compounds is 7, 8, and 9, respectively.

In another embodiment, the $V_2$ moiety is connected to $L_3$ via a nitrogen atom.

In again another embodiment, the $V_2$ moiety is connected to $L_3$ via a carbon atom.

In another aspect of this invention, the $V_2$ moiety includes any unit that causes accumulation of compounds of the invention at the target site or in the vicinity thereof by a mechanism other than binding or reactively associating or complexing with a receptor, antigen, or other receptive moiety associated with a given target site, e.g., a target cell population. One way to achieve this is for example to use a large macromolecule as a $V_2$ moiety, which targets to solid tumor tissue through the enhanced permeability and retention (EPR) effect. Ringsdorf reported use of polymers to target antitumor agents to tumors.[1] Through this EPR effect, macromolecules passively accumulate in solid tumors as a consequence of the disorganized pathology of angiogenic tumor vasculature with its discontinuous endothelium, leading to hyperpermeability to large macromolecules, and the lack of effective tumor lymphatic drainage.

The $V_2$ moiety may for example be a branched or unbranched polymer, such as for example poly[N-(2-hydroxypropyl)methacrylamide] (HPMA), poly(2-hydroxyethyl metacrylate) (HEMA), poly-glutamic acid or poly-L-glutamic acid (PG), carboxymethyldextran (CMDex), a polyacetal, chitosan, a polypeptide, an oligoethylene glycol or polyethylene glycol (PEG), or a copolymer, such as a HPMA copolymer, a HPMA-methacrylic acid copolymer, a HEMA-methacrylic acid copolymer, a CMDex copolymer, a β-cyclodextrin copolymer, a PEG copolymer, or a poly(lactic-co-glycolic) acid copolymer.[16] Polymer and copolymer are herein jointly referred to as polymer.

The polymer may be connected to $L_3$ via any suitable functional group, which can be located at one or both ends of the polymer, meaning that in the conjugate p ranges from 1 to 2, or alternatively, the functional groups may (also) be located on groups pendant on the polymer such that $L_3$ is (also) connected to the polymer via these pendant groups with p typically ranging from 1 to about 1000. Optionally, the polymer may also contain an additional targeting group that can bind or reactively associate or complex with a receptive moiety, e.g., an antibody or antibody derivative, bonded to the polymer either via a pendant group or end group, such that improved targeting to the target site is achieved. Alternatively, an adjuvant moiety being part of $L_2$ may be an additional targeting group that can bind or reactively associate or complex with a receptive moiety, e.g., an antibody or antibody derivative.

Alternatively, the $V_2$ moiety may also be a dendrimer or a protein or protein fragment, e.g., albumin or a fragment thereof, that has no targeting properties except for its ability to accumulate at the target site because of its size or molecular weight.

In one embodiment, the $V_2$ moiety is a polymer.

In another embodiment, the $V_2$ moiety is a polymer and p ranges from 1 to about 1000.

In other embodiments, the $V_2$ moiety is a polymer and p ranges from 1 to about 500 or 400 or 300 or 200 or 100 or less than 100.

In another embodiment, the $V_2$ moiety is a polymer and p ranges from 1 to 2.

In a specific embodiment, the $V_2$ moiety is an oligoethylene glycol or a polyethylene glycol or a derivative thereof.

In another embodiment, the $V_2$ moiety is a dendrimer, a protein, or a protein fragment.

Thus, in one aspect of the invention, the moiety $V_2$ is a targeting moiety and is for example selected from the group consisting of a protein or protein fragment, an antibody or an antibody fragment, a receptor-binding or peptide vector moiety, and a polymeric or dendritic moiety, or any combination thereof.

In another aspect of the invention, the $V_2$ moiety is a moiety that improves the pharmacokinetic properties of a compound of the invention. For example, the moiety $V_2$ can be chosen such that the water solubility of the compound of the invention is improved. This can be achieved by choosing $V_2$ to be a hydrophilic moiety. Alternatively, the $V_2$ moiety can be used to increase the residence time of the compound in the circulation, to reduce extravasation and excretion, and/or to reduce the immunogenicity of the compound. This can for example be achieved by choosing $V_2$ to be a polyethylene glycol or oligoethylene glycol or derivative thereof. When the moiety $V_2$ is a moiety that improves the pharmacokinetic properties of the compound of the invention and V, is a moiety that can be cleaved or transformed aspecifically, the compound solely serves to improve the properties of the one or more Z moieties, unless $L_2$ contains a targeting moiety.

In one embodiment, $V_2$ is a moiety that improves the pharmacokinetic properties and $V_1$ is a moiety that can be cleaved or transformed specifically.

In another embodiment, $V_2$ is an oligoethylene glycol or a polyethylene glycol or a derivative thereof and $V_1$ is a moiety that can be cleaved or transformed specifically.

In one embodiment, $V_2$ is a moiety that improves the pharmacokinetic properties and $V_1$ is a moiety that can be cleaved or transformed aspecifically.

In another embodiment, $V_2$ is an oligoethylene glycol or a polyethylene glycol or a derivative thereof and $V_1$ is a moiety that can be cleaved or transformed aspecifically.

In another embodiment, $V_2$ is an oligoethylene glycol or a polyethylene glycol or a derivative thereof and $V_1$ is a moiety that can be cleaved by ubiquitous enzymes.

In another embodiment, $V_2$ is an oligoethylene glycol or a polyethylene glycol or a derivative thereof and $V_1$ is a hydrolysable moiety.

It can be understood that the functional moiety $V_2$ can have several functional properties combined. For example, $V_2$ can be a moiety that improves the pharmacokinetic properties of a compound and at the same time be or contain a targeting moiety. As an additional example, $V_2$ can be a moiety that increases the aqueous solubility of the compound and at the same time be able to bind to for example a (functionalized) surface.

In one aspect of this invention, the compounds of this invention contain one or more functional groups that were protected during (a part of) the synthetic route towards said compounds. Said functional groups are deprotected before the reactive moiety is introduced. This means that in such a case, compounds (I) to (VI) do not contain any protecting groups.

In one embodiment, such a functional group is a primary or secondary amino group. Such a functional group may be located in $L_1$, Y, $V_1$, or Z, or in two or more of these moieties.

In one embodiment a compound of formula (I) or (II) contains one or more unprotected primary or secondary amino groups in $L_1$, Y, $V_1$, or Z.

In one embodiment a compound of formula (III) or (IV) contains one or more unprotected primary or secondary amino groups in $L_1$, Y, $V_1$, or Z.

In one embodiment a compound of formula (V) or (VI) contains one or more unprotected primary or secondary amino groups in $L_1$, Y, $V_1$, or Z.

In one embodiment, a compound of formula (III) is represented by

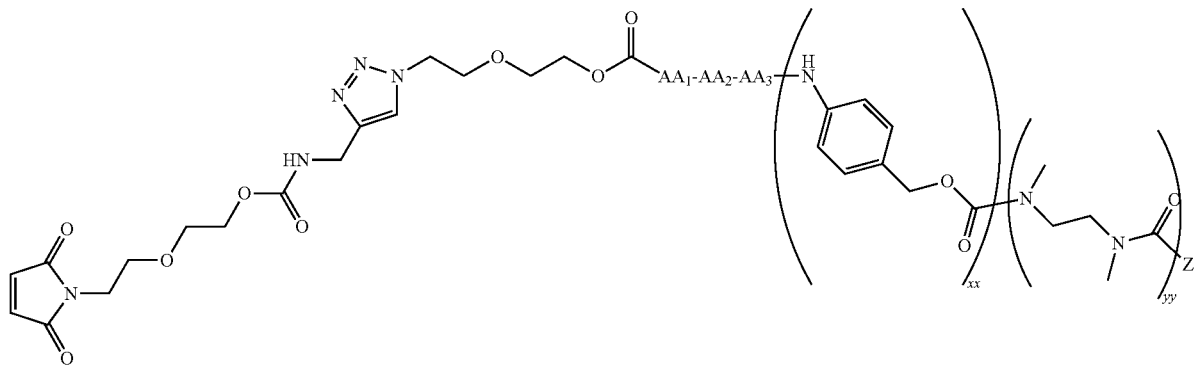

wherein $AA_1$-$AA_2$-$AA_3$ is a peptide wherein each of $AA_1$, $AA_2$, and $AA_3$ independently represents any natural or unnatural amino acid, xx is 1 or 2, yy is 0 or 1, and Z is as previously described.

In one embodiment, $AA_1$ is absent.

In another embodiment, $AA_1$-$AA_2$-$AA_3$ comprises a dipeptide selected from Val-Cit and Phe-Lys.

In a further embodiment, $AA_1$ is absent and $AA_2$-$AA_3$ is a dipeptide selected from Val-Cit and Phe-Lys.

In one embodiment, a compound of formula (IV) is represented by

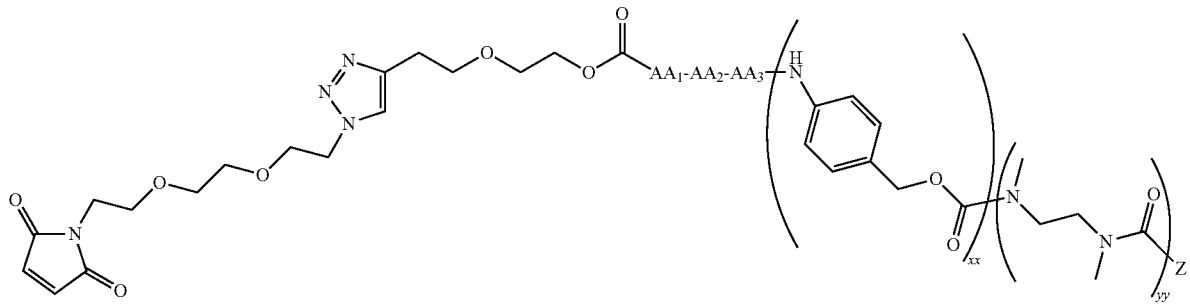

wherein $AA_1$-$AA_2$-$AA_3$ is a peptide wherein each of $AA_1$, $AA_2$, and $AA_3$ independently represents any natural or unnatural amino acid, xx is 1 or 2, yy is 0 or 1, and Z is as previously described.

In one embodiment, $AA_1$ is absent.

In another embodiment, $AA_1$-$AA_2$-$AA_3$ comprises a dipeptide selected from Val-Cit and Phe-Lys.

In a further embodiment, $AA_1$ is absent and $AA_2$-$AA_3$ is a dipeptide selected from Val-Cit and Phe-Lys.

In one embodiment, a compound of formula (III) is represented by

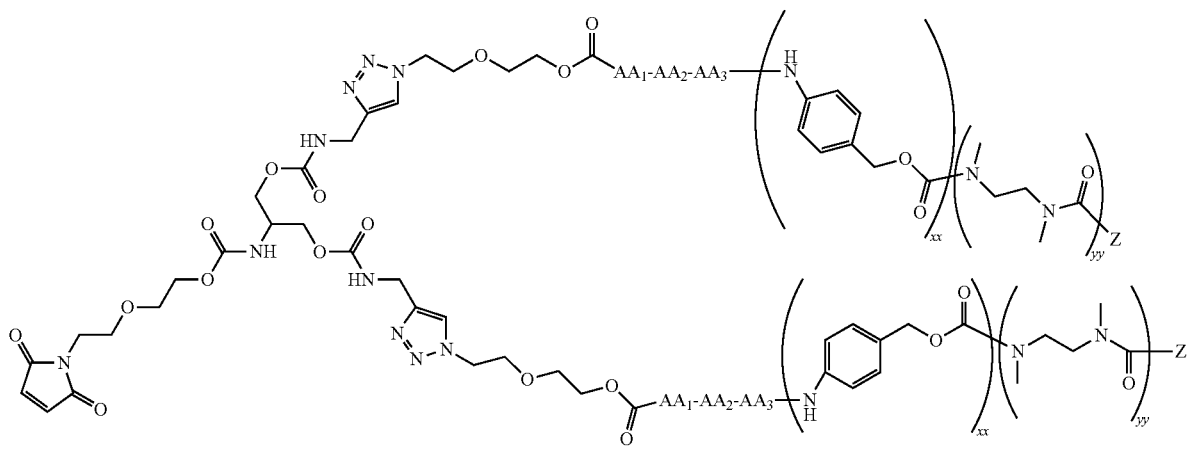

wherein each $AA_1$-$AA_2$-$AA_3$ is a peptide wherein each of $AA_1$, $AA_2$, and $AA_3$ independently represents any natural or unnatural amino acid, each xx is independently 1 or 2, each yy is independently 0 or 1, and each Z is as previously described.

In one embodiment, each $AA_1$ is absent.

In another embodiment, each $AA_1$-$AA_2$-$AA_3$ comprises a dipeptide independently selected from Val-Cit and Phe-Lys.

In a further embodiment, each $AA_1$ is absent and each $AA_2$-$AA_3$ is independently selected from Val-Cit and Phe-Lys.

In one embodiment, a compound of formula (III) is represented by

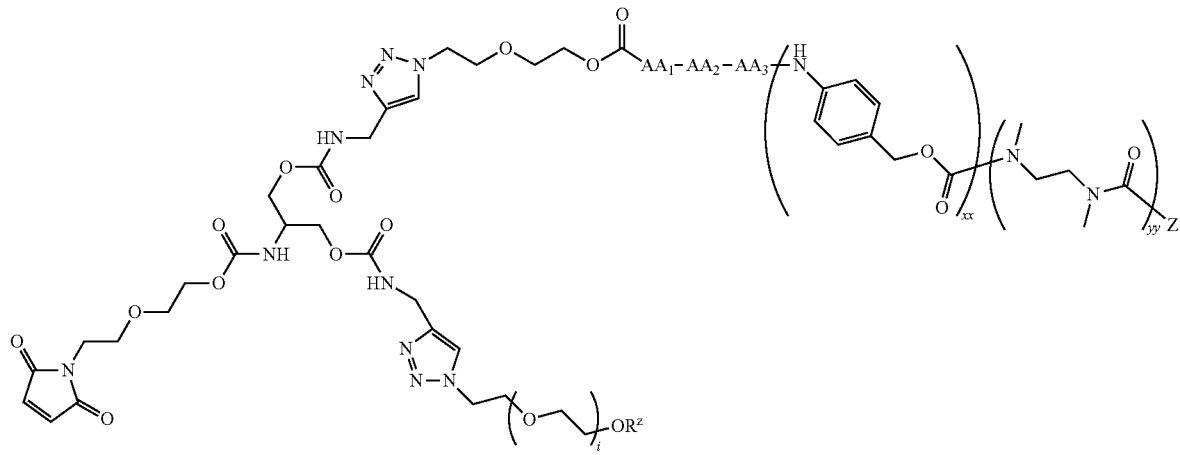

wherein $AA_1$-$AA_2$-$AA_3$ is a peptide wherein each of $AA_1$, $AA_2$, and $AA_3$ independently represents any natural or unnatural amino acid, xx is 1 or 2, yy is 0 or 1, $R^z$ is H or $C_{1-3}$ alkyl, ii is selected from 1 to 10000, and Z is as previously described.

In one embodiment, $AA_1$ is absent.

In another embodiment, $AA_1$-$AA_2$-$AA_3$ comprises a dipeptide selected from Val-Cit and Phe-Lys.

In a further embodiment, $AA_1$ is absent and $AA_2$-$AA_3$ is a dipeptide selected from Val-Cit and Phe-Lys.

In one embodiment, a compound of formula (I) is represented by

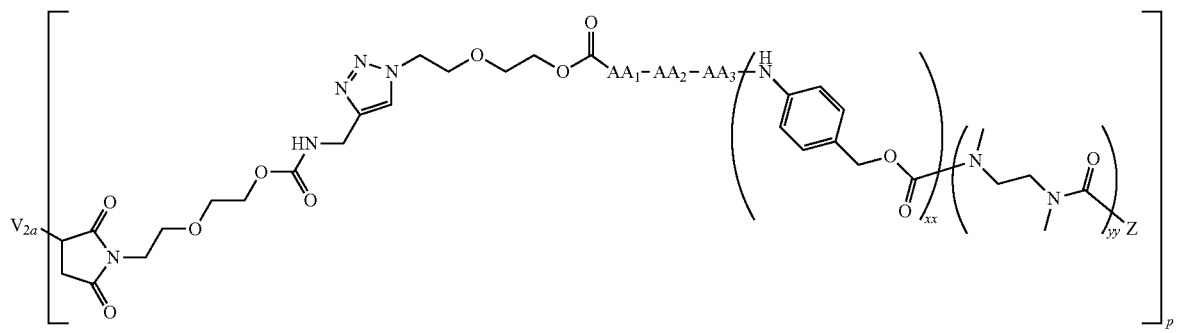

wherein $AA_1$-$AA_2$-$AA_3$ is a peptide wherein each of $AA_1$, $AA_2$, and $AA_3$ independently represents any natural or unnatural amino acid, xx is 1 or 2, yy is 0 or 1, $V_{2a}$ is an antibody or antibody fragment or a polymer, and p and Z are as previously described.

In one embodiment, $AA_1$ is absent.

In another embodiment, $AA_1$-$AA_2$-$AA_3$ comprises a dipeptide selected from Val-Cit and Phe-Lys.

In a further embodiment, $AA_1$ is absent and $AA_2$-$AA_3$ is a dipeptide selected from Val-Cit and Phe-Lys.

In one embodiment, a compound of formula (II) is represented by

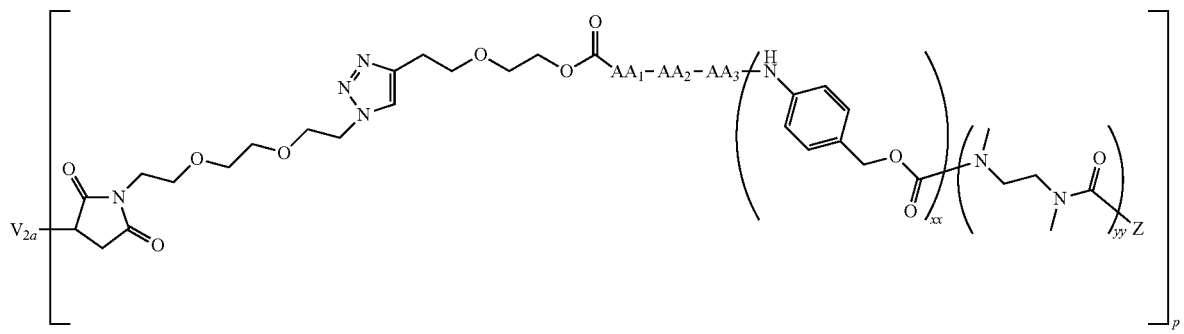

wherein $AA_1$-$AA_2$-$AA_3$ is a peptide wherein each of $AA_1$, $AA_2$, and $AA_3$ independently represents any natural or unnatural amino acid, xx is 1 or 2, yy is 0 or 1, $V_{2a}$ is an antibody or antibody fragment or a polymer, and p and Z are as previously described.

In one embodiment, $AA_1$ is absent.

In another embodiment, $AA_1$-$AA_2$-$AA_3$ comprises a dipeptide selected from Val-Cit and Phe-Lys.

In a further embodiment, $AA_1$ is absent and $AA_2$-$AA_3$ is a dipeptide selected from Val-Cit and Phe-Lys.

In one embodiment, a compound of formula (I) is represented by

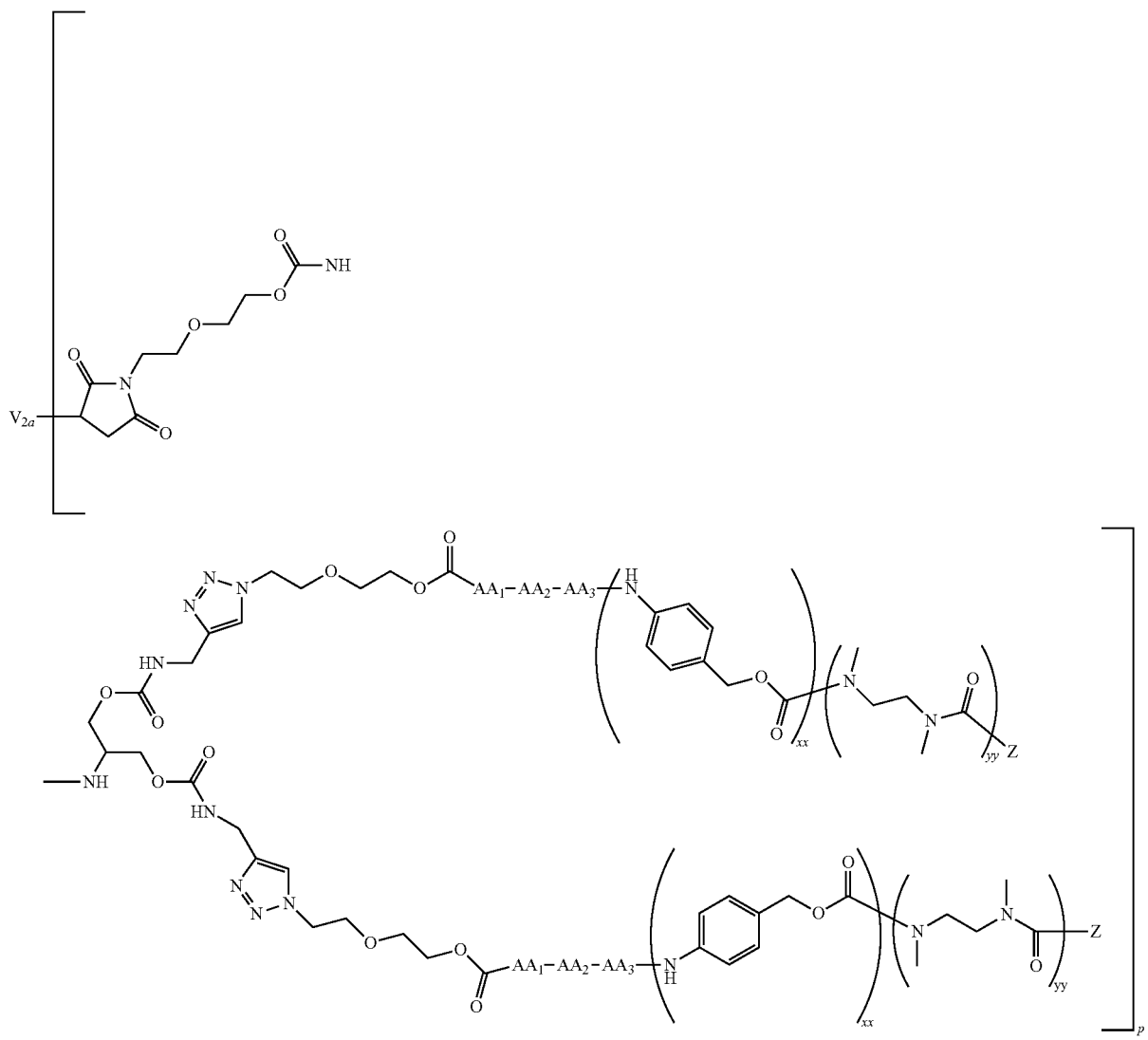

wherein each $AA_1$-$AA_2$-$AA_3$ is a peptide wherein each of $AA_1$, $AA_2$, and $AA_3$ independently represents any natural or unnatural amino acid, each xx is independently 1 or 2, each yy is independently 0 or 1, $V_{2a}$ is an antibody or antibody fragment or a polymer, and p and each Z are as previously described.

In one embodiment, each $AA_1$ is absent.

In another embodiment, each $AA_1$-$AA_2$-$AA_3$ comprises a dipeptide independently selected from Val-Cit and Phe-Lys.

In a further embodiment, each $AA_1$ is absent and each $AA_2$-$AA_3$ is independently selected from Val-Cit and Phe-Lys.

In one embodiment, a compound of formula (I) is represented by

In one embodiment, $AA_1$ is absent.

In another embodiment, $AA_1$-$AA_2$-$AA_3$ comprises a dipeptide selected from Val-Cit and Phe-Lys.

In a further embodiment, $AA_1$ is absent and $AA_2$-$AA_3$ is a dipeptide selected from Val-Cit and Phe-Lys.

Methods of Preparing Compounds of the Invention

As described in more detail below, compounds of formulae (I) and (II), as well as compounds of formulae (III) to (VI), are conveniently prepared in a way for some part analogous to compounds reported in for example WO 02/083180 and WO 2004/043493. The main structural difference is that compounds of formulae (I) and (II) contain a triazole ring. This has the advantages that due to its polarity, this moiety may contribute to increased water solubility, decreased aggrega-

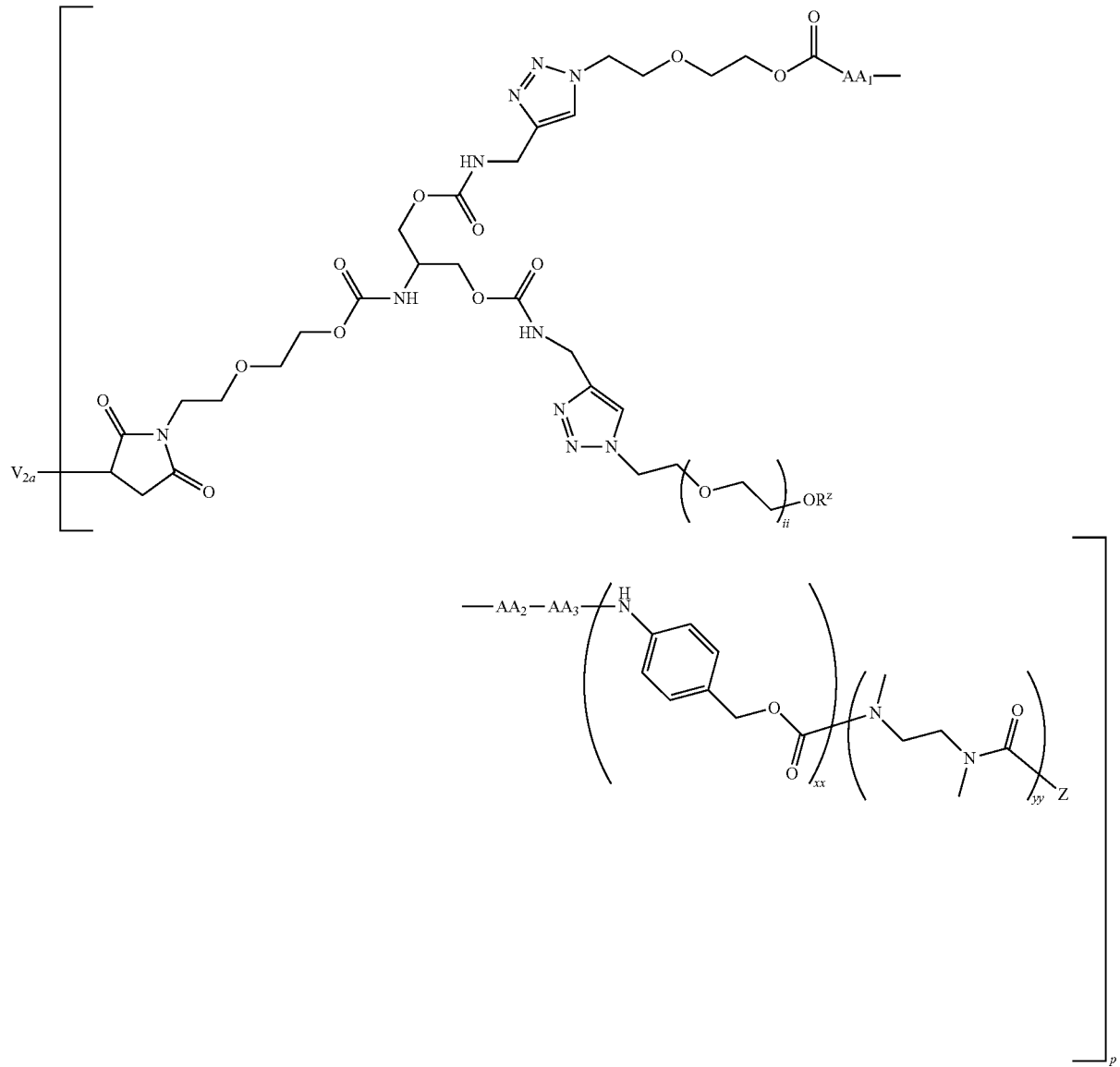

wherein $AA_1$-$AA_2$-$AA_3$ is a peptide wherein each of $AA_1$, $AA_2$, and $AA_3$ independently represents any natural or unnatural amino acid, xx is 1 or 2, yy is 0 or 1, $R^z$ is H or $C_{1-3}$ alkyl, ii is selected from 1 to 10000, and p and Z are as previously described.

tion, and improved pharmacokinetic properties of the conjugate, while at the same time the 1,4-substituted ring makes the linker more rigid and may keep it in a more extended form, thus keeping $V_2$ further away from the optional site of transformation or cleavage, which may favorably affect the release of Z, and keeping the one or more Z moieties further away from $V_2$, which may reduce shielding of $V_2$ and reduce blocking of $V_2$'s functionality.

The compounds of formulae (I) and (II) are prepared by means of a cycloaddition reaction between an alkyne moiety and an azide moiety. This offers several important advantages over the preparation of similar compounds without a triazole ring in the prior art, e.g., those described in WO 02/083180 and WO 2004/043493, as has been set forth in the summary of the invention hereinabove.

Huisgen 1,3-dipolar cycloadditions are exergonic fusion processes that unite two unsaturated reactants and provide fast access to an enormous variety of five-membered heterocycles. The cycloaddition of azides and alkynes to give 1,2,3-triazoles is arguably the most useful member of this family.[17] The uncatalyzed triazole-forming cycloaddition may require elevated temperatures and usually results in a mixture of the 1.4 and 1.5 regioisomers (FIG. 5).

Tornøe and colleagues were the first to report a Cu(I)-catalyzed cycloaddition between an azide and a terminal alkyne that could be carried out at room temperature and with complete 1.4 selectivity (FIG. 6).[18] Rostovtsev and co-workers reported similar findings slightly later.[19] Since then, many groups have used this "click" reaction for several purposes including drug discovery[20], molecular functionalization[21], library synthesis[22], and tagging or modification of live organisms and proteins[23,24,25].

It is noted that compounds of the invention (I)-(IV) are prepared by a 1,3-dipolar cycloaddition reaction between an alkyne and azide. Although this reaction, when carried out under "click" conditions, proceeds regioselectively, the regioisomeric compounds of compounds (I)-(IV) are not excluded from this invention.

In the syntheses of compounds of the invention, the click reaction between an azide and terminal alkyne is applied according to a conceptually novel approach: the click reaction is used to transform a protecting group (azide-L, or alkyne-$L_1$) into a reactive moiety (RM-$L_2$-triazole-$L_1$)[10] in a single step. The moiety azide-L, or alkyne-L, protects a functional group on $V_1$/Y throughout (a part of) the synthesis of a compound of formula (V) or (VI). It can then be efficiently transformed into the moiety RM-$L_2$-triazole-L, under very mild conditions in a single step.

In the summary of the invention hereinabove the method according to the invention is already defined. It should be noted that the scope and embodiments provided for compounds of this invention are also applicable to the method claims provided in this specification and the appended claims. Thus with respect to the method according to the invention, $V_2$, $L_3$, $L_2$, $L_1$, V, Y, Z, p, q, r, s, and z have the same scope and specifications as described hereinabove with respect to the compounds according to the invention.

In one embodiment, a compound of formula (I) is prepared from a compound of formula (V) via a compound of formula (III).

In another embodiment, a compound of formula (II) is prepared from a compound of formula (VI) via a compound of formula (IV).

In one embodiment, in the method of this invention said fourth compound is a compound of formula (I) or (II).

In one embodiment, in the method of this invention said third compound is a compound of formula (III) or (IV).

In one embodiment, in the method of this invention said first compound is a compound of formula (V) or (VI).

In one embodiment, in the method of this invention said fourth compound is a compound of formula (I) or (II) wherein Y is a self-elimination spacer system.

In still a further embodiment, in the method of this invention said fourth compound is a compound of formula (I) or (II) wherein the spacer system Y is selected from

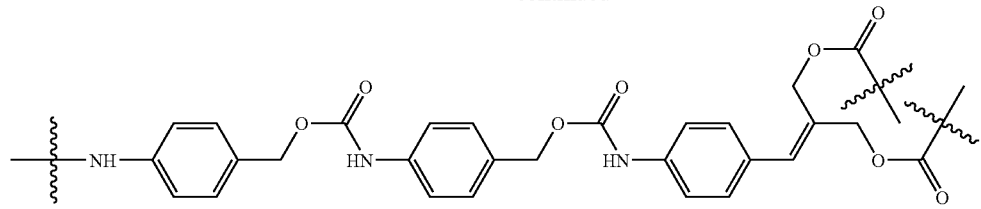
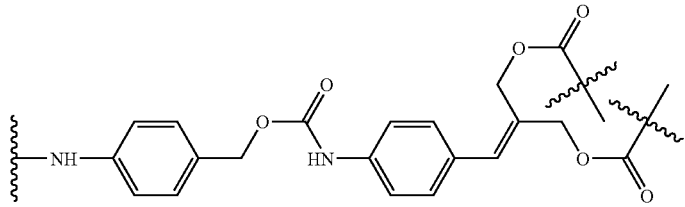
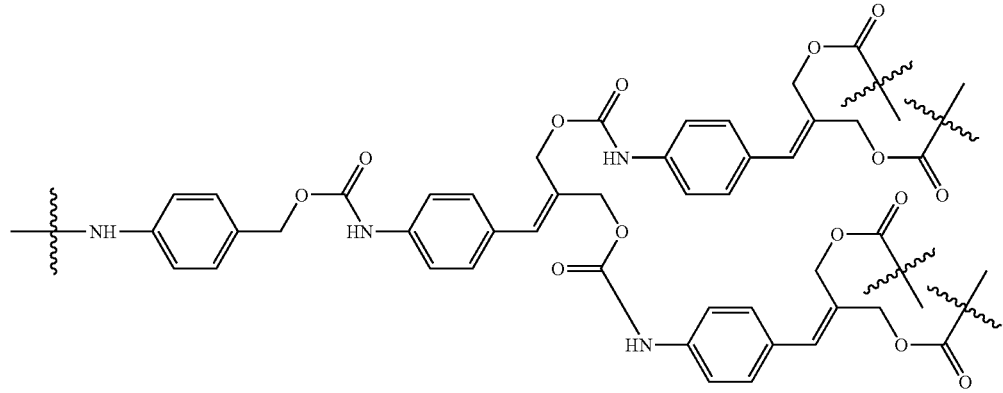
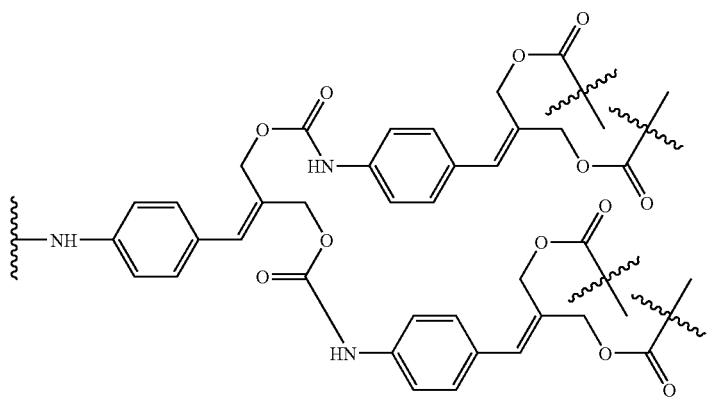
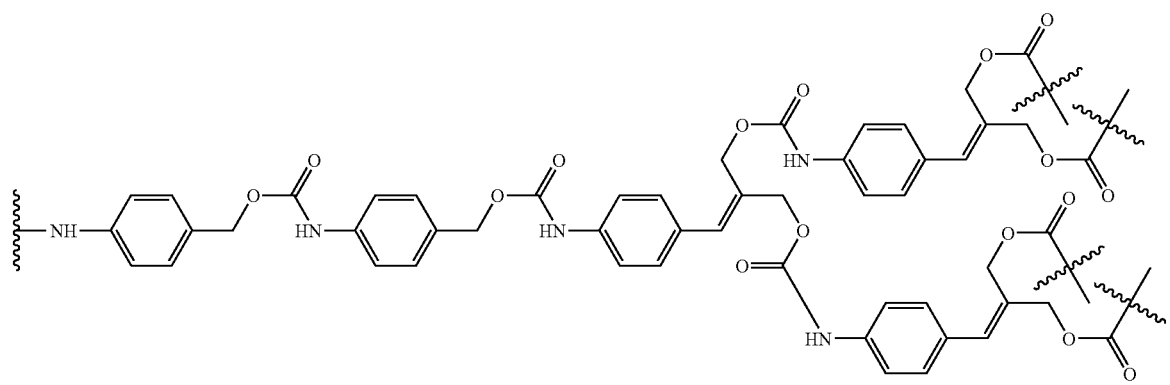

and from the formulae depicted above that further comprise one or more co-amino aminocarbonyl cyclization spacers connected to the right-hand side of the formulae.

In another embodiment, in the method of this invention said fourth compound is a compound of formula (I) or (II) wherein $V_1$ contains a substrate that can be cleaved by plasmin, a cathepsin, cathepsin B, β-glucuronidase, prostate-specific antigen (PSA), urokinase-type plasminogen activator (u-PA), a member of the family of matrix metalloproteinases, an enzyme localized by means of directed enzyme prodrug therapy, such as ADEPT, VDEPT, MDEPT, GDEPT, or PDEPT, or wherein $V_1$ contains a nitro(hetero)aromatic moiety that can be cleaved or transformed by reduction under hypoxic conditions or by reduction by a nitroreductase.

Furthermore, in another embodiment, in the method of this invention said fourth compound is a compound of formula (I) or (II) wherein one or more moieties Z are therapeutic agents.

In another embodiment, in the method of this invention said fourth compound is a compound of formula (I) or (II) wherein the moieties Z comprise at least two different therapeutic moieties.

Further, in another embodiment, in the method of this invention said fourth compound is a compound of formula (I) or (II) wherein the moieties Z each are independently an antibiotic, an anti-bacterial agent, an antimicrobial agent, an anti-inflammatory agent, an anti-infectious disease agent, an anti-autoimmune disease agent, an anti-viral agent, or an anticancer agent.

In another embodiment, in the method of this invention said fourth compound is a compound of formula (I) or (II) wherein the moieties Z are each an anticancer agent.

In another embodiment, in the method of this invention said fourth compound is a compound of formula (I) or (II) wherein $L_1$ is

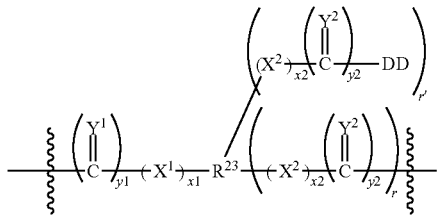

wherein
$X^1, Y^1$ are each independently O, $NR^{24}$, or S;
Each $X^2, Y^2$ are each independently O, $NR^{25}$, or S;
Each y1, y2, x1, and x2 are independently 0 or 1;
r is an integer selected from 1 (included) to 128 (included);
r' is an integer selected from 0 (included) to 127 (included); r+r'≦128;
Each DD is independently H, OH, or a leaving group;
$R^{23}$ is absent or is either a dendritic, branched or unbranched moiety and selected from optionally substituted alkylene or polyalkylene, optionally substituted heteroalkylene or polyheteroalkylene, optionally substituted arylene or polyarylene, optionally substituted heteroarylene or polyheteroarylene, optionally substituted cycloalkylene or polycycloalkylene, optionally substituted heterocycloalkylene or polyheterocycloalkylene, —(CH$_2$CH$_2$O)$_v$—, -alkylene-(CH$_2$CH$_2$O)$_v$—, —(CH$_2$CH$_2$O)$_v$-alkylene-, -alkylene-(CH$_2$CH$_2$O)$_v$-alkylene-, -heteroalkylene-(CH$_2$CH$_2$O)$_v$—, —(CH$_2$CH$_2$O)$_v$-heteroalkylene-, -heteroalkylene-(CH$_2$CH$_2$O)$_v$-alkylene-, -heteroalkylene-(CH$_2$CH$_2$O)$_v$-heteroalkylene-, -alkylene-(CH$_2$CH$_2$O)$_v$-heteroalkylene-, a dendritic structure, or an oligopeptide, or any combination of two or more of the above;
$R^{24}$ and $R^{25}$ are independently selected from H and alkyl;
v is selected from 1 (included) to 500 (included).

In another embodiment, in the method of this invention said fourth compound is a compound of formula (I) or (II) wherein $L_2$ is

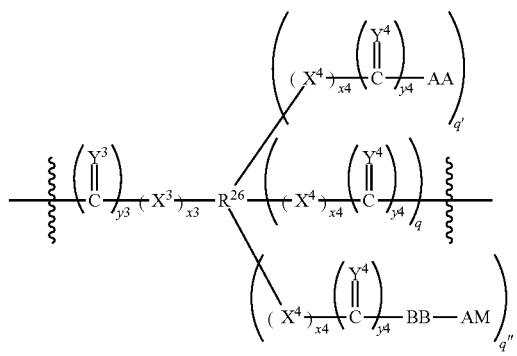

wherein
$X^3, Y^3$ are each independently O, $NR^{27}$, or S;
Each $X^4, Y^4$ are each independently O, $NR^{28}$, or S;
AA is either an azide or an acetylene group;
BB is a 1,4-substituted 1,2,3-triazole;
Each AM is independently an adjuvant moiety;
Each y3, y4, x3, and x4 are independently 0 or 1;
q is an integer selected from 1 (included) to 128 (included) and q' and q" are integers independently selected from 0 (included) to 127 (included) with q+q'+q"≦128;
$R^{26}$ is absent or is either a dendritic, branched or unbranched moiety and selected from optionally substituted alkylene or polyalkylene, optionally substituted heteroalkylene or polyheteroalkylene, optionally substituted arylene or polyarylene, optionally substituted heteroarylene or polyheteroarylene, optionally substituted cycloalkylene or polycycloalkylene, optionally substituted heterocycloalkylene or polyheterocycloalkylene, —(CH$_2$CH$_2$O)$_v$—, -alkylene-(CH$_2$CH$_2$O)$_v$—, —(CH$_2$CH$_2$O)$_v$-alkylene-, -alkylene-(CH$_2$CH$_2$O)$_v$-alkylene-, -heteroalkylene-(CH$_2$CH$_2$O)$_v$—, —(CH$_2$CH$_2$O)$_v$-heteroalkylene-, -heteroalkylene-(CH$_2$CH$_2$O)$_v$-alkylene-, -heteroalkylene-(CH$_2$CH$_2$O)$_v$-heteroalkylene-, -alkylene-(CH$_2$CH$_2$O)$_v$-heteroalkylene-, a dendritic structure, or an oligopeptide, or any combination of two or more of the above;
$R^{27}$ and $R^{28}$ are independently selected from H and alkyl;
v is selected from 1 (included) to 500 (included).

In another embodiment, in the method of this invention said fourth compound is a compound of formula (I) or (II) wherein the moiety $L_3$ is

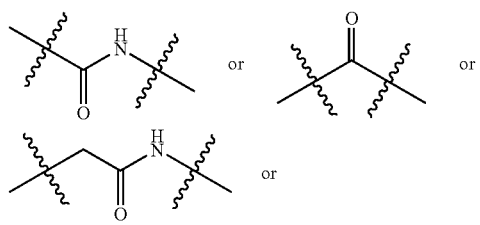

-continued

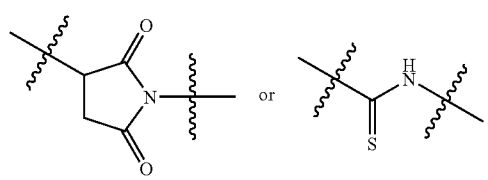 or 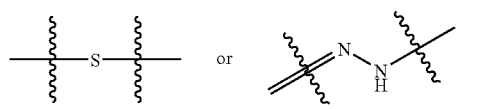 or

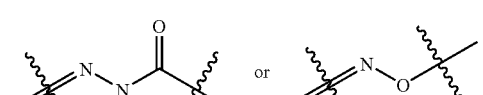 or 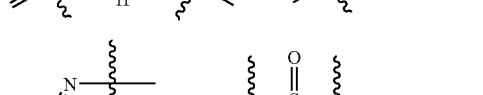 or

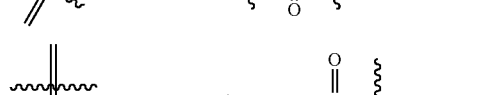 or 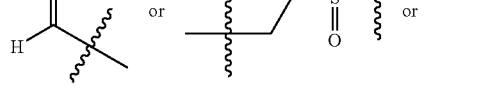 or

 or  or

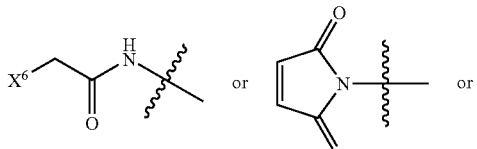 or

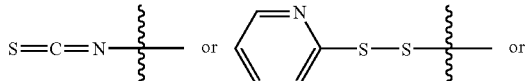

-continued

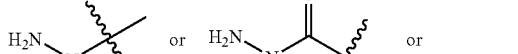 or 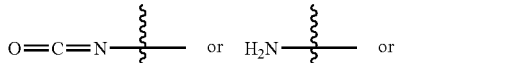 or

 or 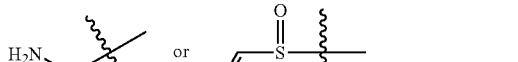 or

 or 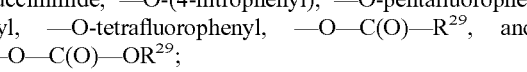 or

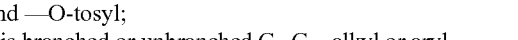 or 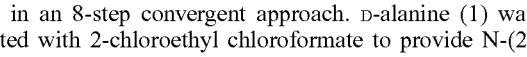 or

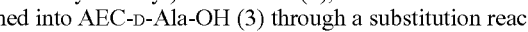 or 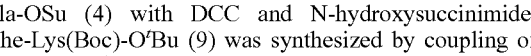 or 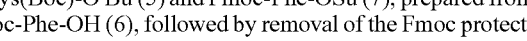 or

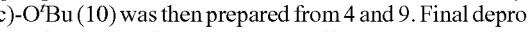 or 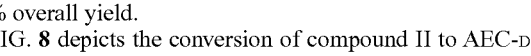

Furthermore, in one embodiment in the method of this invention said fourth compound is a compound of formula (I) or (II) wherein the moiety $V_2$ is a targeting moiety and is selected from the group consisting of a protein or protein fragment, an antibody or an antibody fragment, a receptor-binding or peptide vector moiety, and a polymeric or dendritic moiety, or any combination thereof.

In addition, in one embodiment in the method of this invention said fourth compound is a compound of formula (I) or (II) wherein $V_2$ is an antibody or antibody fragment.

In another embodiment, in the method of this invention said fourth compound is a compound of formula (I) or (II) wherein $V_2$ is a receptor-binding moiety.

In another embodiment, in the method of this invention said fourth compound is a compound of formula (I) or (II) wherein $V_2$ is a polymer.

In yet another embodiment, in the method of this invention said fourth compound is a compound of formula (I) or (II) wherein $V_2$ is an oligoethylene glycol or a polyethylene glycol or a derivative thereof.

In another embodiment, in the method of this invention said third compound is a compound of the formula (III) or (IV) wherein the reactive moiety RM is

 or 

wherein $X^5$ is selected from —Cl, —Br, —I, —F, —OH, —O—N-succinimide, —O-(4-nitrophenyl), —O-pentafluorophenyl, —O-tetrafluorophenyl, —O—C(O)—$R^{29}$, and —O—C(O)—O$R^{29}$;

$X^6$ is selected from —Cl, —Br, —I, —O-mesyl, —O-triflyl, and —O-tosyl;

$R^{29}$ is branched or unbranched $C_1$-$C_{10}$ alkyl or aryl.

Figure 7:
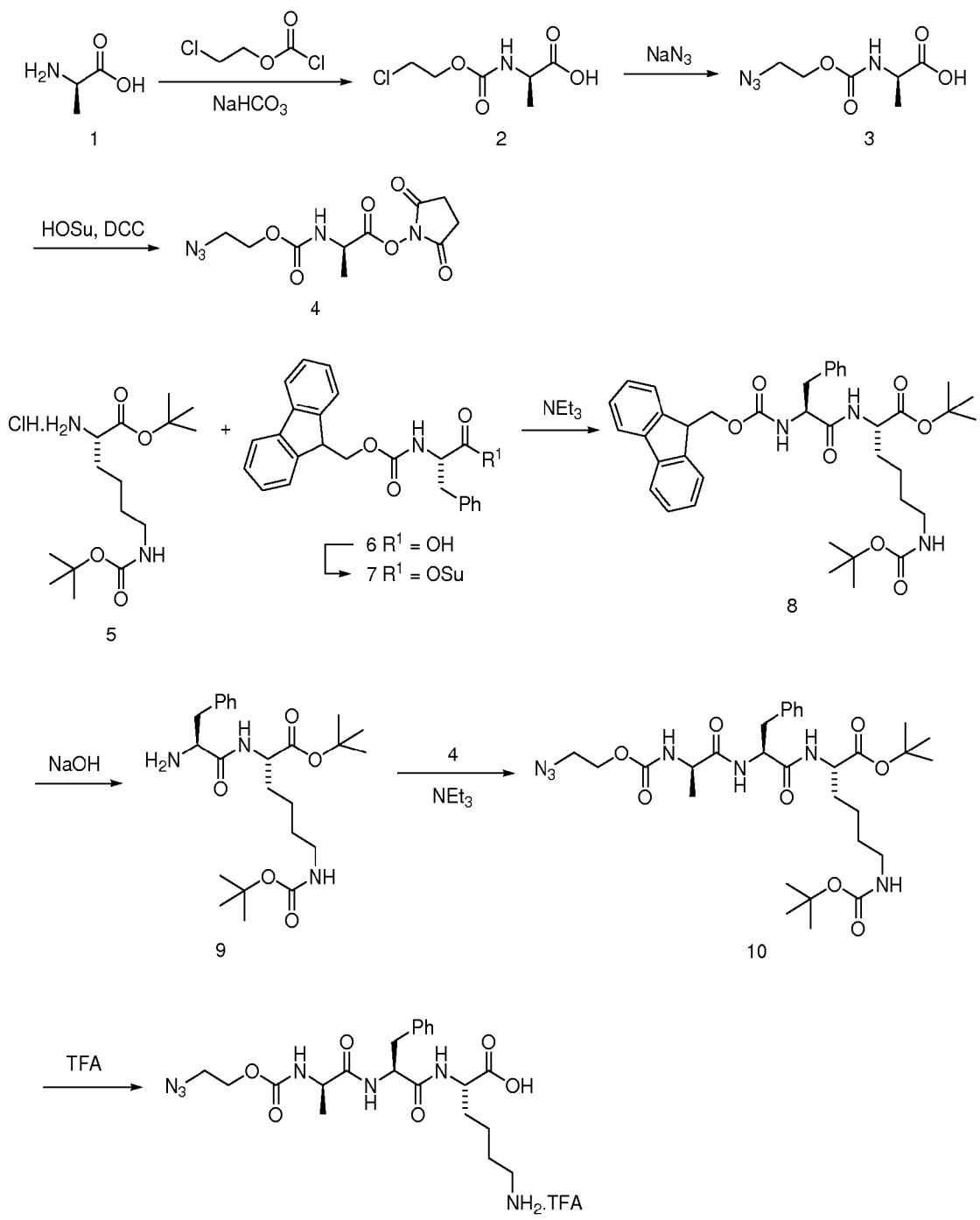
FIG. 7 depicts the synthesis of AEC-D-Ala-Phe-Lys-OH (11).

FIG. 7 depicts the synthesis of AEC-D-Ala-Phe-Lys-OH (11) in an 8-step convergent approach. D-alanine (1) was reacted with 2-chloroethyl chloroformate to provide N-(2-chloroethoxycarbonyl)-D-Ala-OH (2), which was transformed into AEC-D-Ala-OH (3) through a substitution reaction with sodium azide in DMF and then activated to AEC-D-Ala-OSu (4) with DCC and N-hydroxysuccinimide. H-Phe-Lys(Boc)-O$^t$Bu (9) was synthesized by coupling of H-Lys(Boc)-O$^t$Bu (5) and Fmoc-Phe-OSu (7), prepared from Fmoc-Phe-OH (6), followed by removal of the Fmoc protecting group in 8 under basic conditions. AEC-D-Ala-Phe-Lys (Boc)-O$^t$Bu (10) was then prepared from 4 and 9. Final deprotection of 10 with trifluoroacetic acid afforded compound II in 52% overall yield.

Figure 8:
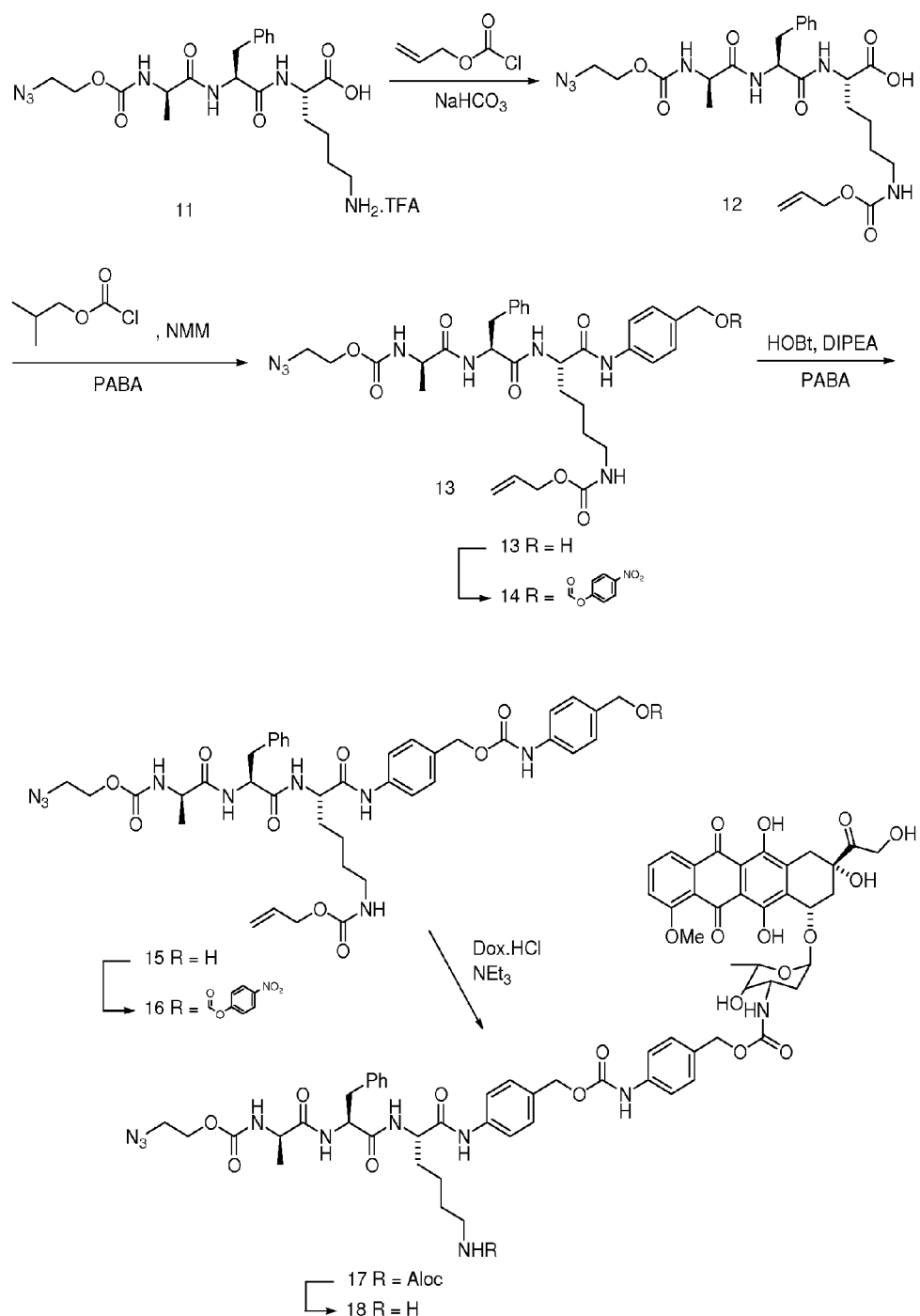
FIG. 8 depicts the synthesis of AEC-D-Ala-Phe-Lys-PABC-PABC-Dox (18).

FIG. 8 depicts the conversion of compound II to AEC-D-Ala-Phe-Lys-PABC-PABC-Dox (18). First, compound II was protected at the ε-amino group of the lysine with an Aloc group. Compound 12 was then activated with isobutyl chloroformate and next reacted with p-aminobenzyl alcohol to provide AEC-D-Ala-Phe-Lys-PABA (13). Activation with p-nitrophenyl chloroformate to give 14 and subsequent HOBt-catalyzed coupling with p-aminobenzyl alcohol gave 15. This was activated again with p-nitrophenyl chloroformate to provide AEC-D-Ala-Phe-Lys-PABC-PABC-PNP (16). Coupling of doxorubicin to 16 in N-methylpyrrolidinone provided 17. Deprotection of the 1-amino group of the lysine provided 18 in 22% yield from 11.

Figure 9:
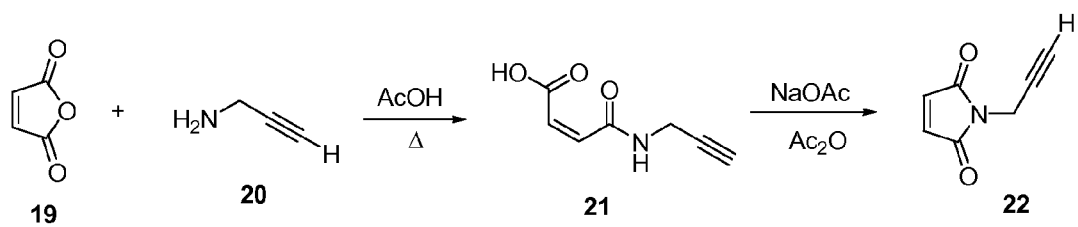
FIG. 9 depicts the synthesis of N-propargylmaleimide (22).

FIG. 9 depicts the preparation of N-propargylmaleimide (22) from maleic anhydride (19) in two steps. Maleic anhydride was reacted with propargylamine (20) in refluxing acetic acid to afford maleamic acid 21 which was then converted to 22 with sodium acetate in acetic anhydride. Compound 22 was obtained in 46% yield.

Figure 10:
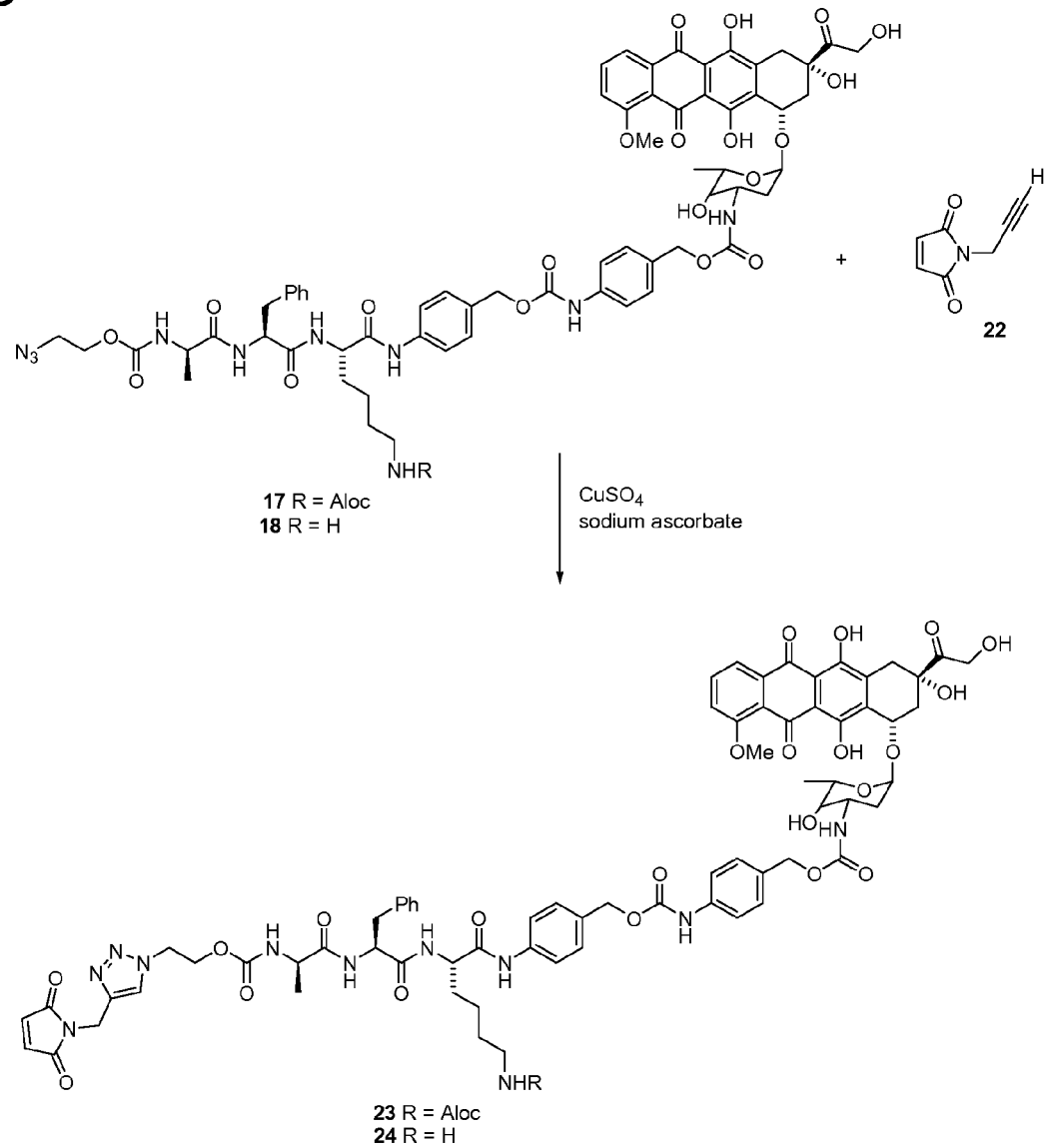
FIG. 10 depicts the reactions of compounds 17 and 18 with N-propargylmaleimide (22).

The click reactions between compounds 17 and 22, and 18 and 22 are depicted in FIG. 10.

Uses, Methods, and Compositions

In one aspect, this invention relates to use of a compound of formula (V) or (VI) for the preparation of a compound of formula (III) or (IV), respectively.

In another aspect, this invention relates to use of a compound of formula (V) or (VI) for the preparation of a compound of formula (I) or (II), respectively.

In yet another aspect, this invention relates to use of a compound of formula (III) or (IV) for the preparation of a compound of formula (I) or (II), respectively.

In yet another aspect, the invention relates to the use of any of the compounds defined above for the manufacture of a pharmaceutical preparation for the treatment or diagnosis of a mammal being in need thereof. In one embodiment, the invention relates to the use of any of the compounds defined above for the manufacture of a pharmaceutical composition for the treatment of a tumor in a mammal.

Also the invention relates to any of the compounds defined above as a medicament or an active component or active substance in a medicament.

In a further aspect the invention relates to a method for preparing a pharmaceutical composition containing a compound as defined above, to provide a solid or a liquid formulation for administration orally, topically, or by injection. Such a method or process at least comprises the step of mixing the compound with a pharmaceutically acceptable carrier.

In one aspect, this invention relates to a method to affect or prevent a predefined condition by exerting a certain effect, or detect a certain condition using a compound of the present invention, or a (pharmaceutical) composition comprising a compound of this invention.

In one embodiment, this invention relates to a method of detecting the presence of a certain condition, e.g., the presence of an enzyme, the presence of a certain pH, the presence of a (bio)molecule, the presence of a substrate, or the presence of a certain oxygen concentration, with a compound of this invention, either in vivo or ex vivo.

In one embodiment, this invention relates to a method of determining an enzyme ex vivo, e.g., in a diagnostic assay, using a compound of this invention by incubating a sample (possibly) containing said enzyme with a compound of this invention containing one or more diagnostic moieties Z and a substrate for said (proteolytic) enzyme, and observing release of said Z moieties. The phrase "determining an enzyme" means both qualitative analysis, i.e., detecting the presence of the enzyme, determining whether it is present, and quantitative analysis, i.e., quantifying the enzyme, determining the enzyme activity present in the sample. An enzyme can also be indirectly determined via its pro-enzyme containing a recognition site, e.g., an activation site, cleavable by said enzyme to be determined. Cleavage of the pro-enzyme can in such case be detected by observing the resulting activity using a suitable compound of the present invention.

In one embodiment the invention relates to a diagnostic assay method (in vivo or ex vivo) in which a compound according to the invention is used.

In a further embodiment the invention relates to a method in which the presence or amount of an enzyme is determined by using a compound according to the invention.

In one embodiment, this invention relates to a method to affect or prevent a predefined condition, e.g., a disease such as an autoimmune disease, a microbial disease, or cancer, by exerting an effect using a compound of this invention.

In a further embodiment, the invention relates to a method of treating a mammal being in need thereof, whereby the method comprises the administration of a pharmaceutical composition to the mammal in a therapeutically effective dose.

In a further embodiment, this invention relates to a method of treating a mammal having an illness characterized by undesired (cell) proliferation with a compound of this invention. In another embodiment this invention relates to a method of treating a mammal carrying a tumor with a compound of this invention. In yet another embodiment this invention relates to a method of treating a mammal having an inflammatory disease with a compound of this invention. In yet another embodiment this invention relates to a method of treating a mammal having an autoimmune disease with a compound of this invention. In yet another embodiment this invention relates to a method of treating a mammal having a bacterial or microbial infection with a compound of this invention.

In one embodiment, the invention relates to a method of treating cancer in a mammal, whereby the method comprises the administration of a pharmaceutical composition to the mammal in a therapeutically effective dose.

In one embodiment, a compound of the invention is used to treat an illness characterized by undesired proliferation. In another embodiment, a compound of the invention is used to treat an illness characterized by undesired (cell) proliferation. In another embodiment, a compound of the invention is used to treat a tumor. In yet another embodiment, a compound of the invention is used to treat an inflammatory disease. In yet another embodiment a compound of the invention is used to treat an autoimmune disease. In yet another embodiment a compound of the invention is used to treat a bacterial or microbial infection.

The invention also relates to pharmaceutical compositions comprising the compounds of the invention as defined above. A compound of the invention may be administered in purified form together with a pharmaceutical carrier as a pharmaceutical composition. The preferred form depends on the intended mode of administration and therapeutic or diagnostic application. The pharmaceutical carrier can be any compatible, nontoxic substance suitable to deliver the compounds of the invention to the patient. Pharmaceutically acceptable carriers are well known in the art and include, for example, aqueous solutions such as (sterile) water or physiologically buffered saline or other solvents or vehicles such as glycols, glycerol, oils such as olive oil or injectable organic esters, alcohol, fats, waxes, and inert solids. A pharmaceutically acceptable carrier may further contain physiologically acceptable compounds that act for example to stabilize or to increase the absorption of the compounds of the invention. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. Pharmaceutically acceptable adjuvants, buffering agents, dispersing agents, and the like, may also be incorporated into the pharmaceutical compositions.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The compounds of the invention are however preferably administered parenterally. Preparations of the compounds of the invention for parenteral administration must be sterile. Sterilization is readily accomplished by filtration through sterile filtration membranes, optionally prior to or following lyophilization and reconstitution. The parenteral route for administration of compounds of the invention is in accord with known methods, e.g. injection or infusion by intravenous, intraperitoneal, intramuscular, intraarterial, or intralesional routes. The compounds of the invention may be administered continuously by infusion or by bolus injection. A typical composition for intravenous infusion could be made up to contain 100 to 500 ml of sterile 0.9% NaCl or 5% glucose optionally supplemented with a 20% albumin solution and 1 mg to 10 g of the compound of the invention, depending on the particular type of compound of the invention and its required dosing regime. Methods for preparing parenterally administrable compositions are well known in the art and described in more detail in various sources, including, for example, Remington's Pharmaceutical Science[26].

The invention is further exemplified by the following Examples. These examples are for illustrative purposes only and are not intended to limit the scope of the invention.

EXAMPLES

Example 1

N-(2-Chloroethyloxycarbonyl)-D-Ala-OH (2): To a solution of $NaHCO_3$ (9.43 g, 112 mmol) and H-D-Ala-OH (2.0 g, 22.5 mmol) in water (110 mL) was slowly added a solution of 2-chloroethyl chloroformate (2.55 mL, 24.7 mmol) in dioxane (100 mL). The reaction mixture was stirred overnight. Dioxane was removed by evaporation and the resulting aqueous solution was acidified with 1 N HCl to pH=3. The solution was extracted three times with ethyl acetate (3×175 mL). The combined organic layers were dried over $Na_2SO_4$, filtered, and concentrated to dryness, which gave 2 (4.29 g, 21.9 mmol, 97%) as a viscous oil. $^1$H NMR (300 MHz, $CDCl_3$) δ: 1.49 ppm (d, 3H, J=7.2 Hz, $CH_3$-Ala), 3.68 (t, 2H, J=5.7 Hz, $CH_2Cl$), 4.32-4.42 (m, 3H, $CH_2OR$+α–H).

Example 2

N-(2-azidoethyloxycarbonyl)-D-Ala-OH (AEC-D-Ala-OH, 3): To a solution of 2 (4.29 g, 21.9 mmol) in DMF (150 mL) was added sodium azide (1.57 g, 24.1 mmol). The reaction mixture was heated and stirred for 48 h. The reaction mixture was then cooled down to room temperature and concentrated to dryness. Chloroform (50 mL) was added to the oily residue and the resulting suspension was filtered. The filter was rinsed with chloroform (2×10 mL), and the combined filtrate was concentrated. After prolonged drying in vacuo crude 3 (5.80 g, max. 21.9 mmol, 100%) was obtained as an oil. $^1$H NMR (300 MHz, $CDCl_3$) δ: 1.31 (d, 3H, J=6.6 Hz, $CH_3$-Ala), 3.44 (t, 2H, J=5.1 Hz, $CH_2N_3$), 4.03-4.22 (m, 3H, α-H+ $CH_2OR$).

Example 3

Fmoc-Phe-Lys(Boc)-O$^t$Bu (8): To a suspension of Fmoc-Phe-OH (6, 5.00 g, 12.9 mmol) in dichloromethane (100 mL) were added HOSu (1.56 g, 13.6 mmol) and DCC (2.93 g, 14.2 mmol). The resulting suspension was stirred at room temperature for 3 h. Then, triethylamine (1.83 mL, 13.2 mmol) and H-Lys(Boc)-O$^t$Bu.HCl (4.46 g, 13.2 mmol) were added consecutively, and the resulting suspension was stirred overnight. The reaction mixture was filtered, and the filtrate was washed with 10% aqueous citric acid, water, a saturated aqueous $NaHCO_3$ solution, and brine. The organic layer was dried over $Na_2SO_4$, filtered, and concentrated. This gave crude 8 (8.97 g, max. 12.91 mmol, 100%) as a white solid. $^1$H NMR (300 MHz, $CDCl_3$) δ: 1.10-1.90 (m, 6H, $CH_2$-Lys), 1.41 (s, 18H, $^t$Bu), 3.01-3.15 (m, 4H, N—$CH_2$-Lys+$CH_2$-Phe), 4.19 (t, 1H, J=6.8 Hz, CH-Fmoc), 4.25-4.55 (m, 4H, 2×α-H+ $CH_2$-Fmoc), 7.19-7.35 (m, 7H, $H_{Ar}$), 7.38 (t, 2H, J=7.4 Hz, $H_{Ar}$), 7.51 (m, 2H, $H_{Ar}$), 7.72 (d, 2H, J=7.5 Hz, $H_{Ar}$).

Example 4

H-Phe-Lys(Boc)-O$^t$Bu (9): To a solution of 8 (8.97 g, max. 12.91 mmol) in dioxane/methanol (190 mL, 14:5 v/v) was added 2 N aqueous NaOH (10 mL). The reaction mixture was stirred at room temperature for 1 h. The reaction mixture was then neutralized with acetic acid (1.5 mL). The mixture was concentrated to 15 mL, dioxane (20 mL) was added, and the resulting mixture was freeze-dried. Diisopropyl ether (100 mL) was added to the residue; the resulting suspension was stirred for 30 min and filtered. The residue was rinsed with more diisopropyl ether (2×50 mL), and the combined filtrate was concentrated to dryness. This gave crude 9 (7.92 g, max. 12.91 mmol, 100%) as a viscous oil. $^1$H-NMR (300 MHz, $CDCl_3/CD_3OD$) δ: 1.25-1.88 (m, 6H, $CH_2$-Lys), 1.44 (s, 9H, $^t$Bu), 1.47 (s, 9H, $^t$Bu), 2.78 (dd, 1H, J, =8.7 Hz, $J_2$=13.5 Hz, $CH_2$-Phe), 3.06 (m, 2H, N—$CH_2$-Lys), 3.16 (dd, 1H, $J_1$=13.5 Hz, $J_2$=4.5 Hz, $CH_2$-Phe), 3.65 (m, 1H, α-H), 4.37 (m, 1H, α-H), 7.22-7.34 (m, 5H, $H_{Ar}$).

Example 5

AEC-D-Ala-Phe-Lys(Boc)-O$^t$Bu (10): To a solution of 3 (1.51 g, max. 7.2 mmol) in dichloromethane (50 mL) were added HOSu (865 mg, 7.52 mmol) and DCC (1.62 g, 7.87 mmol). The reaction mixture was stirred at room temperature for 3 h. The reaction mixture was cooled to 0° C., and 9 (4.85 g, max. 7.87 mmol) and triethylamine (1.09 mL, 7.87 mmol) were added to the reaction mixture. The reaction mixture was stirred at room temperature overnight. The suspension was filtered, the residue rinsed with dichloromethane, and the combined filtrate washed with 10% aqueous citric acid, water, a saturated aqueous $NaHCO_3$ solution, and brine, dried over $Na_2SO_4$, filtered, and concentrated to dryness. Column chromatography (Ethyl acetate/heptanes=1/1) gave 10 (2.64 g, 4.17 mmol, 58%) as a white solid. $^1$H NMR (300 MHz, $CDCl_3/CD_3OD$) δ: 1.11-1.90 (m, 6H, $CH_2$-Lys), 1.19 (d, 3H, J=6.9 Hz, CH$_3$-Ala), 1.44 (s, 9H, $^t$Bu), 1.46 (s, 9H, $^t$Bu), 2.94 (dd, 1H, J$_1$=9.0 Hz, J$_2$=13.5 Hz, CH$_2$-Phe), 3.05 (m, 2H, CH$_2$-Lys), 3.20 (dd, 1H, J, =4.8 Hz, J$_2$=13.8 Hz, CH$_2$-Phe), 3.46 (m, 2H, CH$_2$N$_3$), 4.05-4.33 (m, 4H, CH$_2$OR+2×α-H), 4.62 (m, 1H, α-H), 7.16-7.27 (m, 5H, H$_{Ar}$).

Example 6

AEC-D-Ala-Phe-Lys-OH (11): To a solution of 10 (2.19 g, 3.45 mmol) in chloroform (15 mL) was added dropwise at 0° C. a 1:1 mixture of chloroform and trifluoroacetic acid (15 mL). The reaction temperature was increased to room temperature and the reaction mixture was stirred overnight. The reaction mixture was concentrated to dryness. Diethyl ether (25 mL) was added to the residue and the resulting suspension was vigorously stirred for 5 h. The solid was filtered off, rinsed with more diethyl ether, collected, and dried in vacuo. This gave crude 11 (1.90 g, 3.21 mmol, 93%) as a white foam. $^1$H NMR (400 MHz, CDCl$_3$/CD$_3$OD) δ: 1.18 (d, 3H, J=6.9 Hz, CH$_3$-Ala), 1.42-1.98 (m, 6H, CH$_2$-Lys), 2.88-2.99 (m, 3H, N—CH$_2$-Lys+1H CH$_2$-Phe), 3.24 (dd, 1H, J$_1$=14.1 Hz, J$_2$=5.1 Hz, CH$_2$-Phe), 3.47 (br. t, 2H, J=5.0 Hz, CH$_2$N$_3$), 4.04-4.28 (m, 3H, CH$_2$OR+αH), 4.56 (m, 1H, α-H), 7.20-7.31 (m, 5H, H$_{Ar}$).

Example 7

AEC-D-Ala-Phe-Lys(Aloc)-OH (12): To a solution of 11 (1.90 g, 3.21 mmol) in a 1:1 mixture of dioxane and water (30 mL) were added NaHCO$_3$ (1.36 g, 16.1 mmol) and allyl chloroformate (377 μL, 3.53 mmol). The reaction mixture was stirred for 3 h at room temperature, after which the reaction mixture was concentrated to remove dioxane. The resulting aqueous solution was acidified with 1 N aqueous HCl to pH=3. The suspension was then extracted three times with ethyl acetate (3×50 mL). The combined organic layers were dried over Na$_2$SO$_4$, filtered, and concentrated to dryness. This gave crude 12 (1.83 g, max. 3.21 mmol, 100%) as a white solid. $^1$H NMR (400 MHz, CDCl$_3$/CD$_3$OD) δ: 1.19 (d, 3H, J=6.9 Hz, CH$_3$-Ala), 1.33-1.94 (m, 6H, CH$_2$-Lys), 2.95 (m, 1H, CH$_2$-Phe), 3.13 (m, 2H, N—CH$_2$-Lys), 3.21 (dd, 1H, J$_1$=14.1 Hz, J$_2$=5.2 Hz, CH$_2$-Phe), 3.46 (br. t, 2H, J=5.0 Hz, CH$_2$N$_3$), 4.00-4.26 (m, 3H, CH$_2$OR+α-H), 4.44 (m, 1H, H$_α$), 4.54 (br. d, 2H, J=5.0 Hz, CH$_2$-Aloc), 4.63 (m, 1H, α-H), 5.20 (d, 1H, J=10.1, CH$_2$=Aloc), 5.29 (d, 1H, J=17.1, CH$_2$=Aloc), 5.91 (m, 1H, CH-Aloc), 7.19-7.30 (m, 5H, H$_{Ar}$).

Example 8

AEC-D-Ala-Phe-Lys(Aloc)-PABA (13): To a solution of 12 (1.83 g, max. 3.21 mmol) in THF (50 mL) were added at −45° C. N-methylmorpholine (395 μL, 3.58 mmol) and isobutyl chloroformate (466 μL, 3.58 mmol). The reaction mixture was stirred at −45° C. for 2.5 h. Then, PABA (481 mg, 3.90 mmol) and N-methylmorpholine (429 μL, 3.90 mmol) were added consecutively. The reaction mixture was stirred for another 2.5 h at −45° C. and then warmed to room temperature in a 2 h period. The reaction mixture was concentrated and the residue was suspended in ethyl acetate (150 mL). This was washed with a saturated aqueous NaHCO$_3$ solution, 0.5 N aqueous KHSO$_4$, and brine, dried over Na$_2$SO$_4$, filtered, and concentrated to dryness. Column chromatography (CHCl$_3$/CH$_3$OH=9/1) gave 13 (1.54 g, 2.31 mmol, 72%) as a white solid. $^1$H NMR (400 MHz, CDCl$_3$/CD$_3$OD) δ: 1.24 (d, 3H, J=7.0 Hz, CH$_3$-Ala), 1.32-1.59 (m, 4H, CH$_2$-Lys), 1.71-1.80 (m, 1H, CH$_2$-Lys), 1.92-2.02 (m, 1H, CH$_2$-Lys), 2.99 (dd, 1H, J, =14.4 Hz, J$_2$=9.4 Hz, CH$_2$-Phe), 3.14 (m, 2H, NH—CH$_2$-Lys), 3.22-3.34 (m, 3H, CH$_2$—N$_3$+1H CH$_2$-Phe), 3.91 & 4.05-4.12 (2×m, 3H, CH$_2$CH$_2$OR+α-H), 4.48 (m, 1H, α-H), 4.53 (br. d, 2H, J=5.5 Hz, CH$_2$-Aloc), 4.57-4.62 (m, 3H, CH$_2$OH+α-H), 5.19 (d, 1H, J=10.3, CH$_2$=Aloc), 5.29 (d, 1H, J=17.2, CH$_2$=Aloc), 5.90 (m, 1H, CH-Aloc), 7.19-7.32 (m, 7H, H$_{Ar}$), 7.60 (m, 2H, H$_{Ar}$). FAB-MS m/e: 689 (M+Na)$^+$.

Example 9

AEC-D-Ala-Phe-Lys(Aloc)-PABC-PNP (14): To a solution of 13 (1.53 g, 2.29 mmol) in THF (40 mL) were added pyridine (561 μL, 6.88 mmol) and p-nitrophenyl chloroformate (925 mg, 4.59 mmol). The reaction mixture was stirred overnight and then concentrated to dryness. The residue was suspended in ethyl acetate (100 mL). This was washed with 10% aqueous citric acid, water, and brine, dried over Na$_2$SO$_4$, filtered, and concentrated to dryness. Column chromatography (CHCl$_3$/CH$_3$OH=93/7) gave 14 (1.12 g, 1.35 mmol, 59%) as an off-white solid. $^1$H NMR (400 MHz, CDCl$_3$/CD$_3$OD) δ: 1.24 (d, 3H, J=7.0 Hz, CH$_3$-Ala), 1.35-1.58 (m, 4H, CH$_2$-Lys), 1.71-1.83 (m, 1H, CH$_2$-Lys), 1.92-2.04 (m, 1H, CH$_2$-Lys), 3.00 (dd, 1H, J$_1$=14.2 Hz J$_2$=9.4 Hz, CH$_2$-Phe), 3.11-3.33 (m, 5H, NH—CH$_2$-Lys+CH$_2$—N$_3$+1H CH$_2$-Phe), 3.91 & 4.05-4.12 (2×m, 1H+2H, α-H+CH$_2$CH$_2$OR), 4.47-4.63 (m, 4H, CH$_2$-Aloc+2×α-H), 5.20 (d, 1H, J=10.0 Hz, CH$_2$=Aloc), 5.27 (s, 2H, CH$_2$OC(O)), 5.29 (d, 1H, CH$_2$=Aloc), δ 5.91 (m, 1H, CH-Aloc), 7.17-7.30 (m, 5H, H—Ar), 7.38-7.42 (m, 4H, H$_{Ar}$), 7.71 (d, 2H, J=8.4 Hz, H$_{Ar}$), 8.29 (m, 2H, H$_{Ar}$). ESI-MS m/e: 854 (M+Na)$^+$, 1686 (2M+Na)$^+$; HRMS calcd. for C$_{39}$H$_{45}$N$_9$O$_{12}$Na: m/e 854.3085, found: m/e 854.31062.

Example 10

AEC-D-Ala-Phe-Lys(Aloc)-PABC-PABA (15): To a solution of 14 (365 mg, 0.439 mmol) in DMF (5 mL) were added at 0° C. PABA (59.5 mg, 0.483 mmol), ethyldiisopropylamine (77 μL, 0.439 mmol), and 1-hydroxybenzotriazole (14.8 mg, 0.110 mmol). The reaction mixture was slowly warmed to room temperature and then stirred for 2 days. 10% isopropyl alcohol in ethyl acetate (30 mL) was added and the resulting solution was washed with water, a saturated aqueous NaHCO$_3$ solution, 0.5 N aqueous KHSO$_4$, and brine. The organic layer was dried over Na$_2$SO$_4$, filtered, and concentrated to dryness. Column chromatography (CHCl$_3$/CH$_3$OH=9/1) gave 15 (268 mg, 0.328 mmol, 75%) as a white solid. $^1$H NMR (400 MHz, CDCl$_3$/CD$_3$OD) δ: 1.23 (d, 3H, J=7.2 Hz, CH$_3$-Ala), 1.35-1.43 (m, 2H, CH$_2$-Lys), 1.49-1.58 (m, 2H, CH$_2$-Lys), 1.71-1.81 (m, 1H, CH$_2$-Lys), 1.95-2.02 (m, 1H, CH$_2$-Lys), 2.99 (dd, 1H, J$_1$=13.8 Hz J$_2$=9.2 Hz, CH$_2$-Phe), 3.13 (m, 2H, NH—CH$_2$-Lys), 3.20-3.32 (m, 3H, CH$_2$N$_3$+1H CH$_2$-Phe), 3.90 & 4.04-4.11 (2×m, 1H+2H, α-H+CH$_2$CH$_2$OR), 4.48 (m, 1H, α-H), 4.53 (d, 2H, J=5.5 Hz, CH$_2$-Aloc), 4.57 (s, 2H, CH$_2$OH), 4.60 (m, 1H, α-H), 5.15 (s, 2H, CH$_2$OC(O)), 5.19 (d, 1H, J=10.5 Hz, CH$_2$=Aloc), 5.29 (d, 1H, J=17.0 Hz, CH$_2$=Aloc), 5.90 (m, 1H, CH-Aloc), 7.19-7.29 (m, 7H, H$_{Ar}$), 7.35-742 (m, 4H, H$_{Ar}$), 7.65 (d, 2H, J=8.2 Hz, H—Ar); FAB-MS m/e: 816 (M+H)$^+$, 838 (M+Na)$^+$.

Example 11

AEC-D-Ala-Phe-Lys(Aloc)-PABC-PABC-PNP (16): To a solution of 15 (225 mg, 0.277 mmol) in THF (10 mL) were added p-nitrophenyl chloroformate (111 mg, 0.552 mmol) and pyridine (67 μL, 0.827 mmol). The reaction mixture was stirred at room temperature overnight. The reaction mixture was subsequently filtered and the filtrate was concentrated to dryness. Diethyl ether (25 mL) was added to the residue and the suspension was vigorously stirred for 15 min. The solid was filtered off, rinsed with more diethyl ether, collected, and dried in vacuo. Column chromatography (CHCl$_3$/CH$_3$OH=95/5) afforded 16 (248 mg, 0.253 mmol, 91%) as an off-white solid. $^1$H NMR (400 MHz, CDCl$_3$/CD$_3$OD) δ: 1.23 (d, 3H, J=7.3 Hz, CH$_3$-Ala), 1.34-1.43 (m, 2H, CH$_2$-Lys), 1.51-1.58 (m, 2H, CH$_2$-Lys), 1.72-1.81 (m, 1H, CH$_2$-Lys), 1.93-2.02 (m, 1H, CH$_2$-Lys), 2.99 (dd, 1H, J, =14.1 Hz, J$_2$=9.3 Hz, CH$_2$-Phe), 3.14 (m, 2H, NH—CH$_2$-Lys), 3.21-3.32 (m, 3H, CH$_2$N$_3$+1H CH$_2$-Phe), 3.89 & 4.04-4.11 (2×m, 1H+2H, α-H+ CH$_2$CH$_2$OR), 4.48 (m, 1H, (x-H), 4.53 (d, 2H, J=5.2 Hz, CH$_2$-Aloc), 4.60 (m, 1H, α-H), 5.16 (s, 2H, CH$_2$OC(O)), 5.19 (d, 1H, J=11.8 Hz, CH$_2$=Aloc), 5.25 (s, 2H, CH$_2$OC(O)), 5.29 (d, 1H, J=16.3 Hz, CH$_2$=Aloc), 5.90 (m, 1H, CH-Aloc), 7.17-7.29 (m, 5H, H$_{Ar}$), 7.36-7.42 (m, 6H, H$_{Ar}$), 7.48 (d, 2H, H$_{Ar}$), 7.66 (d, 2H, J=8.5 Hz, H$_{Ar}$), 8.28 (m, 2H, H$_{Ar}$); ESI-MS m/e: 981 (M+H)$^+$, 1003 (M+Na)$^+$; HRMS calcd. for C$_{47}$H$_{52}$N$_{10}$O$_{14}$Na: m/e 1003.35622, found: m/e 1003.35672.

Example 12

AEC-D-Ala-Phe-Lys(Aloc)-PABC-PABC-Dox (17): To a solution of 16 (240 mg, 0.245 mmol) in N-methylpyrrolidinone (5 mL) were added triethylamine (41 µL, 0.294 mmol) and doxorubicin hydrochloride (170 mg, 0.294 mmol). The reaction mixture was stirred in the dark overnight and subsequently diluted with 10% isopropyl alcohol in ethyl acetate (50 mL). The solution was washed with water, the aqueous layer was extracted with 10% isopropyl alcohol in ethyl acetate, and the combined organic layers were washed with brine, dried over Na$_2$SO$_4$, filtered, and concentrated to dryness. Diethyl ether (30 mL) was added to the residue, the suspension was vigorously stirred for 30 min, the solid was filtered off, washed with more diethyl ether, collected, and dried in vacuo. Column chromatography (CHCl$_3$/CH$_3$OH=93/7) provided 17 (256 mg, 0.185 mmol, 75%) as a red solid. $^1$H NMR (400 MHz, CDCl$_3$/CD$_3$OD) δ: 1.23 (d, 3H, J=7.1 Hz, CH$_3$-Ala), 1.28 (d, 3H, J=6.6 Hz, CH$_3$-sugar), 1.32-2.02 (m, 8H, 6H CH$_2$-Lys+2'-H), 2.17 (dd, 1H, J$_1$=14.6 Hz J$_2$=4.3 Hz, 8-H), 2.37 (br. d, 1H, J=14.6 Hz, 8-H), 2.99 (dd, 1H, CH$_2$-Phe), 3.07 (d, 1H, J=18.7 Hz, 10-H), 3.14 (m, 2H, NH—CH$_2$-Lys), 3.17-3.32 (m, 4H, 1H CH$_2$-Phe+2H CH$_2$N$_3$+10), 3.61 (br. s, 1H, 4-H), 3.83-3.92 (m, 2H, 3'-H+α-H/1H CH$_2$CH$_2$OR), 4.09 (s, 3H, OMe), 4.05-4.20 (m, 3H, 5'-H+2H CH$_2$CH$_2$OR/α-H), 4.48 (m, 1H, α-H), 4.53 (d, 2H, J=5.6 Hz, CH$_2$-Aloc), 4.60 (m, 1H, α-H), 4.77 (s, 2H, 14), 4.96 (m, 2H, CH$_2$OC(O)), 5.13 (s, 2H, CH$_2$OC(O)), 5.19 (d, 1H, J=10.5 Hz, CH$_2$=Aloc), 5.26-5.31 (m, 2H, 1H CH$_2$=Aloc+1'-H), 5.48 (m, 1H, 7-H), 5.91 (m, 1H, CH-Aloc), 7.19-7.48 (m, 12H, 11H H$_{Ar}$+3-H), 7.64 (d, 2H, J=8.0 Hz, H$_{Ar}$), 7.83 (t, 1H, J=8.0 Hz, 2-H), 8.05 (d, 1H, J=7.6 Hz, 1-H); ESI-MS m/e: 1408 (M+Na)$^+$; HRMS calcd. for C$_{68}$H$_{76}$N$_{10}$O$_{22}$Na: m/e 1407.5033, found: m/e 1407.51066.

Example 13

AEC-D-Ala-Phe-Lys-PABC-PABC-Dox-HCl (18): To a solution of 17 (100 mg, 0.0722 mmol) in THF (2 mL) were added tetrakis(triphenylphosphine)palladium(0) (16.7 mg, 0.0144 mmol) and morpholine (63 µL, 0.722 mmol). The reaction mixture was stirred in the dark for 1 h. Subsequently, ethyl acetate (25 mL) was added, the suspension was stirred for 5 min and then filtered. The residue was rinsed with ethyl acetate, collected, and suspended in ethyl acetate (25 mL). To this suspension, 1 N HCl in ethyl acetate (1 mL) was carefully added. The resulting red suspension was stirred for 5 min and filtered. The residue was thoroughly washed with ethyl acetate and then collected and dried in vacuo. This gave 18 (96.0 mg, 0.0718 mmol, 99%) as a red solid. ESI-MS m/e: 1301 (M+H)$^+$.

Example 14

N-propargylmaleimide (22): A solution of maleic anhydride (19, 2.5 g, 25.5 mmol) and propargylamine (20, 1.75 mL, 25.5 mmol) in glacial acetic acid (50 mL) was stirred in the dark overnight. The reaction mixture was concentrated to dryness and the residue was recrystallized from a mixture of isopropyl alcohol and water. This gave 21 (3.079 g, 20.1 mmol, 79%) as white crystals. Compound 21 (1.49 g, 9.70 mmol) was suspended in acetic anhydride (7 mL) and sodium acetate (437 mg, 5.33 mmol) was added. The resulting suspension was stirred at 65° C. for 2 h, cooled down to room temperature, and then poured into ice-cold water (75 mL). The aqueous solution was extracted three times with diethyl ether. The combined organic layers were dried over Na$_2$SO$_4$, filtered, and concentrated. Column chromatography (CH$_2$Cl$_2$/EtOAc=1/1) provided 22 (755 mg, 5.59 mmol, 58%) as an off-white solid. $^1$H NMR (400 MHz, CDCl$_3$) δ: 2.21 (t, 1H, J=2.6 Hz, ≡C—H), 4.30 (d, 2H, J=2.6 Hz, CH$_2$), 6.76 (s, 2H, =C—H).

Example 15

Compound 23: To a solution of 17 (10.0 mg, 7.22 µmol) in a 9:2 mixture of THF and water (0.11 mL), were added N-propargylmaleimide (2.0 mg, 15 µmol), 0.1 N aqueous sodium ascorbate (29 µL, 2.9 µmol), and 0.05 N aqueous CuSO$_4$.5H$_2$O (29 µL, 1.5 µmol). The reaction mixture was stirred in the dark for 4 h and then concentrated to dryness. The residue was suspended in diethyl ether and the suspension was stirred for 30 min. The solid was filtered off, washed with more diethyl ether, collected, and dried. Purification by column chromatography (CHCl$_3$/CH$_3$OH=93/7) gave 23 (6.3 mg, 4.1 tµmol, 57%) as a red solid. $^1$H NMR (400 MHz, CDCl$_3$/CD$_3$OD) δ: 1.20 (d, 3H, J=7.1 Hz, CH$_3$-Ala), 1.28 (d, 3H, J=6.6 Hz, CH$_3$-sugar), 1.35-2.06 (m, 8H, CH$_2$-Lys & 2'-H), 2.17 (dd, 1H, J$_1$=4.3 Hz, J$_2$=14.5 Hz, 8-H), 2.38 (br. d, 1H, J=14.5 Hz, 8-H), 2.99 (dd, 1H, CH$_2$-Phe), 3.04 (d, 1H, J=18.8 Hz, 10-H), 3.14 (m, 2H, Lys-CH$_2$—NH), 3.23 (d, 1H, J=18.8 Hz, 10), 3.33 (dd, 1H, CH$_2$-Phe), 3.62 (br. s, 1H, 4), 3.87 (m, 1H, 3'-H), 4.02-4.62 (m, 10H, 3×α-H, CH$_2$-Aloc, CH$_2$CH$_2$OR, CH$_2$CH$_2$N, 5'-H), 4.08 (s, 3H, OMe), 4.72 (s, 2H, NCH$_2$), 4.78 (s, 2H, 14), 4.95 (m, 2H, CH$_2$OC(O)), 5.11 (s, 2H, CH$_2$OC(O)), 5.18 (d, 1H, J=10.9 Hz, CH$_2$=Aloc), 5.26 (br. s, 1H, 1'-H), 5.28 (d, 1H, CH$_2$=Aloc), 5.47 (br. d, 1H, 7-H), 5.89 (m, 1H, CH-Aloc), 6.73 (s, 2H, CH=CH), 7.19-7.37 (m, 11H, H$_{Ar}$), 7.47 (d, 1H, J=8.4 Hz, 3-H), 7.64 (s, 1H, C=CH), 7.65 (d, 2H, H$_{Ar}$), 7.82 (t, 1H, J=8.1 Hz, 2-H), 8.02 (d, 1H, J=6.6 Hz, 1-H); ESI-MS m/e: 1543 (M+Na)$^+$; HRMS calcd. for C$_{75}$H$_{81}$N$_{11}$O$_{24}$Na: m/e 1542.53536, found: m/e 1542.53967.

Example 16

Compound 24: To a solution of 18 (21.9 mg, 16.4 µmol) in a 1:1 mixture of THF and water (0.25 mL), were added N-propargylmaleimide (4.4 mg, 33 µmol), 0.2 N aqueous sodium ascorbate (65 µL, 13 µmol), and 0.1 N aqueous CuSO$_4$.5H$_2$O (65 µL, 6.5 µmol). The reaction mixture was stirred in the dark for 4 h, quenched with acetic acid (95 µL)

and then concentrated to dryness. The residue was suspended in acetonitrile and the suspension was stirred for 30 min. The solid was filtered off, washed with more acetonitrile, collected, and dried. Characterization of compound 24 was carried out by conversion to compound 23 with allyl N-succinimidyl carbonate and triethylamine and purification by column chromatography (CHCl$_3$/CH$_3$OH=93/7). The $^1$H NMR spectrum proved identical to that of example 15.

References

1 Carter, P.; Smith, L.; Ryan, M. *Endoer.-Relat. Cancer* 2004, 11, 659-687.
2 Hamann, P. R.; Hinman, L. M.; Hollander, I.; Beyer, C. F.; Lindh, D.; Holcomb, R.; Hallett, W.; Tsou, H.-R.; Upeslacis, J.; Shochat, D.; Mountain, A.; Flowers, D. A.; Bernstein, I. *Bioconjugate Chem.* 2002, 13, 47-58.
3 De Groot, F. M. H.; Loos, W. J.; Koekkoek, R.; van Berkom, L. W. A.; Busseher, G. F.; Seelen, A. E.; Albrecht, C., de Bruijn, P.; Scheeren, H. W. *J. Org. Chem.* 2001, 66, 8815-8830.
4 Bagshawe, K. D. *Drug Dev. Res.* 1995, 34, 220-230.
5 Melton, R.; Connors, T.; Knox, R. J. *S.T.P. Pharma Sciences,* 1999, 13-33.
6 Huber, B. E.; Richards, C. A.; Krenitsky, T. A. *Proc. Natl. cad. Sci. USA,* 1991, 88, 8039-8043.
7 Bagshawe, K. D.; Springer, C. J.; Searle, F.; Antoniw, P.; Sharma, S. K.; Melton, R. G.; Sherwood, R. F. *Br. J. Cancer,* 1988, 58, 700-703.
8 Duncan, R. *Nat. Rev. Drug Discov.* 2003, 2, 347-360.
9 Ulbrich, K.; Etrych, T.; Chytil, P.; Pechar, M; Jelinkova, M.; Rihova, B. *Int. J. Pharm.* 2004, 277, 63-72.
10 Optional branching of L$_2$ is not shown here for reasons of clarity, but obviously the statements also hold when L$_2$ is branched.
11 Toki, B. E.; Cerveny, C. G.; Wahl, A. F.; Senter, P. D. *J. Org. Chem.,* 2002, 67, 1866-1872.
12 Greenwald, R. B., Choe, Y. H., McGuire, J., Conover, C. D., *Adv. Drug Delivery Rev.* 2003, 55, 217-250.
13 Kingsbury, W. D.; Boehm; J. C.; Mehta, R. J.; Grappel, S. F.; Gilvarg, C. *J. Med. Chem.* 1984, 27, 1447-1451.
14 (a) Franke, A. E.; Sievers, E. L.; and Scheinberg, D. A.; *Cancer Biother. Radiopharm.* 2000, 15, 459-476. (b) Murray, J. L., *Semin Oncol.* 2000, 27, 2564-2570 (c) Breitling, F., and Dubel, S., Recombinant Antibodies, John Wiley and Sons, New York, 1998.
15 Ringsdorf, H. *J. Polym. Sci., Polym. Symp.* 1975, 51, 135-153.
16 Elvira, C.; Gallardo, A.; San Roman, J.; Cifuentes, A.; *Molecules* 2005, 10, 114-125.
17 Huisgen, R. *Pure Appl. Chem.* 1989, 61, 613-628.
18 Tornøe, C. W.; Christensen, C.; Meldal, M. *J. Org. Chem.* 2002, 67, 3057-3064.
19 (a) Rostovtsev, V. V.; Green, L. G.; Fokin, V. V.; Sharpless, K. B. *Angew. Chem. Int. Ed.* 2002, 41, 2596-2599; (b) Sharpless, B. K.; Fokin, V.; Rostovsev, V.; Green, L.; Himo, F.; PCT Int. Appl. WO 03/101972.
20 Suh, B.-C.; Jeon, H.; Posner, G. H.; Silverman, S. M. *Tetrahedron Lett.* 2004, 45, 4623-4625.
21 Ryu, E.-H.; Zhao, Y. *Org. Lett.* 2005, 7, 1035-1037.
22 Sivakumar, K.; Xie, F.; Cash, B. M.; Long, S.; Barnhill, H. N.; Wang, Q. *Org. Lett.* 2004, 6, 4603-4606.
23 Deiters, A.; Cropp, T. A.; Summerere, D.; Mukherji, M.; Schultz, P. G. *Bioorg. Med. Chem. Lett.* 2004, 14, 5743-5747.
24 Link, A. J., Tirrell, D. A.; *J. Am. Chem. Soc.* 2003, 125, 11164-11165.
25 Wang, Q.; Chan, T. R.; Hilgraf R.; Fokin, V. V.; Sharpless, K. B.; Finn, M. G. *J. Am. Chem. Soc.* 2003, 125, 3192-3193.
26 Remington's Pharmaceutical Science (15th ed., Mack Publishing, Easton, Pa., 1980) (incorporated by reference in its entirety for all purposes)

The invention claimed is:

1. A method of producing a compound containing a reactive moiety and a cleavable therapeutic or diagnostic moiety, said method comprising reacting a first compound containing an azide-containing or acetylene-containing group, said first compound being of formula (V) or (VI), respectively:

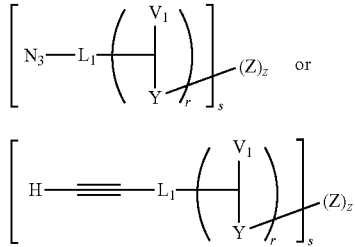

or a pharmaceutically acceptable salt thereof,
with a second compound containing an acetylene group or azide group, respectively, said second compound also containing a reactive moiety (RM), in a single step under formation of a third compound containing a triazole and a reactive moiety, said third compound being of formula (III) or (IV), respectively:

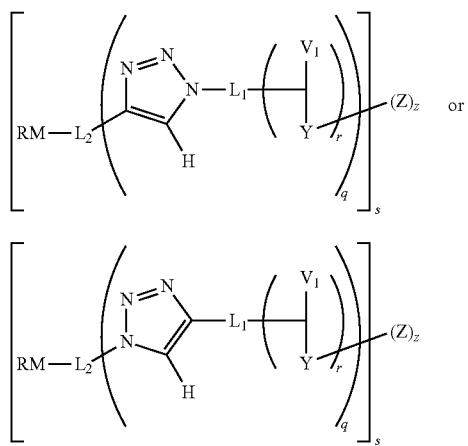

or a pharmaceutically acceptable salt thereof,
wherein
each $L_2$ is independently either a bond or a linking group linking RM to one or more triazole groups;
each $L_1$ is independently either a bond or a linking group linking the triazole, azido, or acetylene group to one or more $V_1$ and/or Y;
each $V_1$ is a conditionally-cleavable moiety, optionally following prior conditional transformation, which can be cleaved or transformed by a chemical, photochemical, physical, biological, or enzymatic process, cleavage of $V_1$ ultimately leading to release of one or more Z moieties;
each Y is independently absent or a self-eliminating spacer system which is comprised of one or more self-elimination spacers;
each Z is a therapeutic or diagnostic moiety, and each Z is directly coupled to either Y or $V_1$ when Y is absent;
q, r, and s are numbers representing degree of branching and are each independently a positive integer;
z is an integer $\geq 1$ and equal to or smaller than the total number of attachment sites for Z in the one or more $V_1$—Y moieties; and each RM is independently a reactive moiety selected from

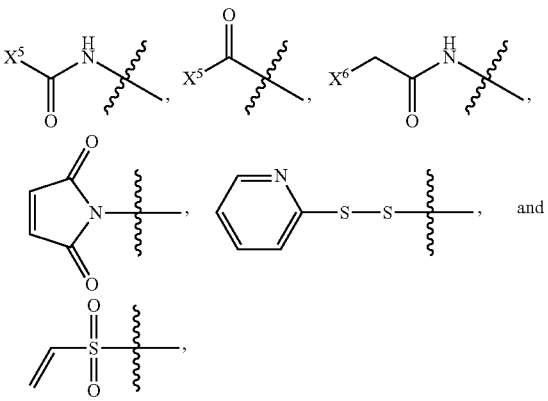

wherein $X^5$ is selected from —Cl, —Br, —I, —F, —O—N-succinimide, —O-(4-nitrophenyl), —O-pentafluorophenyl, —O-tetrafluorophenyl, —O—C(O)—$R^{29}$, and —O—C(O)—O$R^{29}$; wherein $R^{29}$ is branched or unbranched $C_1$-$C_{10}$ alkyl or aryl; and
$X^6$ is selected from —Cl, —Br, —I, —O-mesyl, —O-triflyl, and —O-tosyl.

2. The method of claim 1 which further comprises the reaction of said reactive moiety in said third compound of formula (III) or (IV) with a functional moiety to form a fourth compound of formula (I) or (II), respectively:

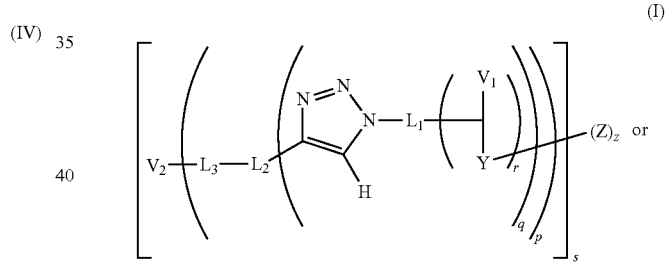

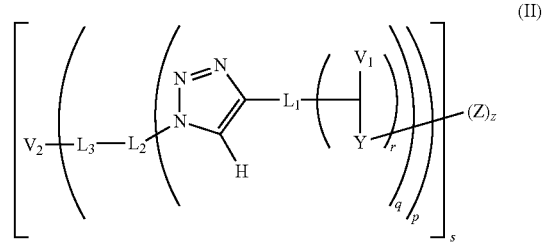

or a pharmaceutically acceptable salt thereof, and optionally said method further comprises reaction of said fourth compound with one or more adjuvant moieties to form a modified fourth compound, wherein
each $V_2$ is independently a targeting moiety and is selected from the group consisting of a protein or protein fragment, an antibody or an antibody fragment, a receptor-binding or peptide vector moiety, and a polymeric or dendritic moiety, or any combination thereof; and
each $L_3$ is independently either a bond or a linking group linking $V_2$, to $L_2$.

3. The method of claim 1 wherein Y is a self-elimination spacer system.

4. The method of claim 3 wherein the spacer system Y is selected from
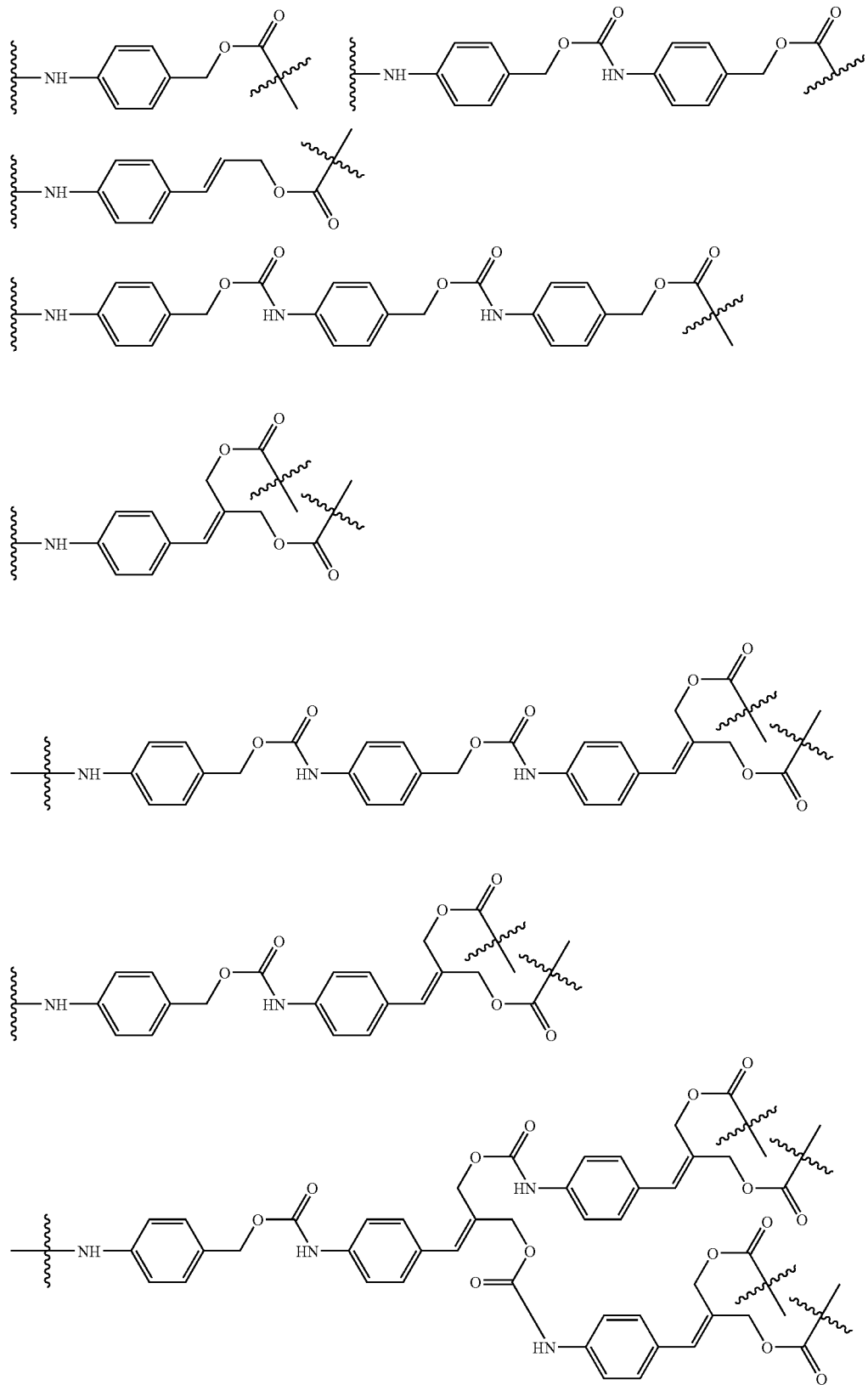

-continued

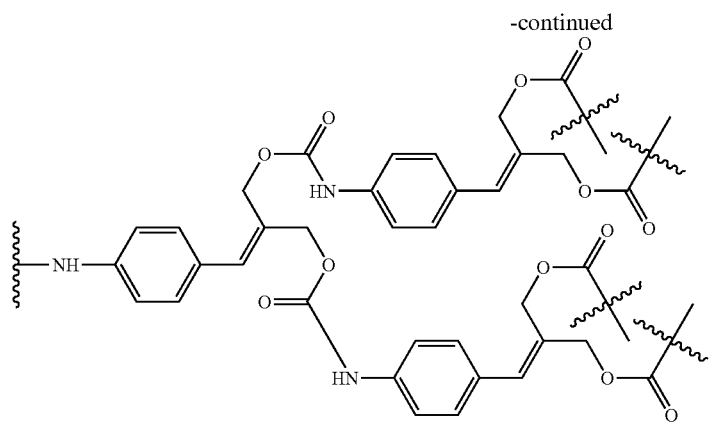

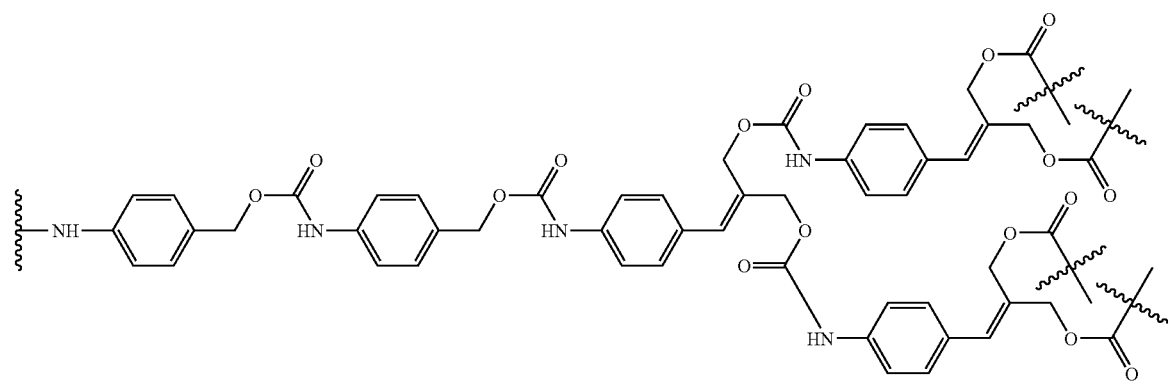

and from the formulae depicted above that further comprise one or more w-amino aminocarbonyl cyclization spacers connected to the right-hand side of the formulae.

5. The method of claim 1 wherein $V_1$ contains a substrate that can be cleaved by plasmin, a cathepsin, cathepsin B, β-glucuronidase, prostate-specific antigen (PSA), urokinase-type plasminogen activator (u-PA), a member of the family of matrix metalloproteinases, or an enzyme localized by means of directed enzyme prodrug therapy, or wherein $V_1$ contains a nitro(hetero)aromatic moiety that can be cleaved or transformed by reduction under hypoxic conditions or by reduction by a nitroreductase.

6. The method of claim 1 wherein one or more moieties Z are therapeutic agents.

7. The method of claim 1 wherein the moieties Z comprise at least two different therapeutic moieties.

8. The method of claim 1 wherein the moieties Z each are independently an antibiotic, an anti-bacterial agent, an anti-microbial agent, an anti-inflammatory agent, an anti-infectious disease agent, an anti-autoimmune disease agent, an anti-viral agent, or an anticancer agent.

9. The method of claim 1 wherein the moieties Z are each an anticancer agent.

10. The method of claim 1 wherein $L_1$ is

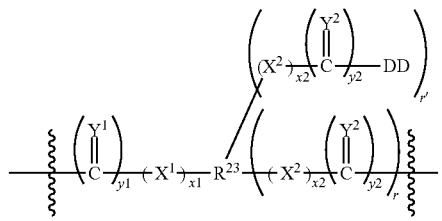

wherein
$X^1, Y^1$ are each independently O, $NR^{24}$, or S;
each $X^2, Y^2$ are each independently O, $NR^{25}$, or S;
each y1, y2, x1, and x2 are independently 0 or 1;
r is an integer selected from 1 (included) to 128 (included);
r' is an integer selected from 0 (included) to 127 (included);
r+r'≦128;
each DD is independently H, OH, or a leaving group;
$R^{23}$ is absent or is either a dendritic, branched or unbranched moiety and selected from optionally substituted alkylene or polyalkylene, optionally substituted heteroalkylene or polyheteroalkylene, optionally substituted arylene or polyarylene, optionally substituted heteroarylene or polyheteroarylene, optionally substituted cycloalkylene or polycycloalkylene, optionally substituted heterocycloalkylene or polyheterocycloalkylene, —(CH$_2$CH$_2$O)$_v$—, -alkylene-(CH$_2$CH$_2$O)$_v$—, —(CH$_2$CH$_2$O)$_v$-alkylene-, -alkylene-(CH$_2$CH$_2$O)$_v$-alkylene-, -heteroalkylene-(CH$_2$CH$_2$O)$_v$—, —(CH$_2$CH$_2$O)$_v$-heteroalkylene-, -heteroalkylene-(CH$_2$CH$_2$O)$_v$-alkylene-, -heteroalkylene-(CH$_2$CH$_2$O)$_v$-heteroalkylene-, -alkylene-(CH$_2$CH$_2$O),-heteroalkylene-, a dendritic structure, or an oligopeptide, and any combination of two or more of the above;

$R^{24}$ and $R^{25}$ are independently selected from H and alkyl; and v is selected from 1 (included) to 500 (included).

11. The method of claim 1 wherein $L_2$ is

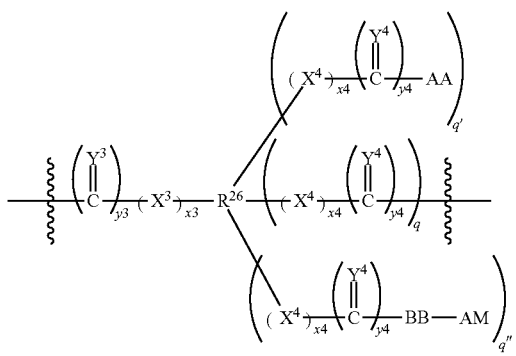

wherein $X^3$, $Y^3$ are each independently 0, $NR^{27}$, or S;

each $X^4$, $Y^4$ are each independently 0, $NR^{28}$, or S;

AA is either an azide or an acetylene group;

BB is a 1,4-substituted 1,2,3-triazole;

each AM is independently an adjuvant moiety;

each y3, y4, x3, and x4 are independently 0 or 1;

q is an integer selected from 1 (included) to 128 (included) and q' and q" are integers independently selected from 0 (included) to 127 (included) with q+q'+q"≦128;

$R^{26}$ is absent or is either a dendritic, branched or unbranched moiety and selected from optionally substituted alkylene or polyalkylene, optionally substituted heteroalkylene or polyheteroalkylene, optionally substituted arylene or polyarylene, optionally substituted heteroarylene or polyheteroarylene, optionally substituted cycloalkylene or polycycloalkylene, optionally substituted heterocycloalkylene or polyheterocycloalkylene, —(CH$_2$CH$_2$O)$_v$—, -alkylene-(CH$_2$CH$_2$O)$_v$—, —(CH$_2$CH$_2$O)$_v$-alkylene-, -alkylene-(CH$_2$CH$_2$O)$_v$-alkylene-, -heteroalkylene-(CH$_2$CH$_2$O)$_v$—, —(CH$_2$CH$_2$O)$_v$-heteroalkylene-, -heteroalkylene-(CH$_2$CH$_2$O)$_v$-alkylene-, -heteroalkylene-(CH$_2$CH$_2$O)$_v$-heteroalkylene-, -alkylene-(CH$_2$CH$_2$O),-heteroalkylene-, a dendritic structure, or an oligopeptide, and any combination of two or more of the above;

$R^{27}$ and $R^{28}$ are independently selected from H and alkyl;

v is selected from 1 (included) to 500 (included).

12. The method of claim 2 wherein the moiety $L_3$ is

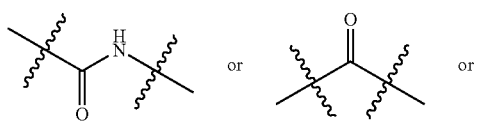

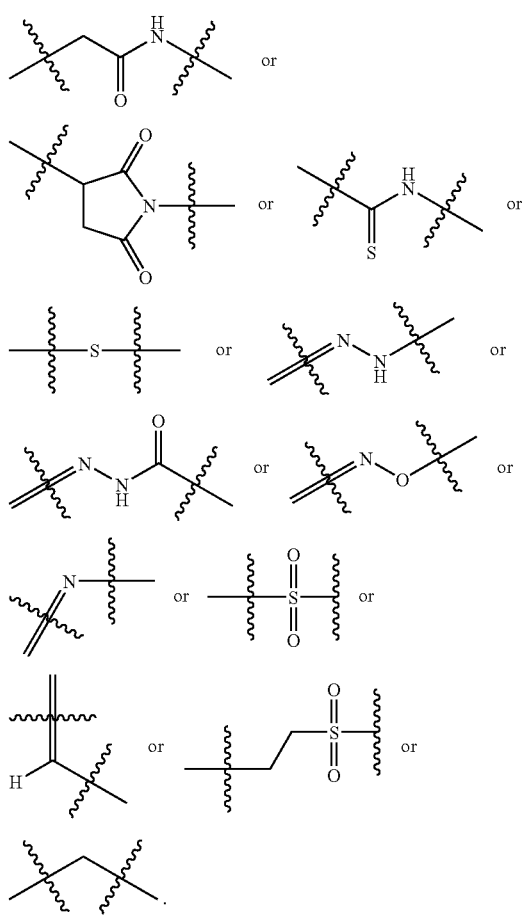

13. The method of claim 2 wherein the moiety $V_2$ is a targeting moiety and is selected from the group consisting of a protein or protein fragment, an antibody or an antibody fragment, a receptor-binding or peptide vector moiety, and a polymeric or dendritic moiety, or any combination thereof.

14. The method of claim 2 wherein $V_2$ is an antibody or antibody fragment.

15. The method of claim 2 wherein $V_2$ is a receptor-binding moiety.

16. The method of claim 2 wherein $V_2$ is a polymer.

17. The method of claim 2 wherein $V_2$ is an oligoethylene glycol or a polyethylene glycol or a derivative thereof.

18. The method of claim 1 wherein $L_1$ is connected to $V_1$.

19. The method of claim 2 wherein $L_3$ is

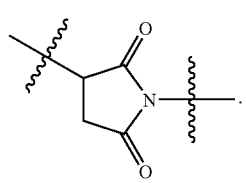

20. The method of claim 1 wherein Y is a self-elimination spacer system, and one or more moieties Z are therapeutic agents.

21. The method of claim 1 wherein $V^1$ is a dipeptide, tripeptide, tetrapeptide, or oligopeptide moiety comprised of natural L amino acids, unnatural D amino acids, or synthetic amino acids, or a peptidomimetic, or any combination thereof.

22. The method of claim 1 wherein RM is

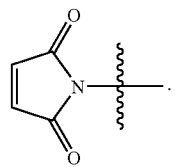

* * * * *

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: tetrapeptide

<400> SEQUENCE: 1

Gly Phe Leu Gly
1

<210> SEQ ID NO 2
<211> LENGTH: 4
<212> TYPE: PRT
<213> ORGANISM: Artificial Sequence
<220> FEATURE:
<223> OTHER INFORMATION: tetrapeptide

<400> SEQUENCE: 2

Ala Leu Ala Leu
1
```